US008017735B2

(12) United States Patent
Wang et al.

(10) Patent No.: US 8,017,735 B2
(45) Date of Patent: *Sep. 13, 2011

(54) ANTI-IGFR1 ANTIBODY THERAPEUTIC COMBINATIONS

(75) Inventors: Yan Wang, Scotch Plains, NJ (US); Jonathan A. Pachter, Chatham, NJ (US); Walter Robert Bishop, Pompton Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 897 days.

This patent is subject to a terminal disclaimer.

(21) Appl. No.: 10/993,395

(22) Filed: Nov. 19, 2004

(65) Prior Publication Data

US 2005/0136063 A1   Jun. 23, 2005

Related U.S. Application Data

(60) Provisional application No. 60/524,732, filed on Nov. 21, 2003.

(51) Int. Cl.
*C12P 21/08* (2006.01)
(52) U.S. Cl. ............... 530/387.3; 530/387.1; 424/130.1; 424/133.1
(58) Field of Classification Search ............... 530/387.1, 530/387.3; 424/130.1, 133.1
See application file for complete search history.

(56) References Cited

U.S. PATENT DOCUMENTS

| | | | | |
|---|---|---|---|---|
| 4,543,439 | A | 9/1985 | Frackelton, Jr. et al. | 935/92 |
| 4,604,463 | A | 8/1986 | Miyasaka et al. | |
| 4,659,516 | A | 4/1987 | Bowler et al. | |
| 5,198,340 | A | 3/1993 | Mukku | 435/7.8 |
| 5,260,291 | A | 11/1993 | Lunt et al. | |
| 5,262,308 | A | 11/1993 | Baserga | 435/69.1 |
| 5,362,718 | A | 11/1994 | Skotnicki et al. | |
| 5,518,999 | A * | 5/1996 | Nakamura et al. | 514/8 |
| 5,719,148 | A * | 2/1998 | Bishop et al. | 514/228.2 |
| 5,942,412 | A | 8/1999 | Prager et al. | 435/69.1 |
| 5,958,872 | A | 9/1999 | O'Connor et al. | 514/2 |
| 5,977,307 | A | 11/1999 | Friden et al. | 530/350 |
| 6,022,711 | A | 2/2000 | Cunningham et al. | |
| 6,084,085 | A | 7/2000 | Baserga et al. | 536/23.5 |
| 6,217,866 | B1 | 4/2001 | Schlessinger et al. | |
| 6,294,330 | B1 | 9/2001 | Michnick et al. | 435/6 |
| 6,300,129 | B1 | 10/2001 | Lonberg et al. | 435/326 |
| 6,316,462 | B1 | 11/2001 | Bishop et al. | 514/290 |
| 6,333,031 | B1 | 12/2001 | Olsson et al. | 424/93.7 |
| 6,346,390 | B1 | 2/2002 | Olsson et al. | 435/7.21 |
| 6,372,250 | B1 | 4/2002 | Pardridge | 424/450 |
| 6,403,569 | B1 | 6/2002 | Achterrath | |
| 6,537,988 | B2 | 3/2003 | Lee | 514/221 |
| 6,617,333 | B2 * | 9/2003 | Rabindran et al. | 514/291 |
| 6,645,775 | B1 | 11/2003 | Clark et al. | 436/518 |
| 6,774,122 | B2 | 8/2004 | Evans et al. | |
| 6,794,370 | B2 | 9/2004 | Achterrath | |
| 7,037,498 | B2 | 5/2006 | Cohen et al. | |
| 7,217,796 | B2 * | 5/2007 | Wang et al. | 530/387.3 |
| 7,235,576 | B1 | 6/2007 | Riedl et al. | |
| 7,326,567 | B2 | 2/2008 | Saha | |
| 2002/0022023 | A1 | 2/2002 | Ullrich et al. | 424/94.6 |
| 2002/0025313 | A1 | 2/2002 | Micklus et al. | 424/130.1 |
| 2002/0107187 | A1 | 8/2002 | Kingston et al. | 514/12 |
| 2002/0132275 | A1 | 9/2002 | Fidler et al. | 435/7.23 |
| 2002/0155095 | A1 | 10/2002 | Nagabhushan et al. | |
| 2002/0164333 | A1 | 11/2002 | Nemerow et al. | 424/146.1 |
| 2002/0169116 | A1 | 11/2002 | Kingston et al. | 514/12 |
| 2002/0187925 | A1 | 12/2002 | Kingston et al. | 514/2 |
| 2002/0197262 | A1 | 12/2002 | Hasan et al. | 424/178.1 |
| 2003/0021780 | A1 | 1/2003 | Smith et al. | 424/131.1 |
| 2003/0031658 | A1 | 2/2003 | Brodt et al. | 424/93.21 |
| 2003/0045676 | A1 | 3/2003 | Kingston et al. | 530/311 |
| 2003/0087342 | A1 | 5/2003 | Mermod et al. | |
| 2003/0088061 | A1 | 5/2003 | Staunton | 530/350 |
| 2003/0092631 | A1 | 5/2003 | Deshayes et al. | 514/14 |
| 2003/0138430 | A1 | 7/2003 | Stimmel et al. | 424/155.1 |
| 2003/0165502 | A1 | 9/2003 | Fujita-Yamaguchi | 424/145.1 |
| 2003/0195147 | A1 | 10/2003 | Pillutla et al. | 514/12 |
| 2003/0235582 | A1 | 12/2003 | Singh et al. | 424/141.1 |
| 2003/0236190 | A1 | 12/2003 | Pillutla et al. | 514/12 |
| 2004/0009154 | A1 | 1/2004 | Khan et al. | 424/93.21 |
| 2004/0009906 | A1 | 1/2004 | Kakkis et al. | 514/11 |
| 2004/0018191 | A1 * | 1/2004 | Wang et al. | 424/143.1 |
| 2004/0023887 | A1 | 2/2004 | Pillutla et al. | 514/17 |
| 2004/0038394 | A1 | 2/2004 | Kim et al. | |
| 2004/0047835 | A1 | 3/2004 | Blanco | 424/78.17 |
| 2004/0057950 | A1 | 3/2004 | Waksal et al. | 424/141.1 |
| 2004/0086511 | A1 | 5/2004 | Zack et al. | 424/146.1 |
| 2004/0102360 | A1 | 5/2004 | Barnett et al. | 514/1 |
| 2004/0116330 | A1 | 6/2004 | Naito et al. | 514/2 |
| 2004/0142381 | A1 | 7/2004 | Hubbard et al. | 435/7.1 |
| 2004/0166580 | A1 | 8/2004 | Plaetinck et al. | |

(Continued)

FOREIGN PATENT DOCUMENTS

DE    197 19 001 C2    5/2001

(Continued)

OTHER PUBLICATIONS

Rudikoff et al (Proc. Natl. Acad. Sci. USA 1982 vol. 79 p. 1979).*
Wilhelm and Chien (Current Pharmaceutical Design. 2002: 2255-2257).*
Moloney et al (Cancer Research, 2003. 63:5073-5083).*
Douglas et al (The Journal of Immunology, 2007. 178:3281-3287).*
Tappy (Diabetes, 1988. 12:1708-1714).*
Gura (Science, v278, 1997, pp. 1041-1042).*
Bharadwaj (The Journal of Clinical Investigation, 2007. 117:1130-1136).*
Polman et al (Medicine Cabinet, 2000, 173:398-402).*
Lockwood et al (Rheumatology, 2003. 42:1539-1544).*
Mariuzza et al. (Annu. Rev. Biophys. Biophys. Chem. 1987; 16: 139-159).*

(Continued)

*Primary Examiner* — Misook Yu
*Assistant Examiner* — Brad Duffy

(57) ABSTRACT

The present invention provides combinations including a binding composition, such as an anti-IGFR1 antibody, in association with a chemotherapeutic agent. Methods for using the combinations to treat medical conditions, such as cancer, are also provided.

41 Claims, No Drawings

U.S. PATENT DOCUMENTS

| | | | |
|---|---|---|---|
| 2004/0228859 A1 | 11/2004 | Graus et al. | 424/143.1 |
| 2004/0265307 A1 | 12/2004 | Singh et al. | |
| 2005/0008642 A1 | 1/2005 | Graus et al. | 424/145.1 |
| 2005/0009988 A1* | 1/2005 | Harris et al. | 525/56 |
| 2005/0048050 A1 | 3/2005 | Fujita-Yamaguchi | |
| 2005/0059672 A1 | 3/2005 | Zhu et al. | |
| 2005/0069539 A1 | 3/2005 | Cohen et al. | |
| 2005/0084906 A1 | 4/2005 | Goetsch et al. | |
| 2005/0176099 A1 | 8/2005 | Saha | |
| 2005/0186203 A1 | 8/2005 | Singh et al. | |
| 2005/0244408 A1 | 11/2005 | Cohen et al. | |
| 2005/0249728 A1 | 11/2005 | Singh et al. | |
| 2005/0249730 A1 | 11/2005 | Goetsch et al. | |
| 2005/0272637 A1 | 12/2005 | Clinton et al. | |
| 2005/0272755 A1 | 12/2005 | Denis et al. | |
| 2005/0276812 A1* | 12/2005 | Ebens et al. | 424/178.1 |
| 2005/0281812 A1 | 12/2005 | Cohen et al. | |
| 2006/0018910 A1 | 1/2006 | Gualberto et al. | |
| 2006/0140960 A1 | 6/2006 | Wang et al. | |
| 2006/0205810 A1 | 9/2006 | Zong et al. | |
| 2006/0233810 A1 | 10/2006 | Wang et al. | |
| 2006/0286103 A1 | 12/2006 | Kolhe et al. | |
| 2007/0071675 A1 | 3/2007 | Wu et al. | |
| 2008/0112888 A1 | 5/2008 | Wang | |

FOREIGN PATENT DOCUMENTS

| | | |
|---|---|---|
| FR | 2 834 900 | 7/2003 |
| FR | 2 834 990 | 7/2003 |
| FR | 2 834 991 | 7/2003 |
| WO | WO 91/04014 | 4/1991 |
| WO | WO91/13160 | 9/1991 |
| WO | WO 91/14438 | 10/1991 |
| WO | WO 97/44352 | 11/1997 |
| WO | WO98/17801 | 4/1998 |
| WO | WO 98/22092 | 5/1998 |
| WO | WO 98/45427 | 10/1998 |
| WO | WO 99/25378 | 5/1999 |
| WO | WO 99/28347 | 6/1999 |
| WO | WO 99/42127 | 8/1999 |
| WO | WO 99/60023 | 11/1999 |
| WO | WO 00/22130 | 4/2000 |
| WO | WO 0050067 | 8/2000 |
| WO | WO 00/69454 | 11/2000 |
| WO | WO 00/69454 A1 | 11/2000 |
| WO | WO 01/07084 | 2/2001 |
| WO | WO 01/30964 A2 | 5/2001 |
| WO | WO 01/36632 | 5/2001 |
| WO | WO 01/70268 A1 | 9/2001 |
| WO | WO 01/70930 A2 | 9/2001 |
| WO | WO 01/72771 | 10/2001 |
| WO | WO 01/75064 A2 | 10/2001 |
| WO | WO 02/04522 A2 | 1/2002 |
| WO | WO 02/07783 | 1/2002 |
| WO | WO 02/27017 A2 | 4/2002 |
| WO | WO 02/31500 | 4/2002 |
| WO | WO 02/43758 A2 | 6/2002 |
| WO | WO 02/053596 | 7/2002 |
| WO | WO 02/053596 A2 | 7/2002 |
| WO | WO 02/054066 | 7/2002 |
| WO | WO 02/072780 A2 | 9/2002 |
| WO | WO 02/088752 | 11/2002 |
| WO | WO 02/092599 A1 | 11/2002 |
| WO | WO 02/102854 A2 | 12/2002 |
| WO | WO 02/102972 | 12/2002 |
| WO | WO 02/102973 | 12/2002 |
| WO | WO 03/000928 | 1/2003 |
| WO | WO 03/014696 | 2/2003 |
| WO | WO 03/027246 A2 | 4/2003 |
| WO | WO03/039538 | 5/2003 |
| WO | WO 03/039538 A1 | 5/2003 |
| WO | WO 03/059951 A2 | 7/2003 |
| WO | WO 03/088910 A2 | 10/2003 |
| WO | WO 03/100008 | 12/2003 |
| WO | WO03/100008 | 12/2003 |
| WO | WO03/100059 | 12/2003 |
| WO | WO 03/106621 A2 | 12/2003 |
| WO | WO2004/030625 | 4/2004 |
| WO | WO2004/030627 | 4/2004 |
| WO | WO 2004/056865 | 7/2004 |
| WO | WO 2004/701529 | 8/2004 |
| WO | WO 2004/083248 | 9/2004 |
| WO | WO 2004/087756 | 10/2004 |
| WO | WO 2004/096224 A2 | 11/2004 |
| WO | WO2005/005635 | 1/2005 |
| WO | WO 2005/016967 A2 | 2/2005 |
| WO | WO 2005/016970 A2 | 2/2005 |
| WO | WO 2005/016970 A2 | 2/2005 |
| WO | WO 2005/016970 A3 | 2/2005 |
| WO | WO2005/061541 | 7/2005 |
| WO | WO2005/117980 | 12/2005 |
| WO | WO2006/013472 | 2/2006 |
| WO | WO2006/020258 | 2/2006 |
| WO | WO2007/093008 | 8/2007 |

OTHER PUBLICATIONS

Giusti et al. (Proc. Natl. Acad. Sci. USA. May 1987; 84 (9): 2926-2930).*
Winkler et al (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Brauch et al (Clin. Chem., 55(10):1770-1782, 2009).*
MacCallum et al. (J. Mol. Biol. Oct. 11, 1996; 262 (5): 732-745).*
Lucy J. Holt, et al., Domain antibodies: proteins for therapy, TRENDS in Biotechnology, vol. 21, No. 11, Nov. 2003.
Patent Cooperation Treaty International Search Report for application No. PCT/US2004/038842.
Maloney et al., An Anti-Insulin-like Growth Factor I Receptor Antibody That Is a Potent Inhibitor of Cancer Cell Proliferation, Cancer Research 63, 5073-5083 (2003).
Lu et al., Simultaneous Blockade of Both the Epidermal Growth Factor Receptor and the Insulin-like Growth . . . J. Bio. Chem.279(4): 2856-65 (2004).
Tang et al., Use of a peptide mimotope to guide the humanization of MRK-16, an anti-P-glycoprotein monoclonal antibody. J Biol Chem. Sep. 24, 1999;274(39):27371-8.
Boylan et al., The anti-proliferative effect of suramin towards tamoxifen-sensitive and resistant human breast cancer cell lines in relation to expression of receptors for epidermal growth factor and Insulin-like growth factor-I: growth stimulation in the presence of tamoxifen. Ann Oncol. Feb. 1998;9(2):205-11.
Happerfield et al., The localization of the insulin-like growth factor receptor 1 (IGFR-1) in benign and malignant breast tissue. J Pathol. Dec. 1997;183(4):412-7.
Clarke et al., Type I insulin-like growth factor receptor gene expression in normal human breast tissue treated with oestrogen and progesterone. Br J Cancer. 1997;75(2):251-7.
Van Den Berg et al., Expression of receptors for epidermal growth factor and insulin-like growth factor I by ZR-75-1 human breast cancer cell variants is inversely related: the effect of steroid hormones on insulin-like growth factor I receptor expression. Br J Cancer. Feb. 1996;73(4):477-81.
Lebon et al., Purification of insulin-like growth factor I receptor from human placental membranes. J Biol Chem. Jun. 15, 1986;261(17)7685-9.
Warren et al., Induction of vascular endothelial growth factor by insulin-like growth factor 1 in colorectal carcinoma. J Biol Chem. Nov. 15, 1996;271(46):29483-8.
Auclair et al., Antiinsulin receptor autoantibodies induce insulin receptors to constitutively associate with insulin receptor substrate-1 and -2 and cause severe cell resistance to both insulin and insulin-like growth factor I. J Clin Endocrinol Metab. Sep. 1999;84(9):3197-206.
Gori et al., Effects of androgens on the insulin-like growth factor system in an androgen-responsive human osteoblastic cell line. Endocrinology. Dec. 1999;140(12):5579-86.
Kasprzyk et al., Therapy of an animal model of human gastric cancer using a combination of anti-erbB-2 monoclonal antibodies. Cancer Res. May 15, 1992;52(10):2771-6.
Drebin et al., Monoclonal antibodies reactive with distinct domains of the neu oncogene-encoded p185 molecule exert synergistic antitumor effects in vivo. Oncogene. Mar. 1988;2(3):273-7.

Shin et al., Proapoptotic activity of cell-permeable anti-Akt single-chain antibodies. Cancer Res. Apr. 1, 2005;65(7):2815-24.

Lu et al., A fully human recombinant IgG-like bispecific antibody to both the epidermal growth factor receptor and the insulin-like growth factor receptor for enhanced antitumor activity. J Biol Chem. May 20, 2005;280(20):19665-72.

Cohen et al., Combination therapy enhances the inhibition of tumor growth with the fully human anti-type 1 insulin-like growth factor receptor monoclonal antibody CP-751,871. Clin Cancer Res. Mar. 1, 2005;11(5):2063-73.

Wu et al., In vivo effects of the human type I insulin-like growth factor receptor antibody A12 on androgen-dependent and androgen-independent xenograft human prostate tumors. Clin Cancer Res. Apr. 15, 2005;11(8):3065-74.

Goetsch et al., A recombinant humanized anti-insulin-like growth factor receptor type I antibody (h7C10) enhances the antitumor activity of vinorelbine and anti-epidermal growth factor receptor therapy against human cancer xenografts. Int J Cancer. Jan. 10, 2005;113(2):316-28.

Granerus et al., Effects of insulin-like growth factor-binding protein 2 and an IGF-type I receptor-blocking antibody on apoptosis in human teratocarcinoma cells in vitro. Cell Biol Int. 2001;25(8):825-8.

Kaliman et al., Antipeptide antibody to the insulin-like growth factor-I receptor sequence 1232-1246 inhibits the receptor kinase activity. J Biol Chem. May 25, 1992;267(15):10645-51.

Rodeck et al., Interactions between growth factor receptors and corresponding monoclonal antibodies in human tumors. J Cell Biochem. Dec. 1987;35(4):315-20.

Iwakiri et al., Autocrine growth of Epstein-Barr virus-positive gastric carcinoma cells mediated by an Epstein-Barr virus-encoded small RNA. Cancer Res. Nov. 1, 2003;63(21):7062-7.

Kiess at al., Human neuroblastoma cells use either insulin-like growth factor-I or insulin-like growth factor-II in an autocrine pathway via the IGF-I receptor: variability of IGF, IGF binding protein (IGFBP) and IGF receptor gene expression and IGF and IGFBP secretion in human neuroblastoma cells in relation to cellular proliferation. Regul Pept. Sep. 26, 1997;72(1):19-29.

Pritchard et al., Synovial fibroblasts from patients with rheumatoid arthritis, like fibroblasts from Graves' disease, express high levels of IL-16 when treated with Igs against insulin-like growth factor-1 receptor, J Immunol. Sep. 1, 2004;173(5):3564-9.

Jackson-Booth et al., Inhibition of the biologic response to insulin-like growth factor I in MCF-7 breast cancer cells by a new monoclonal antibody to the Insulin-like growth factor-I receptor. The Importance of receptor down-regulation. Horm Metab Res. Nov.-Dec. 2003;35(11-12):850-6.

Carboni et al., Tumor development by transgenic expression of a constitutively active insulin-like growth factor I receptor. Cancer Res. May 1, 2005;65(9):3781-7.

Remacle-Bonnet et al., Insulin-like growth factor-I protects colon cancer cells from death factor-induced apoptosis by potentiating tumor necrosis factor alpha-induced mitogen-activated protein kinase and nuclear factor kappaB signaling pathways. Cancer Res. Apr. 1, 2000;60(7):2007-17.

Lahm et al., Blockade of the insulin-like growth-factor-I receptor inhibits growth of human colorectal cancer cells: evidence of a functional IGF-II-mediated autocrine loop. Im J Cancer. Aug. 1, 1994;58(3):452-9.

Steele-Perkins et al., Monoclonal antibody alpha IR-3 inhibits the ability of insulin-like growth factor II to stimulate a signal from the type I receptor without inhibiting its binding. Biochem Biophys Res Commun. Sep. 28, 1990;171(3):1244-51.

Scotlandi et al., Prognostic and therapeutic relevance of HER2 expression in osteosarcoma and Ewing's sarcoma. Eur J Cancer. Jun. 2005;41(9):1349-61.

Agus et al., Response of prostate cancer to anti-Her-2/neu antibody in androgen-dependent and -independent human xenograft models. Cancer Res. Oct. 1, 1999;59(19):4761-4.

Pietras et al., Monoclonal antibody to HER-2/neureceptor modulates repair of radiation-induced DNA damage and enhances radiosensitivity of human breast cancer cells overexpressing this oncogene. Cancer Res. Mar. 15, 1999;59(6):1347-55.

Goldenberg, Marvin M., Trastuzumab, a recombinant DNA-derived humanized monoclonal antibody, a novel agent for the treatment of metastatic breast cancer. Clin Ther. Feb. 1999;21(2):309-18. Review.

Seely et al., Retroviral expression of a kinase-defective IGF-I receptor suppresses growth and causes apoptosis of CHO and U87 cells in-vivo. BMC Cancer. May 31, 2002;2:15.; 1-9.

Soos et al., A panel of monoclonal antibodies for the type I insulin-like growth factor receptor. Epitope mapping, effects on ligand binding, and biological activity. J Biol Chem. Jun. 25, 1992;267(18):12955-63.

Kalebic et al., In vivo treatment with antibody against IGF-1 receptor suppresses growth of human rhabdomyosarcoma and down-regulates p34cdc2. Cancer Res. Nov. 1, 1994;54(21):5531-4.

Baserga, Renato; The insulin-like growth factor I receptor: a key to tumor growth?Cancer Res. Jan. 15, 1995;55(2):249-52.

Rubini et al., Characterization of an antibody that can detect an activated IGF-I receptor in human cancers. Exp Cell Res. Aug. 25, 1999;251(1):22-32.

Lin et al., Structure-Function Relationships in Glucagon: Properties of Highly Purified Des-His$^1$-, Monoiodo-, and [Des-Asn$^{28}$,Thr$^{29}$](homoserine lactone$^{27}$)-glucagon, Biochemistry 14(8): 1559-1563 (1975).

Acland et al., Subcellular fate of the Int-2 oncoprotein is determined by choice of initiation codon, Nature 343:662-665 (Feb. 15, 1990).

Cordera et al., Inhibition of Insulin and Epidermal Growth Factor (EGF) Receptor Autophosphorylation by a Human Polyclonal IgG, Biochemical and Biophysical Research Communications, 132(3): 991-1000 (Nov. 15, 1985).

Freund et al., Functional Insulin and Insulin-like Growth Factor-1 Receptors are Preferentially Expressed in Multiple Myeloma Cell Lines as Compared to B-Lymphoblastoid Cell Lines, Cancer Res. 54(12):3179-3185 (Jun. 15, 1994).

Rudikoff et al., Single Amino Acid Substitution Altering Antigen-Binding Specificity, Proc. Natl. Acad. Sci., 79:1979-1983 (Mar. 1982).

Burgess et al., Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell. Bio. 111:2129-2138 (Nov. 1990).

Lazar et al., Transforming Growth Factor α: Mutation of Aspartic Acid 47 and Leucine 48 Results in Different Biological Activities, Mol. Cell. Bio. 8(3):1247-1252 (Mar. 1988).

Schwartz et al., A Superactive Insulin: [B10-Aspartic acid]insulin(human), Proc. Natl. Acad. Sci., 84:6408-6411 (Sep. 1987).

Jackson et al., Insulin receptor substrate-1 is the predominant signaling molecule activated by insulin-like growth factor-I, insulin, and interleukin-4 in estrogen receptor-positive human breast cancer cells.J Biol Chem. 273(16):9994-10003 (1998).

Desnoyers et al., Novel non-isotopic method for the localization of receptors in tissue sections., : J Histochem Cytochem. 49(12):1509-18 (2001).

Ricort et al., Insulin-like growth factor (IGF) binding protein-3 Inhibits type 1 IGF receptor activation independently of its IGF binding affinity, Endocrinology.142(1):108-13 (2001).

Kaufman, R.J., Selection and coamplification of heterogeneous genes in mammalian cells, Methods in Enzymology 185: 537-566 (1990).

Ju et al., Nucleotide sequence analysis of the long terminal repeat (LTR) of avian retroviruses: structural similarities with transposable elements.Cell. 22(2 Pt 2):379-86 (1980).

Takebe et al., SR alpha promoter: an efficient and versatile mammalian cDNA expression system composed of the simian virus 40 early promoter and the R-U5 segment of human T-cell leukemia virus type 1 long terminal repeat.Mol Cell Biol. 8(1):466-72 (1988).

Oberholzer et al., Increased survival in sepsis by in vivo adenovitus-induced expression of IL-10 in dendritic cells. J Immunol. 168(7):3412-8 (2002).

Wahle, Elmar; The end of the message: 3'-end processing leading to polyadenylated messenger RNA. Bioessays. 14(2):113-8 (1992).

Stefania Benini et al., Inhibition of Insulin-like Growth Factor I Receptor Increases the Antitumor Activity of Doxorubicin and Vincristine Against Ewing's Sarcoma Cells, Clinical Cancer Research, vol. 7, 1790-1797, Jun. 2001.

V.M. Macaulay, Insulin-like Growth Factors and Cancer, Br. J. Cancer, 65, 311-320, 1992.

Mariana Resnicoff et al., The Role of the Insulin-like Growth Factor I Receptor in Transformation and Apoptosis, Kimmel Cancer Institute, Thomas Jefferson University pp. 76-81.

Xiangdang Liu et al., Inhibition of Insulin-like Growth Factor I Receptor Expression in Neuroblastoma Cells Induces the Regression of Established Tumors in Mice, Cancer Research 58, 5432-5438, Dec. 1, 1998.

Jamie L. Resnik et al., Elevated Insulin-like Growth Factor I Receptor Autophosphorylation and Kinase Activity in Human Breast Cancer, Cancer Research 58, 1159-1164, Mar. 15, 1998.

Fredrika Pekonen et al., Receptors for Epidermal Growth Factor and Insulin-like Growth Factor I and Their Relation to Steroid Receptors in Human Breast Cancer, Cancer Research 48, 1343-1347, Mar. 1, 1988.

Quynh T. Rohlik et al., An Antibody to the Receptor for Insulin-like Growth Factor I Inhibits the Growth of MCF-7 Cells in Tissue Culture, Biochemical and Biophysical Research Communications, vol. 149, No. 1, 276-281, 1987.

Carlos L. Arteaga et al., Blockade of the Type I Somatomedin Receptor Inhibits Growth of Human Breast Cancer Cells in Athymic Mice, J. Clin. Invest., vol. 84, 1418-1423, Nov. 1989.

Ted Gansler et al., Rapid Communication Antibody to Type I Insulin-like Growth Factor Receptor Inhibits Growth of Wilms' Tumor in Culture and in Athymic Mice, American Journal of Pathology, vol. 135, No. 6, 961-966, Dec. 1989.

Krzysztof Reiss et al., Inhibition of Tumor Growth by a Dominant Negative Mutant of the Insulin-like Growth Factor I Receptor with a Bystander Effect, Clinical Cancer Research, vol. 4, 2647-2655, Nov. 1998.

Carlos L. Arteaga et al., Growth Inhibition of Human Breast Cancer Cells in Vitro with an Antobody Against the Type I Somatomedin Receptor, Cancer Research, 49, 6237-6241, Nov. 15, 1989.

Sandra E. Dunn et al., A Dominant Negative Mutant of the Insulin-like Growth Factor-I Receptor Inhibits the Adhesion, Invasion, and Metastasis of Breast Cancer, Cancer Research, 58, 3353-3361, Aug. 1, 1998.

Peter Burfeind, Antisense RNA to the Type I Insulin-like Growth Factor Receptor Suppresses Tumor Growth and Prevents Invasion by Rat Prostate Cancer Cells In Vivo, Proc. Natl. Acad. Sci. USA, vol. 93 7263-7268, Jul. 1996.

Diane Prager et al., Dominant Negative Inhibition of Tumorigenesis In Vivo by Human Insulin-like Growth Factor I Receptor Mutant, Proc. Natl. Acad. Sci. USA, vol. 91, 2181-2185, Mar. 1994.

Deepali Sachdev, A Chimeric Humanized Single-Chain Antibody Against the Type I Insulin-like Growth Factor (IGF) Receptor Renders Breast Cancer Cells Refractory to the Mitogenic Effects of IGF-1, Cancer Research 63, 627-635, 2003.

Hakam et al., Expression of Insulin-like Growth Factor-1 Receptor in Human Colorectal Cancer Human Pathology (1999) 30(10): 1128-1133.

Sepp-Lorenzino, Structure and function of the insulin-like growth factor I receptor, Breast Cancer Research and Treatment (1998) 47: 235-253.

Happerfield, et al., "The localization of insulin-like growth factor receptor 1 (IGFR1) in benign and malignant breast tissue" Journal of Pathology 183:412-417 (1997).

Search Report for International Application No. PCT/US03/16283.

R&D Systems catalogue pages—monoclonal anti-IGF-IR antibody MAB391.

Xiong et al., "Growth-stimulatory monoclonal antibodies against human insulin-like growth factor I receptor" Proc. Nat. Acad. Sci. 89: 5356-5360 (1992).

Li et al., "Two new monoclonal antibodies against the α subunit of the human insulin-like growth factor-I receptor" Biochem. Biophys. Res. Comm. 196(1):92-98 (1993).

Kull et al., "Monoclonal antibodies to receptors for insulin and somatomedin-C" J. Biol. Chem. 258(10):6561-6566 (1983).

Butler et al., "Insulin-like growth factor-I receptor signal transduction: at the interface between physiology and cell biology" Comp. Biochem. Physiol. (B) 121(1):19-26 (1998).

Chan et al., "Plasma insulin-like growth factor-I and prostate cancer risk: a prospective study" Science. 279(5350):563-566 (1998).

Xie et al., "Expression of insulin-like growth factor-1 receptor in synovial sarcoma: association with an aggressive phenotype" Cancer Res. 59(15):3588-3591 (1999).

Steller et al., "Overexpression of the insulin-like growth factor-1 receptor and autocrine stimulation in human cervical cancer cells" Cancer Res. 56(8):1761-1765 (1996).

Pandini et al., "Insulin and insulin-like growth factor-I (IGF-I) receptor overexpression in breast cancers leads to insulin/IGF-I hybrid receptor overexpression: evidence for a second mechanism of IGF-I signaling" Clin. Cancer Res. 5(7):1935-1944 (1999).

Webster et al., "Repression of the insulin receptor promoter by the tumor suppressor gene product p53: a possible mechanism for receptor overexpression in breast cancer" Cancer Res. 56(12):2781-2788 (1996).

Ben-Schlomo et al., "Acromegaly" Endocrin. Metab. Clin. N. America 30(3):565-583 (2001).

Li et al., "Single-chain antibodies against human insulin-like growth factor I receptor: expression, purification, and effect on tumor growth", Cancer Immunol. Immunother. 49: 243-252 (2000).

Burtrum et al., "A fully human monoclonal antibody to the insulin-like growth factor I receptor blocks ligand-dependent signaling and inhibits human tumor growth in vivo." Cancer Res. Dec. 15, 2003;63(24):8912-21.

BusinessWire, "Imclone systems incorporated reports advancements in several pipeline programs" (Jul. 14, 2003).

Zhenping Zhu, "Monoclonal Antibodies in Cancer-Fourth International Congress (Part II), Colorado Springs, CO, USA" Investigational Drug Database Meeting Report (Sep. 3-6, 2004).

Laura Williams, "American Association for Cancer Research-94th Annual Meeting (Part III)—Overnight Report, Washington, D.C., USA" Investigational Drug Database Meeting Report (Jul. 11-14, 2003).

Norderhaug et al., Versatile vectors for transient and stable expression of recombinant antibody molecules in mammalian cells, J. Immunol. Methods. May 12, 1997;204(1):77-87.

Zhang et al., An adenoviral vector expressing functional heterogeneous proteins herpes simplex viral thymidine kinase and human interleukin-2 has enhanced in vivo antitumor activity against medullary thyroid carcinoma, Endocr. Relat. Cancer Dec. 2001;8(4):315-25.

Flamez et al., Production in *Escherichia coli* of a functional murine and murine::human chimeric F(ab')2 fragment and mature antibody directed against human placental alkaline phosphatase, J. Biotechnol. Sep. 29, 1995;42(2):133-43.

Bebbington CR: "Expression of antibody genes in nonlymphoid mammalian cells" Methods: A companion to methods in Enzymology, Academic Press Inc., New York, NY, US, vol. 2, No. 2, Apr. 1991, pp. 136-145.

Page MJ et al.: "High level expression of the humanized monoclonal antibody campath-1h in Chinese hamster ovary cells" Bio/technology, Nature publishing Co., New York, NY, US, vol. 9, No. 1, Jan. 1991, pp. 64-68.

Petit et al., Activity of SCH 66336, a tricyclic farnesyltransferase inhibitor, against human tumor colony-forming units. Ann Oncol. Apr. 1999;10(4):449-53.

Wilhelm et al., BAY 43-9006: preclinical data., Curr Pharm Des. 2002;8(25):2255-7.

Zujewski et al., Phase I and pharmacokinetic study of farnesyl protein transferase inhibitor R115777 in advanced cancer.J Clin Oncol. Feb. 2000;18(4):927-41.

Bomgaards et al., The development of camptothecin analogs in childhood cancers.Oncologist. 2001;6(6):506-16.

Bollag et al., Retinoids in cancer prevention and therapy.Ann Oncol. Jul. 1992;3(7):513-26.

Ke et al., Effects of CP-336,156, a new, nonsteroidal estrogen agonist/antagonist, on bone, serum cholesterol, uterus and body composition in rat models.Endocrinology. Apr. 1998;139(4):2068-76.

Nutall et al., Idoxifene: a novel selective estrogen receptor modulator prevents bone loss and lowers cholesterol levels in ovariectomized rats and decreases uterine weight in intact rats., Endocrinology. Dec. 1998;139(12):5224-34.

Lee et al., BMS-247550: a novel epothilone analog with a mode of action similar to paclitaxel but possessing superior antitumor efficacy.Clin Cancer Res. May 2001;7(5):1429-37.

Greenberger et al., A new antiestrogen, 2-(4-hydroxy-phenyl)-3-methyl-1-[4-(2-piperidin-1-yl-ethoxy)-benzyl]-1H-indol-5-ol hydrochloride (ERA-923), inhibits the growth of tamoxifen-sensitive and -resistant tumors and is devoid of uterotropic effects in mice and rats., Clin Cancer Res. Oct. 2001;7(10):3166-77.

Sato et al., LY353381.HCI: a novel raloxifene analog with improved SERM potency and efficacy in vivo., J Pharmacol Exp Ther. Oct. 1998;287(1):1-7.

Vlahos et al., A specific inhibitor of phosphatidylinositol 3-kinase, 2-(4-morpholinyl)-8-phenyl-4H-1-benzopyran-4-one (LY294002)., J Biol Chem. Feb. 18, 1994;269(7):5241-8.

Lowinger et al., Design and discovery of small molecules targeting raf-1 kinase.Curr Pharm Des. 2002;8(25):2269-78.

Hunt et al., Discovery of (R)-7-cyano-2,3,4, 5-tetrahydro-1-(1H-imidazol-4-ylmethyl)-3-(phenylmethyl)-4-(2-thienylsulfonyl)-1H-1,4-benzodiazepine (BMS-214662), a farnesyltransferase inhibitor with potent preclinical antitumor activity., J Med Chem. Oct. 5, 2000;43(20):3587-95.

Hidalgo et al., Phase I and pharmacologic study of OSI-774, an epidermal growth factor receptor tyrosine kinase inhibitor, in patients with advanced solid malignancies.J Clin Oncol. Jul. 1, 2001;19(13):3267-79.

Rusnak et al., The effects of the novel, reversible epidermal growth factor receptor/ErbB-2 tyrosine kinase inhibitor, GW2016, on the growth of human normal and tumor-derived cell lines in vitro and in vivo.Mol Cancer Ther. Dec. 2001;1(2):85-94.

Yang et al., Eradication of established tumors by a fully human monoclonal antibody to the epidermal growth factor receptor without concomitant chemotherapy.Cancer Res. Mar. 15, 1999;59(6):1236-43.

Hideshima et al., Targeting p38 MAPK inhibits multiple myeloma cell growth in the bone marrow milieu.Blood. Jan. 15, 2003;101(2):703-5. Epub Sep. 5, 2002.

Yu et al., mTOR, a novel target in breast cancer: the effect of CCI-779, an mTOR inhibitor, in preclinical models of breast cancer. Endocr Relat Cancer. Sep. 2001;8(3):249-58.

Alexandre et al.., La rapamycine et le CCI-779, Bull Cancer. Oct. 1999;86(10):808-11.

Wissner et al., Synthesis and structure-activity relationships of 6,7-disubstituted 4-anilinoquinoline-3-carbonitriles. The design of an orally active, irreversible inhibitor of the tyrosine kinase activity of the epidermal growth factor receptor (EGFR) and the human epidermal growth factor receptor-2 (HER-2). J Med Chem. Jan. 2, 2003;46(1):49-63.

Sebolt-Leopold et al., Blockade of the MAP kinase pathway suppresses growth of colon tumors in vivo., Nat Med. Jul. 1999;5(7):810-816.

Malet et al., Effect of 4-hydroxytamoxifen isomers on growth and ultrastructural aspects of normal human breast epithelial (HBE) cells in culture., J Steroid Biochem Mol Biol. Nov. 2002;82(4-5):289-96.

Komm et al., Developing a SERM: stringent preclinical selection criteria leading to an acceptable candidate (WAY-140424) for clinical evaluation., Ann N Y Acad Sci. Dec. 2001;949:317-26: Preface (Sherman); The Basic Biology of SERMs (Margolis); Cancer treatment and prevention (Dunn et al.).

Guo et al., Population pharmacokinetics of a HER2 tyrosine kinase inhibitor CP-724,714 in patients with advanced malignant HER2 positive solid tumors; Cancer Chemo Pharma 2007; 60:799-809.

Business Wire, "Imclone systems incorporated reports advancements in several pipeline programs" (Jul. 14, 2003).

Beech et al., Insulin-like growth factor-I receptor antagonism results in increased cytotoxicity of breast cancer cells to doxorubicin and taxol, Oncology Reports (2001) 8:325-329.

Green et al., Antibody engineering via genetic engineering of the mouse: XenoMouse strains are a vehicle for the facile generation of therapeutic human monoclonal antibodies, J. Immuno. Meth. (1999) 231(1-2): 11-23.

Resnicoff et al., Rat glioblastoma cells expressing an antisense RNA to the insulin-like growth factor-1 (IGF-1) receptor are nontumorigenic and induce regression of wild-type tumors.Cancer Res. Apr. 15, 1994;54(8):2218-22.

Noble et al., Gemcitabine. A review of its pharmacology and clinical potential in non-small cell lung cancer and pancreatic cancer. Drugs. Sep. 1997;54(3):447-72.

Yeo et al., YC-1: a potential anticancer drug targeting hypoxia-inducible factor; J. Natl Cancer Inst. Apr. 2, 2003;95(7):516-25.

Pollak et al., Insulin-like growth factors and neoplasia; Nat Rev Cancer. Jul. 2004;4(7):505-518.

Leventhal et al., Insulin-like growth factor-II as a paracrine growth factor in human neuroblastoma cells, Exp Cell Res. Nov. 1995;221(1):179-86.

Shepard et al., "Monoclonal Antibodies: A Practical Approach", 2000, Oxford University Press, pp. 58-66.

Lebon et al., Purification of insulin-like growth factor I receptor from human placental membranes. J Biol Chem. Jun. 15, 1986;261(17):7685-9.

Hailey et al., Neutralizing anti-insulin-like growth factor receptor 1 antibodies inhibit receptor function and induce receptor degradation in tumor cells. Mol. Cancer Therap. 1:1349-1353 (2002).

Bagatell et al., Hsp90 inhibitors deplete key anti-apoptotic proteins in pediatric solid tumor cells and demonstrate synergistic anticancer activity with cisplatin. Int J Cancer. Jan. 10, 2005;113(2):179-88.

Baserga, Targeting the IGF-1 receptor: from rags to riches. Eur. J. Cancer. Sep. 2004;40(14):2013-5.

Garcia-Echeverria et al., In vivo antitumor activity of NVP-AEW541—A novel, potent, and selective inhibitor of the IGF-IR kinase. Cancer Cell. Mar. 2004;5(3):231-9.

Maurer et al., Opiate antagonistic properties of an octapeptide somatostatin analog. Proc Natl Acad Sci U S A. Aug. 1982;79(15):4815-7.

Ciardiello et al., A novel approach in the treatment of cancer: targeting the epidermal growth factor receptor. Clin Cancer Res. Oct. 2001;7(10):2958-70. Review.

Stamos et al., Structure of the epidermal growth factor receptor kinase domain alone and in complex with a 4-anilinoquinazoline inhibitor. J Biol Chem. Nov. 29, 2002;277(48):46265-72.

Baselga, The EGFR as a target for anticancer therapy—focus on cetuximab. Eur J Cancer. Sep. 2001;37 Suppl 4:S16-22.

Hidalgo et al., The rapamycin-sensitive signal transduction pathway as a target for cancer therapy. Oncogene. Dec. 27, 2000;19(56):6680-6.

Liu et al., Antitumor activity of SCH 66336, an orally bioavailable tricyclic inhibitor of farnesyl protein transferase, in human tumor xenograft models and wap-ras transgenic mice. Cancer Res. Nov. 1, 1998;58(21):4947-56.

Siegel-Lakhai et al., Phase I Pharmacokinetic Study of the Safety and Tolerability of Lapatinib (GW572016) in Combination with Oxaliplatin/Fluorouracil/Leucovorin (FOLFOX4) in Patients with Solid Tumors. Clin Cancer Res. Aug. 1, 2007;13(15):4495-502.

Hidalgo et al., A phase I and pharmacokinetic study of temsirolimus (CCI-779) administered intravenously daily for 5 days every 2 weeks to patients with advanced cancer. Clin Cancer Res. Oct. 1, 2006;12(19):5755-63.

Taylor et al., Estrogen receptor-mediated and cytotoxic effects of the antiestrogens tamoxifen and 4-hydroxytamoxifen. Cancer Research (1984) 44: 1409-1414.

\* cited by examiner

ANTI-IGFR1 ANTIBODY THERAPEUTIC COMBINATIONS

This application claims the benefit of U.S. Provisional Patent Application No. 60/524,732; filed Nov. 21, 2003 which is herein incorporated by reference in its entirety.

FIELD OF THE INVENTION

The present invention relates to therapeutic combinations comprising one or more anti-IGFR1 antibodies and one or more chemotherapeutic agents.

BACKGROUND OF THE INVENTION

The insulin-like growth factors, also known as somatomedins, include insulin-like growth factor-I (IGF-I) and insulin-like growth factor-II (IGF-II) (Klapper, et al., (1983) Endocrinol. 112:2215 and Rinderknecht, et al., (1978) Febs. Lett. 89:283). These growth factors exert mitogenic activity on various cell types, including tumor cells (Macaulay, (1992) Br. J. Cancer 65:311), by binding to a common receptor named the insulin-like growth factor receptor-1 (IGFR1) (Sepp-Lorenzino, (1998) Breast Cancer Research and Treatment 47:235). Interaction of IGFs with IGFR1 activates the receptor by triggering autophosphorylation of the receptor on tyrosine residues (Butler, et al., (1998) Comparative Biochemistry and Physiology 121:19). Once activated, IGFR1, in turn, phosphorylates intracellular targets to activate cellular signaling pathways. This receptor activation is critical for stimulation of tumor cell growth and survival. Therefore, inhibition of IGFR1 activity represents a valuable potential method to treat or prevent growth of human cancers and other proliferative diseases.

Several lines of evidence indicate that IGF-I, IGF-II and their receptor IGFR1 are important mediators of the malignant phenotype. Plasma levels of IGF-I have been found to be the strongest predictor of prostate cancer risk (Chan, et al., (1998) Science 279:563) and similar epidemiological studies strongly link plasma IGF-I levels with breast, colon and lung cancer risk.

Overexpression of Insulin-like Growth Factor Receptor-I has also been demonstrated in several cancer cell lines and tumor tissues. IGFR1 is overexpressed in 40% of all breast cancer cell lines (Pandini, et al., (1999) Cancer Res. 5:1935) and in 15% of lung cancer cell lines. In breast cancer tumor tissue, IGFR1 is overexpressed 6-14 fold and IGFR1 exhibits 2-4 fold higher kinase activity as compared to normal tissue (Webster, et al., (1996) Cancer Res. 56:2781 and Pekonen, et al., (1998) Cancer Res. 48:1343). Moreover, colorectal cancer tissue has been reported to exhibit strongly elevated IGFR1 levels (Weber et al., Cancer 95(10):2086-95(2002)). Analysis of primary cervical cancer cell cultures and cervical cancer cell lines revealed 3- and 5-fold overexpression of IGFR1, respectively, as compared to normal ectocervical cells (Steller, et al., (1996) Cancer Res. 56:1762). Expression of IGFR1 in synovial sarcoma cells also correlated with an aggressive phenotype (i.e., metastasis and high rate of proliferation; Xie, et al., (1999) Cancer Res. 59:3588).

Acromegaly, a slowly developing disease, is caused by hypersecretion of growth hormone and IGF-I (Ben-Schlomo, et al., (2001) Endocrin. Metab. Clin. North. Am. 30:565-583). Antagonism of IGFR1 function is helpful in treating the disease.

There are several antibodies, which are known in the art, which inhibit the activity of IGFR1. However, these are of relatively low therapeutic value. For example, α-IR3 (Kull, et al., (1983) J. Biol. Chem. 258:6561), 1H7 (Li et al., (1993) Biochem. Biophys. Res. Comm. 196.92-98 and Xiong et al., (1992) Proc. Natl. Acad. Sci., U.S.A. 89:5356-5360; Santa Cruz biotechnology, Inc.; Santa Cruz, Calif.) and MAB391 (R&D Systems; Minneapolis, Minn.) are mouse monoclonal antibodies which interact with IGFR1 and inhibit its activity. Since these are mouse antibodies, their therapeutic utility in humans is limited. When an immunocompetent human subject is administered a dose of a murine antibody, the subject produces antibodies against the mouse immunoglobulin sequences. These human anti-mouse antibodies (HAMA) neutralize the therapeutic antibodies and may induce acute toxicity (i.e., a HAMA response).

One method by which to avert a HAMA response is through the use of fully human antibodies which lack any foreign (e.g., mouse) amino acid sequences. Although the use of fully-human antibodies is an effective method by which to reduce or prevent human host immune rejection of the therapeutic antibody, rejection of the fully-human antibody can occur. Human rejection of human antibodies may be referred to as a human anti-human antibody response (HAHA response). HAHA response can be mediated by factors such as the presence of rare, low occurrence amino acid sequences in the fully-human antibodies. For this reason, therapeutic antibodies can also be optimized by the inclusion of non-immunogenic or only weakly immunogenic human antibody framework sequences. Preferably, the sequences occur frequently in other human antibodies.

Although anti-IGFR1 antibodies are an effective means by which to treat medical conditions mediated by the receptor (e.g., cancer or acromegaly), the efficacy of such treatments would be enhanced by use of one or more additional chemotherapeutic agents. For example, an anti-IGFR1 antibody can be administered to a subject in association with a second anti-IGFR1 antibody or a small molecule IGFR1 antagonist. The present invention provides, inter alia, such treatments and compositions for use in the treatments.

SUMMARY OF THE INVENTION

The present invention provides a combination comprising (a) one or more binding compositions, such as any anti-IGFR1 antibody, preferably an isolated fully-human monoclonal antibody, preferably comprising a member selected from the group consisting of: (i) a light chain amino acid sequence which comprises CDR-L1 defined by SEQ ID NO: 5, CDR-L2 defined by SEQ ID NO: 6 and CDR-L3 defined by SEQ ID NO: 7; and (ii) a heavy chain amino acid sequence which comprises CDR-H1 defined by SEQ ID NO: 8, CDR-H2 defined by SEQ ID NO: 9 and CDR-H3 defined by SEQ ID NO: 10; in association with (b) one or more chemotherapeutic agents and, optionally, a pharmaceutically acceptable carrier.

In one embodiment, a binding composition (e.g., an isolated fully-human monoclonal antibody) comprises a light chain amino acid sequence which comprises CDR-L1 defined by SEQ ID NO: 5, CDR-L2 defined by SEQ ID NO: 6 and CDR-L3 defined by SEQ ID NO: 7; and a heavy chain amino acid sequence which comprises CDR-H1 defined by SEQ ID NO: 8, CDR-H2 defined by SEQ ID NO: 9 and CDR-H3 defined by SEQ ID NO: 10. In an embodiment, a binding composition comprises a light chain immunoglobulin comprising mature LCF (amino acids 20-128 of SEQ ID NO: 2) and a heavy chain immunoglobulin comprising mature HCA (amino acids 20-137 of SEQ ID NO: 4).

A binding composition can be any binding composition (e.g., an isolated fully-human monoclonal antibody) set forth in U.S. patent application Ser. No. 10/443,466, filed May 22, 2003.

A chemotherapeutic agent can be one or more members selected from the group consisting of a taxane, a topoisomerase inhibitor, a signal transduction inhibitor, a cell cycle inhibitor, an IGF/IGFR1 system modulator, a farnesyl protein transferase (FPT) inhibitor, an epidermal growth factor receptor (EGFR) inhibitor, a HER2 inhibitor, a vascular epidermal growth factor (VEGF) receptor inhibitor, a mitogen activated protein (MAP) kinase inhibitor, a MEK inhibitor, an AKT inhibitor, a, mTOR inhibitor, a pI3 kinase inhibitor, a Raf inhibitor, a cyclin dependent kinase (CDK) inhibitor, a microtubule stabilizer, a microtubule inhibitor, a SERM/Antiestrogen, an aromatase inhibitor, an anthracycline, a proteasome inhibitor, an agent which inhibits insulin-like growth factor (IGF) production and/or an anti-sense inhibitor of IGFR1, IGF-1 or IGF2.

A taxane can be, for example, paclitaxel or docetaxel. A microtubule inhibitor can be, for example, vincristine, vinblastine, a podophyllotoxin, epothilone B, BMS-247550 or BMS-310705. An epidermal growth factor receptor (EGFR) inhibitor can be, for example, gefitinib, erlotinib, cetuximab, ABX-EGF, lapatanib, canertinib, EKB-569 or PKI-166. A farnesyl protein transferase inhibitor can be, for example, lonafarnib or tipifarnib (R155777). A selective estrogen receptor modulator (SERM)/antiestrogen can be, for example, tamoxifen, raloxifene, fulvestrant, acolbifene, pipendoxifene, arzoxifene, toremifene, lasofoxifene, bazedoxifene (TSE-424), idoxifene, HMR-3339 and ZK-186619. An anthracycline can be doxorubicin, daunorubicin or epirubicin. A HER2 inhibitor can be, for example, trastuzumab, HKI-272, CP-724714 or TAK-165. A topoisomerase inhibitor can be, for example, etoposide, topotecan, camptothecin or irinotecan.

In one embodiment, the present invention comprises a combination comprising: (a) one or more binding compositions (e.g., an isolated fully-human monoclonal antibody) comprising a light chain immunoglobulin comprising amino acids 20-128 of SEQ ID NO: 2 and a heavy chain immunoglobulin comprising amino acids 20-137 of SEQ ID NO: 4; in association with (b) one or more chemotherapeutic agents selected from:

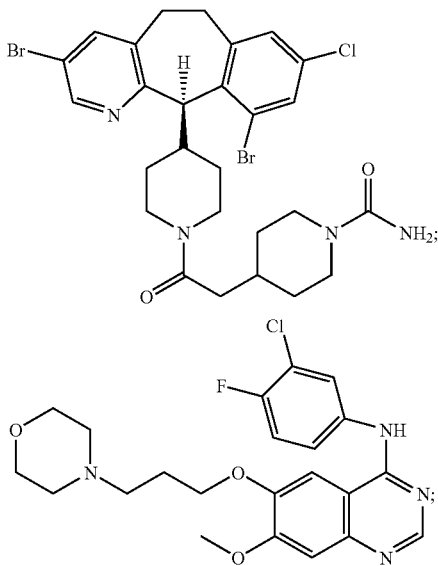

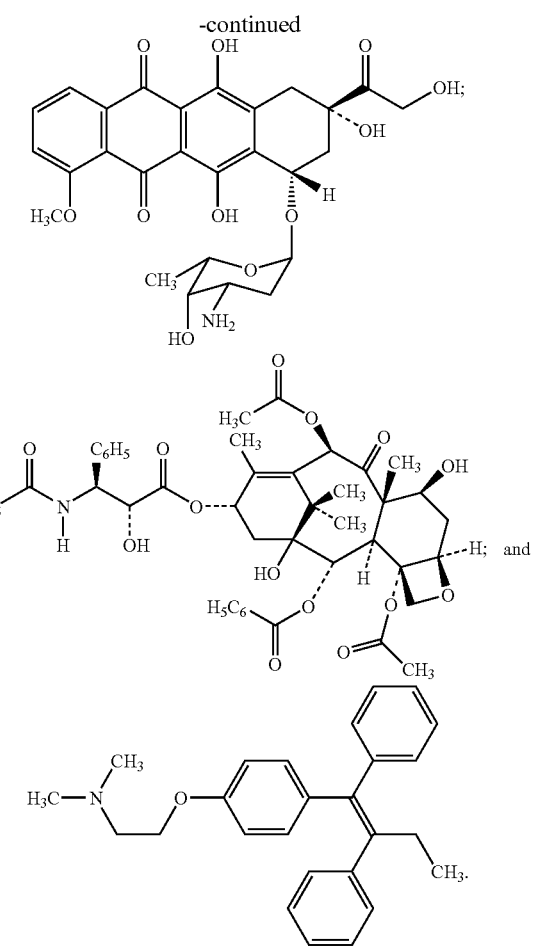

Also provided by the present invention is a method for treating or preventing a medical condition in a subject, which medical condition is mediated by elevated expression or activity of Insulin-like Growth Factor Receptor-I, comprising administering (e.g., by a parenteral or non-parenteral route), to the subject, a composition comprising a therapeutically effective amount of (a) one or more binding compositions (e.g., an isolated fully-human monoclonal antibody), such as any anti-IGFR1 antibody, preferably comprising a member selected from the group consisting of: (i) a light chain amino acid sequence which comprises CDR-L1 defined by SEQ ID NO: 5, CDR-L2 defined by SEQ ID NO: 6 and CDR-L3 defined by SEQ ID NO: 7; and (ii) a heavy chain amino acid sequence which comprises CDR-H1 defined by SEQ ID NO: 8, CDR-H2 defined by SEQ ID NO: 9 and CDR-H3 defined by SEQ ID NO: 10; optionally in association with (b) a therapeutically effective amount of one or more chemotherapeutic agents and, optionally, a pharmaceutically acceptable carrier. In an embodiment of the invention, the medical condition is treated with a therapeutically effective amount of any isolated anti-IGFR antibody or antigen binding fragment thereof of the invention alone.

In one embodiment, the binding composition (e.g., an isolated fully-human monoclonal antibody) comprises a light chain immunoglobulin comprising amino acids 20-128 of SEQ ID NO: 2 and a heavy chain immunoglobulin comprising amino acids of 20-137 of SEQ ID NO: 4. In one embodiment, a chemotherapeutic agent is one or more members selected from the group consisting of:

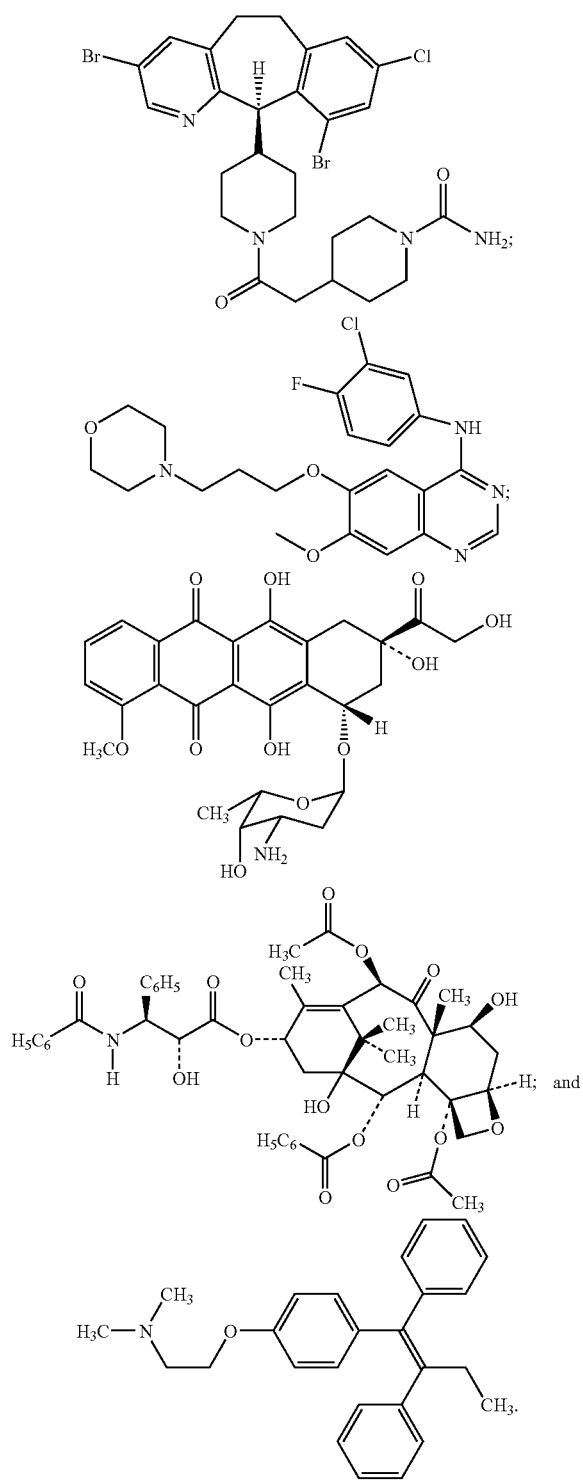

associated with metastatic carcinoid, vasoactive intestinal peptide secreting tumors, gigantism, psoriasis, atherosclerosis, smooth muscle restenosis of blood vessels and inappropriate microvascular proliferation.

An embodiment of the present invention includes a method for treating or preventing a medical condition in a subject (e.g., rheumatoid arthritis, Grave's disease, multiple sclerosis, systemic lupus erythematosus, Hashimoto's Thyroiditis, Myasthenia Gravis, auto-immune thyroiditis, Bechet's disease, acromegaly, bladder cancer, Wilm's cancer, ovarian cancer, pancreatic cancer, benign prostatic hyperplasia, breast cancer, prostate cancer, bone cancer, lung cancer, colorectal cancer, cervical cancer, synovial sarcoma, diarrhea associated with metastatic carcinoid, vasoactive intestinal peptide secreting tumors, gigantism, psoriasis, atherosclerosis, smooth muscle restenosis of blood vessels or inappropriate microvascular proliferation) comprising administering a combination comprising: (a) a therapeutically effective amount of one or more binding compositions (e.g., an isolated fully-human monoclonal antibody) comprising a light chain immunoglobulin comprising amino acids 20-128 of SEQ ID NO: 2 and a heavy chain immunoglobulin comprising amino acids 20-137 of SEQ ID NO: 4; in association with (b) a therapeutically effective amount of one or more chemotherapeutic agents selected from:

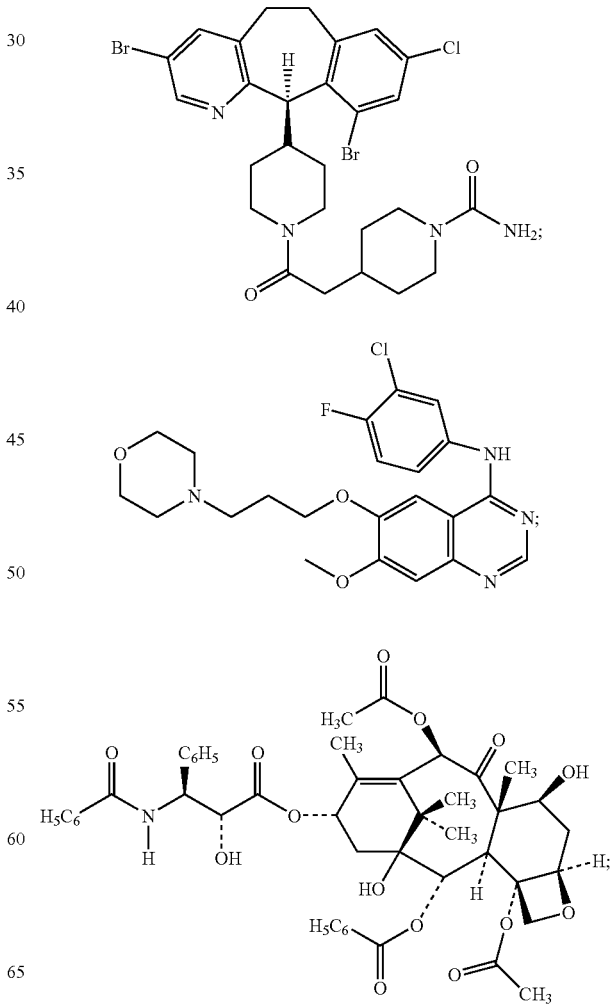

In one embodiment, the medical condition treated by a method of the present invention is selected from the group consisting of Rheumatoid Arthritis, Grave's disease, Multiple Sclerosis, Systemic Lupus Erythematosus, Hashimoto's Thyroiditis, Myasthenia Gravis, Auto-immune Thyroiditis, Bechet's disease, acromegaly, bladder cancer, Wilm's cancer, ovarian cancer, pancreatic cancer, benign prostatic hyperplasia, breast cancer, prostate cancer, bone cancer, lung cancer, colorectal cancer, cervical cancer, synovial sarcoma, diarrhea

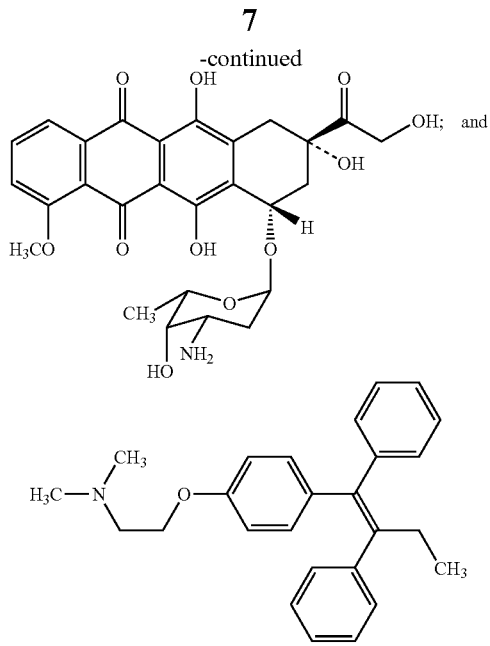

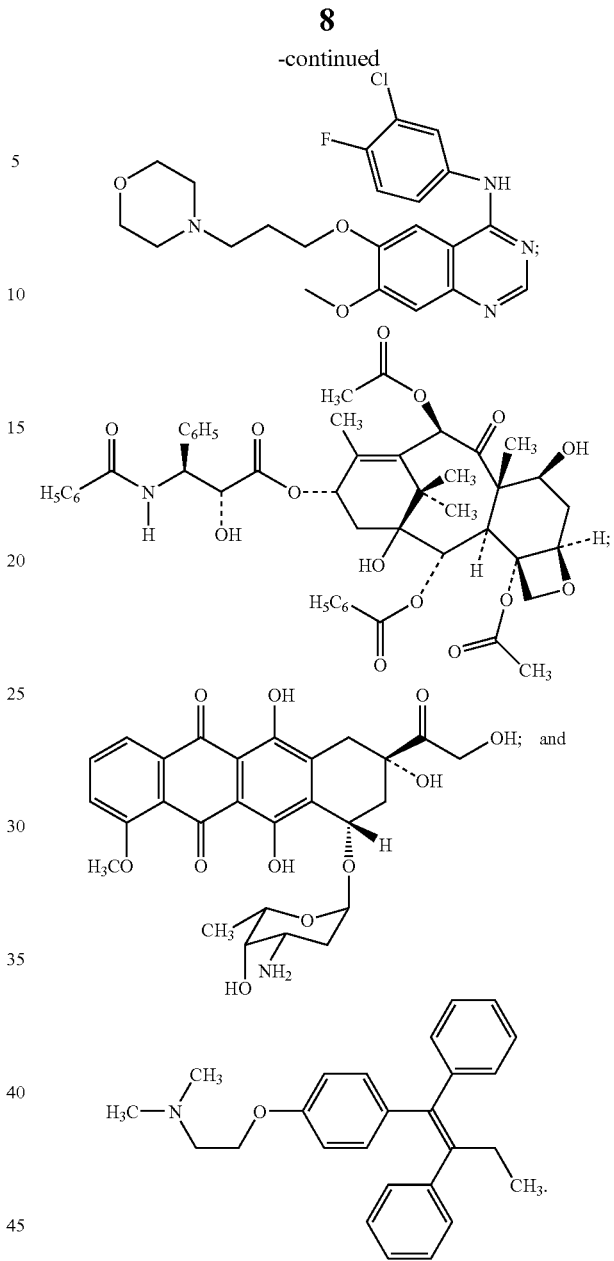

to the subject.

Also provided by the present invention is a method for inhibiting the growth or proliferation of any cell (e.g., a cell in vitro or a cell in vivo (e.g., in the body of a subject)), for example a malignant cell, including, but not limited to, an NCI-H322 cell, an A2780 cell, an MCF7 cell, a non-small cell carcinoma lung cancer cell, a breast cancer cell, an ovarian cancer cell, a colorectal cancer cell, a prostate cancer cell, a pediatric cancer or a pancreatic cancer cell, comprising contacting the cell with a combination comprising (a) one or more binding compositions, such as any isolated anti-IGFR1 antibody, preferably an isolated fully-human monoclonal antibody, preferably comprising a member selected from the group consisting of: (i) a light chain amino acid sequence which comprises CDR-L1 defined by SEQ ID NO: 5, CDR-L2 defined by SEQ ID NO: 6 and CDR-L3 defined by SEQ ID NO: 7; and (ii) a heavy chain amino acid sequence which comprises CDR-HL defined by SEQ ID NO: 8, CDR-H2 defined by SEQ ID NO: 9 and CDR-H3 defined by SEQ ID NO: 10; in association with (b) one or more chemotherapeutic agents and, optionally, a pharmaceutically acceptable carrier. In one embodiment, a binding composition comprises a light chain immunoglobulin comprising amino acids 20-128 of SEQ ID NO: 2 and a heavy chain immunoglobulin comprising amino acids of 20-137 of SEQ ID NO: 4. In one embodiment, a chemotherapeutic agent is one or more members selected from the group consisting of:

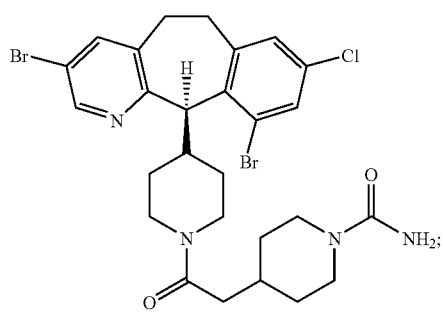

The present invention also provides a kit comprising (a) one or more binding compositions (e.g., an isolated fully-human monoclonal antibody) comprising a member selected from the group consisting of: a light chain amino acid sequence which comprises CDR-L1 defined by SEQ ID NO: 5, CDR-L2 defined by SEQ ID NO: 6 and CDR-L3 defined by SEQ ID NO: 7; and a heavy chain amino acid sequence which comprises CDR-HL defined by SEQ ID NO: 8 or 12, CDR-H2 defined by SEQ ID NO: 9 and CDR-H3 defined by SEQ ID NO: 10; in association with (b) one or more chemotherapeutic agents. The binding composition can be in a separate container from the chemotherapeutic agent.

DETAILED DESCRIPTION OF THE INVENTION

The present invention provides combinations and methods for treating medical conditions that are characterized by a high level of IGFR1 expression, ligand binding or activity or a high level of IGF-1 or IGF-2, such as cancer. The combinations of the invention, which can be used to treat the medical conditions, include one or more anti-IGFR1 antibodies (e.g., an isolated fully-human monoclonal antibody) in association with one or more chemotherapeutic agents.

The combinations of the invention include the binding composition component and chemotherapeutic agent component "in association" with one another. The term "in association" indicates that the components of the combinations of the invention can be formulated into a single composition for simultaneous delivery or formulated separately into two or more compositions (e.g., a kit). Furthermore, each component of a combination of the invention can be administered to a subject at a different time than when the other component is administered; for example, each administration may be given non-simultaneously at several intervals over a given period of time. Moreover, the separate components may be administered to a subject by the same or by a different route (e.g., orally, intravenously, intratumorally).

The compositions of the invention provide a particularly effective means for treating diseases mediated by IGFR1, IGF-1 and/or IGF-2. The therapeutic efficacy of both the binding composition of the invention and the chemotherapeutic agent(s), when administered in association, is far superior to that of either component alone.

The present invention includes any isolated nucleic acid or isolated polypeptide (e.g., an isolated fully-human monoclonal antibody) which comprises one or more (e.g., 1, 2, 3, 4, 5, 6, 7 or 8) of any of the nucleic acids or polypeptides (including mature fragments thereof) set forth, below, in Table 1.

TABLE 1

Summary of amino acid and nucleotide sequences of the invention.

| Sequence | Sequence Identifier |
|---|---|
| 19D12/15H12 light chain F (LCF) variable region polynucleotide sequence | SEQ ID NO: 1 |
| 19D12/15H12 light chain F variable region polypeptide sequence | SEQ ID NO: 2 |
| 19D12/15H12 heavy chain A (HCA) variable region polynucleotide sequence | SEQ ID NO: 3 |
| 19D12/15H12 heavy chain A variable region polypeptide sequence | SEQ ID NO: 4 |
| 19D12/15H12 light chain F CDR-L1 polypeptide sequence | SEQ ID NO: 5 |
| 19D12/15H12 light chain F CDR-L2 polypeptide sequence | SEQ ID NO: 6 |
| 19D12/15H12 light chain F CDR-L3 polypeptide sequence | SEQ ID NO: 7 |
| 19D12/15H12 heavy chain A CDR-H1 polypeptide sequence | SEQ ID NO: 8 |
| 19D12/15H12 heavy chain A CDR-H2 polypeptide sequence | SEQ ID NO: 9 |
| 19D12/15H12 heavy chain A CDR-H3 polypeptide sequence | SEQ ID NO: 10 |
| Amino acid sequence of Insulin-like Growth Factor Receptor-I (IGFR1) | SEQ ID NO: 11 |

TABLE 1-continued

Summary of amino acid and nucleotide sequences of the invention.

| Sequence | Sequence Identifier |
|---|---|
| Alternative 19D12/15H12 heavy chain A CDR-H1 polypeptide sequence | SEQ ID NO: 12 |
| 19D12/15H12 light chain polypeptide sequence | SEQ ID NO: 13 |
| 19D12/15H12 heavy chain polypeptide sequence | SEQ ID NO: 14 |

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

A "polynucleotide", "nucleic acid" or "nucleic acid molecule" may refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in single stranded form, double-stranded form or otherwise.

A "polynucleotide sequence", "nucleic acid sequence" or "nucleotide sequence" is a series of nucleotide bases (also called "nucleotides") in a nucleic acid, such as DNA or RNA, and means any chain of two or more nucleotides.

A "coding sequence" or a sequence "encoding" an expression product, such as a RNA, polypeptide, protein, or enzyme, is a nucleotide sequence that, when expressed, results in production of the product.

The term "gene" means a DNA sequence that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

"Amplification" of DNA as used herein may denote the use of polymerase chain reaction (PCR) to increase the concentration of a particular DNA sequence within a mixture of DNA sequences. For a description of PCR see Saiki, et al., *Science* (1988) 239: 487. In a specific embodiment, the present invention includes a nucleic acid, which encodes an anti-IGFR1 antibody, an anti-IGFR1 antibody heavy or light chain, an anti-IGFR1 antibody heavy or light chain variable region, an anti-IGFR1 antibody heavy or light chain constant region or anti-IGFR1 antibody CDR (e.g., CDR-L1, CDR-L2, CDR-L3, CDR-H1, CDR-H2 or CDR-H3) which can be amplified by PCR.

As used herein, the term "oligonucleotide" refers to a nucleic acid, generally of at least 10 (e.g., 10, 11, 12, 13 or 14), preferably at least 15 (e.g., 15, 16, 17, 18 or 19), and more preferably at least 20 nucleotides (e.g., 20, 21, 22, 23, 24, 25, 26, 27, 28, 29 or 30), preferably no more than 100 nucleotides (e.g., 40, 50, 60, 70, 80 or 90), that may be hybridizable to a genomic DNA molecule, a cDNA molecule, or an mRNA molecule encoding a gene, mRNA, cDNA, or other nucleic acid of interest. Oligonucleotides can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, preferably on a nucleic acid synthesizer.

The sequence of any nucleic acid (e.g., a nucleic acid encoding an IGFR1 gene or a nucleic acid encoding an anti-IGFR1 antibody or a fragment or portion thereof) may be determined by any method known in the art (e.g., chemical sequencing or enzymatic sequencing). "Chemical sequencing" of DNA may denote methods such as that of Maxam and Gilbert (1977) (Proc. Natl. Acad. Sci. USA 74:560), in which DNA is randomly cleaved using individual base-specific reactions. "Enzymatic sequencing" of DNA may denote methods such as that of Sanger (Sanger, et al., (1977) Proc. Natl. Acad. Sci. USA 74:5463).

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

A "promoter" or "promoter sequence" is a DNA regulatory region capable of binding an RNA polymerase in a cell (e.g., directly or through other promoter-bound proteins or substances) and initiating transcription of a coding sequence (e.g., LCF or HCA). A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the β-lactamase promoter (Villa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

A coding sequence is "under the control of", "functionally associated with" or "operably associated with" transcriptional and translational control sequences in a cell when the sequences direct RNA polymerase mediated transcription of the coding sequence into RNA, preferably mRNA, which then may be trans-RNA spliced (if it contains introns) and, optionally, translated into a protein encoded by the coding sequence.

The terms "express" and "expression" mean allowing or causing the information in a gene, RNA or DNA sequence to become manifest; for example, producing a protein by activating the cellular functions involved in transcription and translation of a corresponding gene. A DNA sequence is expressed in or by a cell to form an "expression product" such as an RNA (e.g., mRNA) or a protein. The expression product itself may also be said to be "expressed" by the cell.

The terms "vector", "cloning vector" and "expression vector" mean the vehicle (e.g., a plasmid) by which a DNA or RNA sequence can be introduced into a host cell, so as to transform the host and, optionally, promote expression and/or replication of the introduced sequence.

The term "transfection" or "transformation" means the introduction of a nucleic acid into a cell. These terms may refer to the introduction of a nucleic acid encoding an anti-IGFR1 antibody or fragment thereof into a cell. The introduced gene or sequence may be called a "clone". A host cell that receives the introduced DNA or RNA has been "transformed" and is a "transformant" or a "clone". The DNA or RNA introduced to a host cell can come from any source, including cells of the same genus or species as the host cell, or cells of a different genus or species.

The term "host cell" means any cell of any organism that is selected, modified, transfected, transformed, grown, or used or manipulated in any way, for the production of a substance by the cell, for example the expression or replication, by the cell, of a gene, a DNA or RNA sequence, a protein or an enzyme.

The term "expression system" means a host cell and compatible vector which, under suitable conditions, can express a protein or nucleic acid which is carried by the vector and introduced to the host cell. Common expression systems include E. coli host cells and plasmid vectors, insect host cells and Baculovirus vectors, and mammalian host cells and vectors. In a specific embodiment, IGFR1 or an antibody and antigen-binding fragment of the invention may be expressed in human embryonic kidney cells (HEK293). Other suitable cells include CHO (chinese hamster ovary) cells, HeLa cells and NIH 3T3 cells and NSO cells (non-Ig-producing murine myeloma cell line). Nucleic acids encoding an antibody or antigen-binding fragment of the invention, sIGFR1 (see infra) or IGFR1 may be expressed at high levels in an E. coli/T7 expression system as disclosed in U.S. Pat. Nos. 4,952,496, 5,693,489 and 5,869,320 and in Davanloo, P., et al., (1984) Proc. Natl. Acad. Sci. USA 81, 2035-2039; Studier, F. W., et al., (1986) J. Mol. Biol. 189: 113-130; Rosenberg, A. H., et al., (1987) Gene 56: 125-135; and Dunn, J. J., et al., (1988) Gene 68: 259 which are herein incorporated by reference.

The present invention contemplates any superficial or slight modification to the amino acid or nucleotide sequences which correspond to the antibodies or antigen-binding fragments of the invention. In particular, the present invention contemplates sequence conservative variants of the nucleic acids which encode the antibodies or antigen-binding fragments of the invention. "Sequence-conservative variants" of a polynucleotide sequence are those in which a change of one or more nucleotides in a given codon results in no alteration in the amino acid encoded at that position. Function-conservative variants of the antibodies of the invention are also contemplated by the present invention. "Function-conservative variants" are those in which one or more amino acid residues in a protein or enzyme have been changed without altering the overall conformation and function of the polypeptide, including, but, by no means, limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, proline, tyrosine, phenylalanine, tryptophan and methionine; acidic amino acids which may be interchangeable include aspartic acid and glutamic acid and basic amino acids which may be interchangeable include histidine, lysine and arginine.

The present invention includes anti-IGFR1 antibodies and fragments thereof which are encoded by nucleic acids as described in Table 1 as well as nucleic acids which hybridize thereto. Preferably, the nucleic acids hybridize under low stringency conditions, more preferably under moderate stringency conditions and most preferably under high stringency conditions and, preferably, exhibit IGFR1 binding activity. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., supra). The conditions of temperature and ionic strength determine the "stringency" of the hybridization. Typical low stringency hybridization conditions include 55° C., 5×SSC, 0.1% SDS and no formamide; or 30% formamide, 5×SSC, 0.5% SDS at 42° C. Typical, moderate stringency hybridization conditions are similar to the low stringency conditions except the hybridization is carried out in 40% formamide, with 5× or 6×SSC and 0.1% SDS at 42° C. High stringency hybridization conditions are similar to low stringency conditions except the hybridization conditions are carried out in 50% formamide, 5× or 6×SSC at 42° C. or, optionally, at a higher temperature (e.g., 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, i.e., oligonucleotides, the position of mismatches becomes more important, and the length of the oligonucleotide determines its specificity (see Sambrook, et al., supra, 11.7-11.8).

Also included in the present invention are nucleic acids comprising nucleotide sequences and polypeptides comprising amino acid sequences which are at least about 70% identical, preferably at least about 80% identical, more preferably at least about 90% identical and most preferably at least about 95% identical (e.g., 95%, 96%, 97%, 98%, 99%, 100%) to the reference nucleotide and amino acid sequences of Table 1 when the comparison is performed by a BLAST algorithm wherein the parameters of the algorithm are selected to give the largest match between the respective sequences over the entire length of the respective reference sequences. Polypeptides comprising amino acid sequences which are at least about 70% similar, preferably at least about 80% similar, more preferably at least about 90% similar and most preferably at least about 95% similar (e.g., 95%, 96%, 97%, 98%, 99%, 100%) to any of the reference amino acid sequences of Table 1 when the comparison is performed with a BLAST algorithm wherein the parameters of the algorithm are selected to give the largest match between the respective sequences over the entire length of the respective reference sequences, are also included in the present invention.

Sequence identity refers to exact matches between the nucleotides or amino acids of two sequences which are being compared. Sequence similarity refers to both exact matches between the amino acids of two polypeptides which are being compared in addition to matches between nonidentical, biochemically related amino acids. Biochemically related amino acids which share similar properties and may be interchangeable are discussed above.

The following references regarding the BLAST algorithm are herein incorporated by reference: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in *Atlas of Protein Sequence and Structure*, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in *Atlas of Protein Sequence and Structure*, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, N.Y.

Antibody Structure

In general, the basic antibody structural unit is known to comprise a tetramer. Each tetramer includes two identical pairs of polypeptide chains, each pair having one "light" (about 25 kDa) and one "heavy" chain (about 50-70 kDa). The amino-terminal portion of each chain may include a variable region of about 100 to 110 or more amino acids primarily responsible for antigen recognition. The carboxy-terminal portion of each chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)) (incorporated by reference in its entirety for all purposes).

The variable regions of each light/heavy chain pair form the antibody binding site. Thus, in general, an intact IgG antibody has two binding sites. Except in bifunctional or bispecific antibodies, the two binding sites are, in general, the same.

Normally, the chains all exhibit the same general structure of relatively conserved framework regions (FR) joined by three hypervariable regions, also called complementarity determining regions or CDRs. The CDRs from the two chains of each pair are usually aligned by the framework regions, enabling binding to a specific epitope. In general, from N-terminal to C-terminal, both light and heavy chains comprise the domains FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J. Mol. Biol. 196:901-917 or Chothia, et al., (1989) Nature 342:878-883.

Binding Compositions

The binding compositions of the combinations of the present invention include any composition which binds specifically to IGFR1. A binding composition or agent refers to a molecule that binds with specificity to IGFR1, e.g., in a ligand-receptor type fashion or an antibody-antigen interaction, e.g., proteins which specifically associate with IGFR1, e.g., in a natural physiologically relevant protein-protein interaction, either covalent or non-covalent. The term "binding composition" includes small organic molecules, nucleic acids and polypeptides, such as a full antibody (preferably an isolated monoclonal human antibody) or antigen-binding fragment thereof of the present invention (e.g., antibody 19D12/15H12, antibody 19D12/15H12 LCF/HCA or any peptide set forth, above, in Table 1).

Antibodies and antigen binding fragments thereof, include, but are not limited to, monoclonal antibodies, polyclonal antibodies, bispecific antibodies, Fab antibody fragments, F(ab)$_2$ antibody fragments, Fv antibody fragments (e.g., V$_H$ or V$_L$), single chain Fv antibody fragments and dsFv antibody fragments. Furthermore, antibodies of the invention may be fully human antibodies or chimeric antibodies.

The combinations of the present invention include any antibody or antigen binding fragment thereof or any polynucleotide encoding such antibody or antigen-binding fragment thereof as set forth in U.S. patent application Ser. No. 10/443,466, filed May 22, 2003 and in WO 03/100008. Preferably, the antibody molecules are isolated monoclonal, fully human antibodies. Preferably the antibodies of the invention comprise one or more, more preferably all 6 CDRs comprising an amino acid sequence set forth in any one of SEQ ID NOs: 5-10. Preferably, an antibody of the invention includes mature 19D12/15H12 light chain F (LCF) (see SEQ ID NO: 2) paired with mature 19D12/15H12 heavy chain A (HCA) (see SEQ ID NO: 4) (e.g., the monoclonal, fully-human antibody 19D12/15H12 LCF/HCA).

The amino acid and nucleotide sequences of preferred antibody chains are shown below. Dotted, underscored type indicates the signal peptide. Solid underscored type indicates the CDRs. Plain type indicates the framework regions. In one embodiment, the antibody chains are mature fragments which lack the signal peptide.

```
19D12/15H12 Light Chain-F
ATG TCG CCA TCA CAA CTC ATT GGG TTT CTG CTG CTC TGG GTT CCA GCC TCC (LCF; SEQ ID NO: 1)

AGG GGT GAA ATT GTG CTG ACT CAG AGC CCA GGT ACC CTG TCT GTG TCT CCA

GGC GAG AGA GCC ACC CTC TCC TGC CGG GCC AGT CAG AGC ATT GGT AGT AGC

TTA CAC TGG TAC CAG CAG AAA CCA GGT CAG GCT CCA AGG CTT CTC ATC AAG

TAT GCA TCC CAG TCC CTC TCA GGG ATC CCC GAT AGG TTC AGT GGC AGT GGA

TCT GGG ACA GAT TTC ACC CTC ACC ATC AGT AGA CTG GAG CCT GAA GAT TTC

GCA GTG TAT TAC TGT CAT CAG AGT AGT CGT TTA CCT CAC ACT TTC GGC CAA

GGG ACC AAG GTG GAG ATC AAA CGT ACA

M   S   P   S   Q   L   I   G   F   L   L   L   W   V   P   A   S   (SEQ ID NO: 2)

R   G   E   I   V   L   T   Q   S   P   G   T   L   S   V   S   P

G   E   R   A   T   L   S   C   R   A   S   Q   S   I   G   S   S

L   H   W   Y   Q   Q   K   P   G   Q   A   P   R   L   L   I   K

Y   A   S   Q   S   L   S   G   I   P   D   R   F   S   G   S   G

S   G   T   D   F   T   L   T   I   S   R   L   E   P   E   D   F

A   V   Y   Y   C   H   Q   S   S   R   L   P   H   T   F   G   Q

G   T   K   V   E   I   K   R   T
```

-continued

19D12/15H12 heavy chain-A
<u>ATG GAG TTT GGG CTG AGC TGG GTT TTC CTT GTT GCT ATA TTA AAA GGT GTC</u>  (HCA; SEQ ID NO: 3)

<u>CAG TGT</u> GAG GTT CAG CTG GTG CAG TCT GGG GGA GGC TTG GTA AAG CCT GGG

GGG TCC CTG AGA CTC TCC TGT GCA GCC TCT GGA TTC ACC TTC AGT <u>AGC TTT</u>

<u>GCT ATG CAC</u> TGG GTT CGC CAG GCT CCA GGA AAA GGT CTG GAG TGG ATA TCA

<u>GTT ATT GAT ACT CGT GGT GCC ACA TAC TAT GCA GAC TCC GTG AAG GGC</u> CGA

TTC ACC ATC TCC AGA GAC AAT GCC AAG AAC TCC TTG TAT CTT CAA ATG AAC

AGC CTG AGA GCC GAG GAC ACT GCT GTG TAT TAC TGT GCA AGA <u>CTG GGG AAC</u>

<u>TTC TAC TAC GGT ATG GAC GTC</u> TGG GGC CAA GGG ACC ACG GTC ACC GTC TCC

TCA

<u>Met Glu Phe Gly Leu Ser Trp Val Phe Leu Val Ala Ile Leu Lys Gly Val</u>  (SEQ ID NO: 4)

<u>Gln Cys</u> Glu Val Gln Leu Val Gln Ser Gly Gly Gly Leu Val Lys Pro Gly

Gly Ser Leu Arg Leu Ser Cys Ala Ala Ser Gly Phe Thr Phe Ser <u>Ser Phe</u>

<u>Ala Met His</u> Trp Val Arg Gln Ala Pro Gly Lys Gly Leu Glu Trp Ile Ser

<u>Val Ile Asp Thr Arg Gly Ala Thr Tyr Tyr Ala Asp Ser Val Lys Gly</u> Arg

Phe Thr ILe Ser Arg Asp Asn Ala Lys Asn Ser Leu Tyr Leu Gln Met Asn

Ser Leu Arg Ala Glu Asp Thr Ala Val Tyr Tyr Cys Ala Arg <u>Leu Gly Asn</u>

<u>Phe Tyr Tyr Gly Met Asp Val</u> Trp Gly Gln Gly Thr Thr Val Thr Val Ser

Ser

Three plasmids comprising a CMV promoter operably linked to the 15H12/19D12 LCF (κ) (variable region sequence set forth in SEQ ID NOs: 1 and 2), to the 15H12/19D12 HCA (γ4) (variable region sequence set forth in SEQ ID NOs: 3 and 4) or to the 15H12/19D12 HCA (γ1) (variable region sequence set forth in SEQ ID NOs: 3 and 4) has been deposited at the American Type Culture Collection (ATCC); 10801 University Boulevard; Manassas, Va. 20110-2209 on May 21, 2003. The deposit name and the ATCC accession numbers for the plasmids are set forth below:
CMV promoter-15H12/19D12 HCA (γ4)—
  Deposit name: "15H12/19D12 HCA (γ4)";
  ATCC accession No.: PTA-5214;
CMV promoter-15H12/19D12 HCA (γ1)—
  Deposit name: "15H12/19D12 HCA (γ4)";
  ATCC accession No.: PTA-5216;
CMV promoter-15H12/19D12 LCF (κ)—
  Deposit name: "15H12/19D12 LCF (κ)";
  ATCC accession No.: PTA-5220.
All restrictions on access to the plasmids deposited in ATCC will be removed upon grant of a patent.

Each of the above-referenced plasmids constitutes part of the present invention. Further, the nucleic acid located within each expression cassette, along with the immunoglobulin variable region therein, along with the mature, processed version thereof (i.e., lacking the signal sequence), particularly, SEQ ID NO: 3, mature HCA (nucleotides 58-411 of SEQ ID NO: 3), SEQ ID NO: 1 or mature LCF (nucleotides 58-384 of SEQ ID NO: 1), optionally including an immunoglobulin constant region, along with any polypeptide encoded by any of the foregoing nucleic acids, including mature or unprocessed chains, optionally including an immunoglobulin constant region, is a part of the present invention. Moreover, any antibody or antigen-binding fragment thereof comprising one of the encoded polypeptides is part of the present invention.

The scope of the present invention includes antibody variable regions of the present invention (e.g., any variable region, mature or unprocessed, indicated in Table 1) linked to any immunoglobulin constant region. If a light chain variable region is linked to a constant region, preferably it is a κ chain. If a heavy chain variable region is linked to a constant region, preferably it is a γ1, γ2, γ3 or γ4 constant region, more preferably, γ1, γ2 or γ4 and even more preferably γ1 or γ4.

The anti-IGFR1 antibody molecules of the invention preferably recognize human IGFR1, preferably a soluble fragment of IGFR1 (i.e., sIGFR1) such as amino acids 30-902 or SEQ ID NO: 11; however, the present invention includes antibody molecules which recognize IGFR1 from different species, preferably mammals (e.g., mouse, rat, rabbit, sheep or dog).

The present invention also includes an anti-IGFR1 antibody (e.g., LCF/HCA) or antigen-binding fragments thereof which are complexed with IGFR1 or any fragment thereof (e.g., sIGFR1, such as amino acids 30-902 of SEQ ID NO: 11) or with any cell which is expressing IGFR1 or any portion or fragment thereof on the cell surface (e.g., HEK293 cells stably transformed with human IGFR1 or MCF7 (e.g., ATCC Cell Line No. HTB-22)). Such complexes may be made by contacting the antibody or antibody fragment with IGFR1 or the IGFR1 fragment.

In a preferred embodiment, fully-human monoclonal antibodies directed against IGFR1 are generated using transgenic mice carrying parts of the human immune system rather than the mouse system. These transgenic mice, which may be referred to, herein, as "HuMAb" mice, contain a human immunoglobulin gene miniloci that encodes unrearranged human heavy (μ and γ) and κ light chain immunoglobulin sequences, together with targeted mutations that inactivate the endogenous μ and κ chain loci (Lonberg, N., et al., (1994)

Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N., et al., (1994), supra; reviewed in Lonberg, N. (1994) Handbook of Experimental Pharmacology 113:49-101; Lonberg, N., et al., (1995) Intern. Rev. Immunol. 13:65-93, and Harding, F., et al., (1995) Ann. N.Y. Acad. Sci 764: 536-546). The preparation of HuMab mice is commonly known in the art and is described, for example, in Taylor, L., et al., (1992) Nucleic Acids Research 20:6287-6295; Chen, J., et al., (1993) International Immunology 5: 647-656; Tuaillon, et al., (1993) Proc. Natl. Acad. Sci USA 90:3720-3724; Choi, et al., (1993) Nature Genetics 4:117-123; Chen, J., et al., (1993) EMBO J. 12: 821-830; Tuaillon, et al., (1994) J. Immunol. 152:2912-2920; Lonberg, et al., (1994) Nature 368 (6474): 856-859; Lonberg, N. (1994) Handbook of Experimental Pharmacology 113:49-101; Taylor, L., et al., (1994) International Immunology 6: 579-591; Lonberg, N., et al., (1995) Intern. Rev. Immunol. Vol. 13: 65-93; Harding, F., et al., (1995) Ann. N.Y. Acad. Sci 764:536-546; Fishwild, D., et al., (1996) Nature Biotechnology 14: 845-851 and Harding, et al., (1995) Annals NY Acad. Sci. 764:536-546; the contents of all of which are hereby incorporated by reference in their entirety. See further, U.S. Pat. Nos. 5,545,806; 5,569,825; 5,625,126; 5,633,425; 5,789,650; 5,877,397; 5,661,016; 5,814,318; 5,874, 299; 5,770,429 and 5,545,807; and International Patent Application Publication Nos. WO 98/24884; WO 94/25585; WO 93/12227; WO 92/22645 and WO 92/03918 the disclosures of all of which are hereby incorporated by reference in their entity.

To generate fully human, monoclonal antibodies to IGFR1, HuMab mice can be immunized with an antigenic IGFR1 polypeptide, preferably amino acids 30-902 of SEQ ID NO: 11, as described by Lonberg, N., et al., (1994) Nature 368 (6474): 856-859; Fishwild, D., et al., (1996) Nature Biotechnology 14: 845-851 and WO 98/24884. Preferably, the mice will be 6-16 weeks of age upon the first immunization. For example, a purified preparation of IGFR1 or sIGFR1 can be used to immunize the HuMab mice intraperitoneally. The mice can also be immunized with whole HEK293 cells which are stably transfected with an IGFR1 gene. An "antigenic IGFR1 polypeptide" may refer to an IGFR1 polypeptide of any fragment thereof, preferably amino acids 30-902 of SEQ ID NO: 11, which elicits an anti-IGFR1 immune response, preferably in HuMab mice.

In general, HuMAb transgenic mice respond well when initially immunized intraperitoneally (IP) with antigen in complete Freund's adjuvant, followed by every other week IP immunizations (usually, up to a total of 6) with antigen in incomplete Freund's adjuvant. Mice can be immunized, first, with cells expressing IGFR1 (e.g., stably transfected HEK293 cells), then with a soluble fragment of IGFR1 (e.g., amino acids 30-902 of SEQ ID NO: 11) and continually receive alternating immunizations with the two antigens. The immune response can be monitored over the course of the immunization protocol with plasma samples being obtained by retroorbital bleeds. The plasma can be screened for the presence of anti-IGFR1 antibodies, for example by ELISA, and mice with sufficient titers of immunoglobulin can be used for fusions. Mice can be boosted intravenously with antigen 3 days before sacrifice and removal of the spleen. It is expected that 2-3 fusions for each antigen may need to be performed. Several mice can be immunized for each antigen. For example, a total of twelve HuMAb mice of the HC07 and HC012 strains can be immunized.

Hybridoma cells which produce the monoclonal, fully human anti-IGFR1 antibodies may be produced by methods which are commonly known in the art. These methods include, but are not limited to, the hybridoma technique originally developed by Kohler, et al., (1975) (Nature 256:495-497), as well as the trioma technique (Hering, et al., (1988) Biomed. Biochim. Acta. 47:211-216 and Hagiwara, et al., (1993) Hum. Antibod. Hybridomas 4:15), the human B-cell hybridoma technique (Kozbor, et al., (1983) Immunology Today 4:72 and Cote, et al., (1983) Proc. Natl. Acad. Sci. U.S.A 80:2026-2030), and the EBV-hybridoma technique (Cole, et al., in *Monoclonal Antibodies and Cancer Therapy*, Alan R. Liss, Inc., pp. 77-96, 1985). Preferably, mouse splenocytes are isolated and fused with PEG to a mouse myeloma cell line based upon standard protocols. The resulting hybridomas may then be screened for the production of antigen-specific antibodies. For example, single cell suspensions of splenic lymphocytes from immunized mice may by fused to one-sixth the number of P3X63-Ag8.653 nonsecreting mouse myeloma cells (ATCC, CRL 1580) with 50% PEG. Cells may be plated at approximately $2 \times 10^5$ cells/mL in a flat bottom microtiter plate, followed by a two week incubation in selective medium containing 20% fetal Clone Serum, 18% "653" conditioned media, 5% origen (IGEN), 4 mM L-glutamine, 1 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After two weeks, cells may be cultured in medium in which the HAT is replaced with HT. Individual wells may then be screened by ELISA for human anti-IGFR1 monoclonal IgG antibodies. Once extensive hybridoma growth occurs, medium can be observed usually after 10-14 days. The antibody secreting hybridomas may be replated, screened again, and if still positive for human IgG, anti-IGFR1 monoclonal antibodies, can be subcloned at least twice by limiting dilution. The stable subclones may then be cultured in vitro to generate small amounts of antibody in tissue culture medium for characterization.

The anti-IGFR1 antibodies and antigen-binding fragments thereof of the present invention may also be produced recombinantly (e.g., in an *E. coli*/T7 expression system as discussed above). In this embodiment, nucleic acids encoding the antibody molecules of the invention (e.g., $V_H$ or $V_L$) may be inserted into a pET-based plasmid and expressed in the *E. coli*/T7 system. There are several methods by which to produce recombinant antibodies which are known in the art. One example of a method for recombinant production of antibodies is disclosed in U.S. Pat. No. 4,816,567, which is herein incorporated by reference. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740, 461 and 4,959,455.

Anti-IGFR1 antibodies can also be synthesized by any of the methods set forth in U.S. Pat. No. 6,331,415.

Mammalian cell lines available as hosts for expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding portion thereof, the light chain and/or antigen-binding portion thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

It is likely that antibodies expressed by different cell lines or in transgenic animals will have different glycosylation from each other. However, all antibodies encoded by the nucleic acid molecules provided herein, or comprising the amino acid sequences provided herein are part of the instant invention, regardless of the glycosylation of the antibodies.

The term "monoclonal antibody," as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modifier "monoclonal" indicates the character of the antibody as being amongst a substantially homogeneous population of antibodies, and is not to be construed as requiring production of the antibody by any particular method. As mentioned above, the monoclonal antibodies to be used in accordance with the present invention may be made by the hybridoma method first described by Kohler, et al., (1975) Nature 256: 495.

A polyclonal antibody is an antibody which was produced among or in the presence of one or more other, non-identical antibodies. In general, polyclonal antibodies are produced from a B-lymphocyte in the presence of several other B-lymphocytes which produced non-identical antibodies. Usually, polyclonal antibodies are obtained directly from an immunized animal.

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai, et al., (1990) Clin. Exp. Immunol. 79: 315-321, Kostelny, et al., (1992) J. Immunol. 148:1547-1553. In addition, bispecific antibodies may be formed as "diabodies" (Holliger, et al., (1993) PNAS USA 90:6444-6448) or as "Janusins" (Traunecker, et al., (1991) EMBO J. 10:3655-3659 and Traunecker, et al., (1992) Int. J. Cancer Suppl. 7:51-52).

The term "fully human antibody" refers to an antibody which comprises human immunoglobulin protein sequences only. A fully human antibody may contain murine carbohydrate chains if produced in a mouse, in a mouse cell or in a hybridoma derived from a mouse cell. Similarly, "mouse antibody" refers to an antibody which comprises mouse immunoglobulin sequences only.

The present invention includes "chimeric antibodies"—an antibody which comprises a variable region of the present invention fused or chimerized with an antibody region (e.g., constant region) from another, non-human species (e.g., mouse, horse, rabbit, dog, cow, chicken). These antibodies may be used to modulate the expression or activity of IGFR1 in the non-human species.

"Single-chain Fv" or "sFv" antibody fragments have the $V_H$ and $V_L$ domains of an antibody, wherein these domains are present in a single polypeptide chain. Generally, the sFv polypeptide further comprises a polypeptide linker between the $V_H$ and $V_L$ domains which enables the sFv to form the desired structure for antigen binding. Techniques described for the production of single chain antibodies (U.S. Pat. Nos. 5,476,786; 5,132,405 and 4,946,778) can be adapted to produce anti-IGFR1-specific single chain antibodies. For a review of sFv see Pluckthun in *The Pharmacology of Monoclonal Antibodies*, vol. 113, Rosenburg and Moore eds. Springer-Verlag, N.Y., pp. 269-315 (1994).

"Disulfide stabilized Fv fragments" and "dsFv" refer to antibody molecules comprising a variable heavy chain ($V_H$) and a variable light chain ($V_L$) which are linked by a disulfide bridge.

Antibody fragments within the scope of the present invention also include $F(ab)_2$ fragments which may be produced by enzymatic cleavage of an IgG by, for example, pepsin. Fab fragments may be produced by, for example, reduction of $F(ab)_2$ with dithiothreitol or mercaptoethylamine. A Fab fragment is a $V_L$-$C_L$ chain appended to a $V_H$-$C_{H1}$ chain by a disulfide bridge. A $F(ab)_2$ fragment is two Fab fragments which, in turn, are appended by two disulfide bridges. The Fab portion of an $F(ab)_2$ molecule includes a portion of the $F_c$ region between which disulfide bridges are located.

An $F_V$ fragment is a $V_L$ or $V_H$ region.

Depending on the amino acid sequences of the constant domain of their heavy chains, immunoglobulins can be assigned to different classes. There are at least five major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2.

The anti-IGFR1 antibody molecules of the invention may also be conjugated to a chemical moiety. The chemical moiety may be, inter alia, a polymer, a radionuclide or a cytotoxic factor. Preferably the chemical moiety is a polymer which increases the half-life of the antibody molecule in the body of a subject. Suitable polymers include, but are not limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (Bioconj. Chem. 10:973-981) discloses PEG conjugated single-chain antibodies. Wen, et al., (2001) (Bioconj. Chem. 12:545-553) disclose conjugating antibodies with PEG which is attached to a radiometal chelator (diethylenetriaminpentaacetic acid (DTPA)).

The antibodies and antibody fragments of the invention may also be conjugated with labels such as $^{99}Tc$, $^{90}Y$, $^{111}In$, $^{32}P$, $^{14}C$, $^{125}I$, $^{3}H$, $^{131}I$, $^{11}C$, $^{15}O$, $^{13}N$, $^{18}F$, $^{35}S$, $^{51}Cr$, $^{57}To$, $^{226}$Ra, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{57}$Gd, $^{55}$Mn, $^{52}$Tr and $^{56}$Fe.

The antibodies and antibody fragments of the invention may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibody molecules may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *momordica charantia* inhibitor, curcin, crotin, *saponaria officinalis* inhibitor, mitogellin, restrictocin, phenomycin, and enomycin.

Any method known in the art for conjugating the antibody molecules of the invention to the various moieties may be employed, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407. Methods for conjugating antibodies are conventional and very well known in the art.

Chemotherapeutic Agents

The present invention includes combinations and methods comprising one or more binding compositions, such as an anti-IGFR1 antibody or antigen-binding fragment thereof in association with one or more chemotherapeutic agents. A chemotherapeutic agent provides a therapeutic effect which is helpful in the treatment of any medical condition being treated by administration of a binding composition of the invention (e.g., LCF/HCA). For example, if a binding composition is administered to treat cancer in a subject (e.g., human), the chemotherapeutic agent(s) provide an additional anti-cancer therapeutic effect or some other therapeutic effect which will improve the subject's treatment outcome. The chemotherapeutic agent component of a combination of the invention can operate by any mechanism (i.e., by the same mechanism by which the binding composition acts or by a different mechanism). Chemotherapeutic agents in the combinations and methods of the present invention include, but are, by no means, limited to, signal transduction inhibitors, cell cycle inhibitors, IGF/IGFR1 system modulators (e.g., inhibitors or activators), farnesyl protein transferase (FPT) inhibitors, epidermal growth factor receptor (EGFR) inhibitors, HER2 inhibitors, vascular epidermal growth factor (VEGF) receptor inhibitors, mitogen activated protein (MAP) kinase inhibitors, MEK inhibitors, AKT inhibitors, mTOR inhibitors, pI3 kinase inhibitors, Raf inhibitors, cyclin dependent kinase (CDK) inhibitors, microtubule stabilizers, microtubule inhibitors, SERMs/Antiestrogens, aromatase inhibitors, anthracyclines, proteasome inhibitors and agents which inhibit insulin-like growth factor (IGF) production and anti-sense inhibitors of IGFR1, IGF-1 or IGF2.

FPT inhibitors including tricyclic amide compounds such as those disclosed in U.S. Pat. No. 5,719,148 or in U.S. Pat. No. 5,874,442 can be combined with an anti-IGFR antibody. For example, any compound represented by formula I, below, may be included in the combinations of the invention:

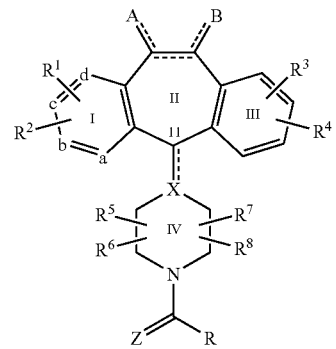

(1.0)

or a pharmaceutically acceptable salt or solvate thereof, wherein:
  one of a, b, c and d represents N or $NR^9$ wherein $R^9$ is O—, —$CH_3$ or —$(CH_2)_nCO_2H$ wherein n is 1 to 3, and the remaining a, b, c and d groups represent $CR^1$ or $CR^2$; or each of a, b, c, and d are independently selected from $CR^1$ or $CR^2$;
  each $R^1$ and each $R^2$ is independently selected from H, halo, —$CF_3$, —$OR^{10}$ (e.g., —$OCH_3$), —$COR^{10}$, —$SR^{10}$ (e.g., —$SCH_3$ and —$SCH_2C_6H_5$), —$S(O)_tR^{11}$ (wherein t is 0, 1 or 2, e.g., —$SOCH_3$ and —$SO_2CH_3$), —SCN, —$N(R^{10})_2$, —$NR^{10}R^{11}$, —$NO_2$, —$OC(O)R^{10}$, —$CO_2R^{10}$, —$OCO_2R^{11}$, —CN, —$NHC(O)R^{10}$, —$NHSO_2R^{10}$, —$CONHR^{10}$, —$CONHCH_2CH_2OH$, —$NR^{10}COOR^{11}$,

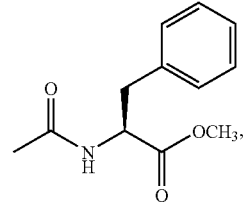

—$SR^{11}C(O)OR^{11}$ (e.g., —$SCH_2CO_2CH_3$), —$SR^{11}N(R^{75})_2$ wherein each $R^{75}$ is independently selected from H and —$C(O)OR^{11}$ (e.g., —$S(CH_2)_2NHC(O)O$-t-butyl and —$S(CH_2)_2NH_2$), benzotriazol-1-yloxy, tetrazol-5-ylthio, or substituted tetrazol-5-ylthio (e.g., alkyl substituted tetrazol5-ylthio such as 1-methyl-tetrazol-5-ylthio), alkynyl, alkenyl or alkyl, said alkyl or alkenyl group optionally being substituted with halo, —$OR^{10}$ or —$CO_2R^{10}$;
  $R^3$ and $R^4$ are the same or different and each independently represents H, any of the substituents of $R^1$ and $R^2$, or $R^3$ and $R^4$ taken together represent a saturated or unsaturated $C_5$-$C_7$ fused ring to the benzene ring (Ring III);
  $R^5$, $R^6$, $R^7$ and $R^8$ each independently represents H, —$CF_3$, —$COR^{10}$, alkyl or aryl, said alkyl or aryl optionally being substituted with —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, $OPO_3R^{10}$ or one of $R^5$, $R^6$, $R^7$ and $R^8$ can be taken in combination with $R^{40}$ as defined below to represent —$(CH_2)_r$— wherein r is 1 to 4 which can be substituted with lower alkyl, lower alkoxy, —$CF_3$ or aryl, or $R^5$ is combined with $R^6$ to represent =O or =S and/or $R^7$ is combined with $R^8$ to represent =O or =S;
  $R^{10}$ represents H, alkyl, aryl, or aralkyl (e.g., benzyl);
  $R^{11}$ represents alkyl or aryl;

X represents N, CH or C, which C may contain an optional double bond (represented by the dotted line) to carbon atom 11;

the dotted line between carbon atoms 5 and 6 represents an optional double bond, such that when a double bond is present, A and B independently represent —$R^{10}$, halo, —$OR^{11}$, —$OCO_2R^{11}$ or —$OC(O)R^{10}$, and when no double bond is present between carbon atoms 5 and 6, A and B each independently represent $H_2$, —$(OR^{11})_2$; H and halo, dihalo, alkyl and H, (alkyl)$_2$, —H and —OC(O)$R^{10}$, H and —$OR^{10}$, =O, aryl and H, =$NOR^{10}$ or —O—$(CH_2)_p$—O— wherein p is 2, 3 or 4;

R represents $R^{40}$, $R^{42}$, $R^{44}$, or $R^{54}$, as defined below;

$R^{40}$ represents H, aryl, alkyl, cycloalkyl, alkenyl, alkynyl or -D wherein -D represents

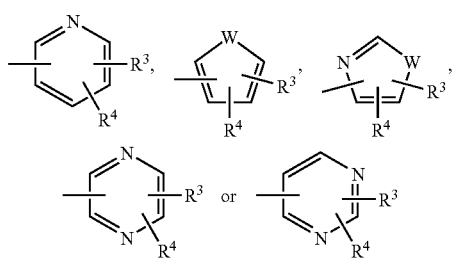

wherein $R^3$ and $R^4$ are as previously defined and W is O, S or $NR^{10}$ wherein $R^{10}$ is as defined above; said $R^{40}$ cycloalkyl, alkenyl and alkynyl groups being optionally substituted with from 1-3 groups selected from halo, —$CON(R^{10})_2$, aryl, —$CO_2R^{10}$, —$OR^{12}$, —$SR^{12}$, —$N(R^{10})_2$, —$N(R^{10})CO_2R^{11}$, —$COR^{12}$, —$NO_2$ or D, wherein -D, $R^{10}$ and $R^{11}$ are as defined above and $R^{12}$ represents $R^{10}$, —$(CH_2)_mOR^{10}$ or —$(CH_2)_qCO_2R^{10}$ wherein $R^{10}$ is as previously defined, m is 1 to 4 and q is 0 to 4; said alkenyl and alkynyl $R^{40}$ groups not containing —OH, —SH or —$N(R^{10})_2$ on a carbon containing a double or triple bond respectively; or $R^{40}$ represents phenyl substituted with a group selected from —$SO_2NH_2$, —$NHSO_2CH_3$, —$SO_2NHCH_3$, —$SO_2CH_3$, —$SOCH_3$, —$SCH_3$, or —$NHSO_2CF_3$, preferably, said group is located in the para (p-) position of the phenyl ring; or $R^{40}$ represents a group selected from

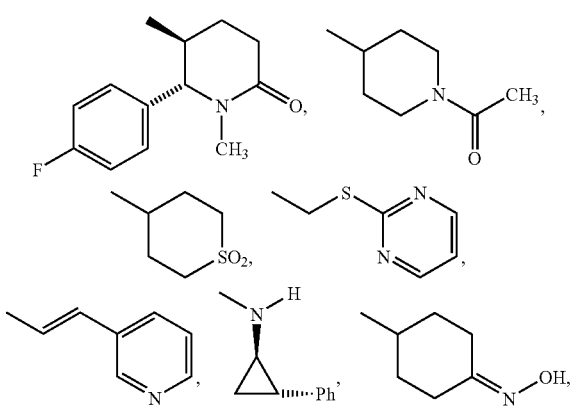

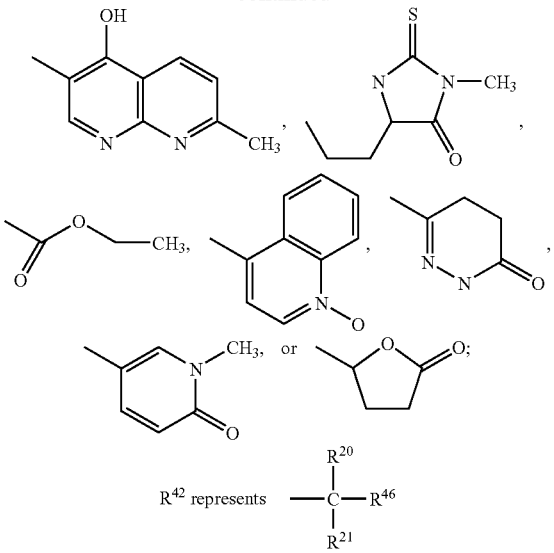

$R^{42}$ represents wherein $R^{20}$, $R^{21}$ and $R^{46}$ are each independently selected from the group consisting of:

(1) H;
(2) —$(CH_2)_qSC(O)CH_3$ wherein q is 1 to 3 (e.g., —$CH_2SC(O)CH_3$);
(3) —$(CH_2)_qOSO_2CH_3$ wherein q is 1 to 3 (e.g., —$CH_2OSO_2CH_3$);
(4) —OH;
(5) —$CS(CH_2)_w$(substituted phenyl) wherein w is 1 to 3 and the substitutents on said substituted phenyl group are the same substitutents as described below for said substituted phenyl (e.g., —C—S—$CH_2$-4-methoxyphenyl);
(6) —$NH_2$;
(7) —NHCBZ (wherein CBZ stands for carbonylbenzyloxy—i.e., CBZ represents —$C(O)OCH_2C_6H_5$);
(8) —$NHC(O)OR^{22}$ wherein $R^{22}$ is an alkyl group having from 1 to 5 carbon atoms (e.g., $R^{22}$ is t-butyl thus forming —NHBOC wherein BOC stands for tert-butyloxycarbonyl—i.e., BOC represents —$C(O)OC(CH_3)_3$), or $R^{22}$ represents phenyl substituted with 1 to 3 alkyl groups (e.g., 4-methylphenyl);
(9) alkyl (e.g., ethyl);
(10) —$(CH_2)_k$phenyl wherein k is 1 to 6, usually 1 to 4 and preferably 1 (e.g., benzyl);
(11) phenyl;
(12) substituted phenyl (i.e., phenyl substituted with from 1 to 3 substituents, preferably one) wherein the substituents are selected from the group consisting of: halo (e.g., Br, Cl, or I, with Br being preferred); $NO_2$; —OH; —$OCH_3$; —$NH_2$; —$NHR^{22}$; —$N(R^{22})_2$; alkyl (e.g., alkyl having from 1 to 3 carbons with methyl being preferred); —$O(CH_2)_t$phenyl (wherein t is from 1 to 3 with 1 being preferred); and —$O(CH_2)_t$substituted phenyl (wherein t is from 1 to 3 with 1 being preferred); examples of substituted phenyls include, but are not limited to, p-bromophenyl, m-nitrophenyl, o-nitrophenyl, m-hydroxy-phenyl, o-hydroxyphenyl, methoxyphenyl, p-methylphenyl, m-methyl-phenyl, and —$OCH_2C_6H_5$;
(13) naphthyl;
(14) substituted naphthyl, wherein the substituents are as defined for substituted phenyl above;

(15) bridged polycyclic hydrocarbons having from 5 to 10 carbon atoms (e.g., adamantyl and norbornyl);

(16) cycloalkyl having from 5 to 7 carbon atoms (e.g., cyclopentyl, and cyclohexyl);

(17) heteroaryl (e.g., pyridyl, and pyridyl N-oxide);

(18) hydroxyalkyl (e.g., —$(CH_2)_v$OH wherein v is 1 to 3, such as, for example, —$CH_2$OH);

(19) substituted pyridyl or substituted pyridyl N-oxide wherein the substituents are selected from methylpyridyl, morpholinyl, imidazolyl, 1-piperidinyl, 1-(4-methylpiperazinyl), —$S(O)_tR^{11}$, or any of the substituents given above for said substituted phenyl, and said substitutents are bound to a ring carbon by replacement of the hydrogen bound to said carbon;

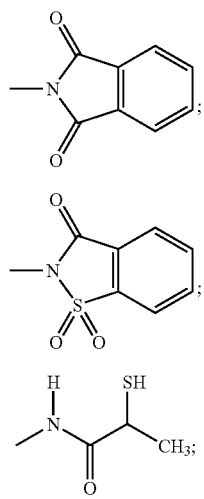

(20)

(21)

(22)

(23) —NHC(O)—$(CH_2)_k$-phenyl or —NH(O)—$(CH_2)_k$-substituted phenyl, wherein said k is as defined above (i.e., 1-6, usually 1-4 and preferably 1);

(24) piperidine Ring V:

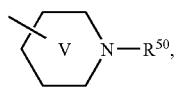

wherein $R^{50}$ represents H, alkyl (e.g., methyl), alkylcarbonyl (e.g., $CH_3C(O)$—), alkyloxycarbonyl (e.g., —C(O)O-t-$C_4H_9$, —$C(O)OC_2H5$, and —$C(O)OCH_3$), haloalkyl (e.g., trifluromethyl), or —$C(O)NH(R^{10})$ wherein $R^{10}$ is H or alkyl; Ring V includes

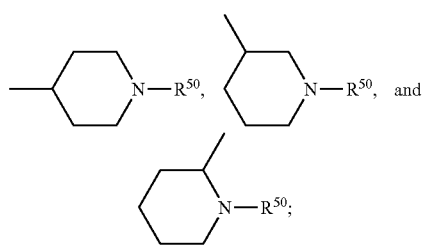

examples of Ring V include:

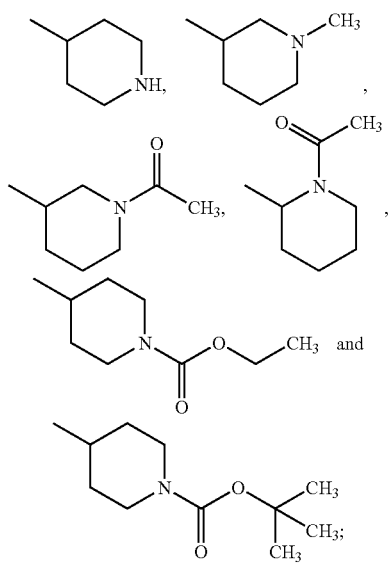

(25) —$NHC(O)CH_2C_6H_5$ or —$NHC(O)CH_2$-substituted-$C_6H_5$, for example —N $HC(O)CH_2$-p-hydroxyphenyl, —N $HC(O)CH_2$-m-hydroxyphenyl, and —NHC(O)$CH_2$-o-hydroxyphenyl;

(26) —$NHC(O)OC_6H_5$;

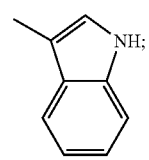

(27)

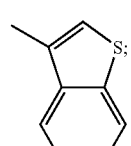

(28)

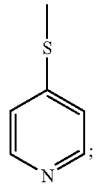

(29)

(30) —OC(O)-heteroaryl, for example

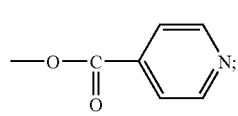

(31) —O-alkyl (e.g., —$OCH_3$);

(32) —$CF_3$;

(33) —CN;

(34) a heterocycloalkyl group of the formula

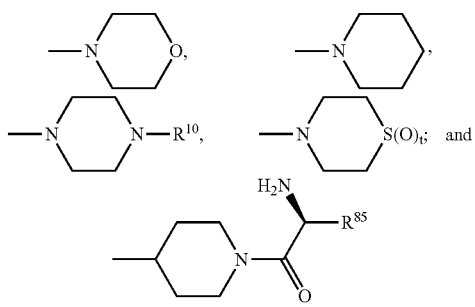

(35) a piperidinyl group of the formula
wherein $R^{85}$ is H, alkyl, or alkyl substituted by —OH or —SCH$_3$; or $R^{20}$ and $R^{21}$ taken together form a =O group and the remaining $R^{46}$ is as defined above; or Two of $R^{20}$, $R^{21}$ and $R^{46}$ taken together form piperidine Ring V

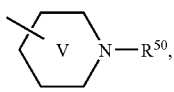

wherein $R^{50}$ represents H, alkyl (e.g., methyl), alkylcarbonyl (e.g., CH$_3$C(O)—), alkyloxycarbonyl (e.g., —C(O)O-t-C$_4$H$_9$, —C(O)OC$_2$H$_5$, and —C(O)OCH$_3$), haloalkyl (e.g., trifluro-methyl), or —C(O)NH(R$^{10}$) wherein R$^{10}$ is H or alkyl; Ring V includes

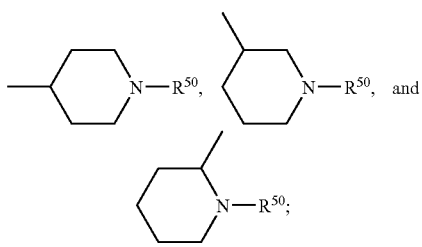

examples of Ring V include:

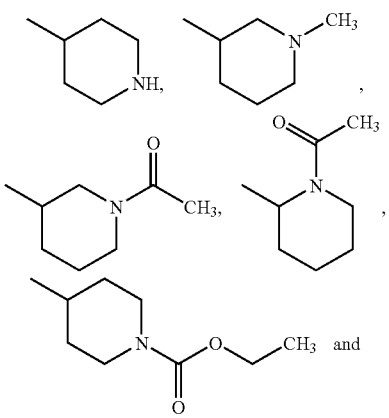

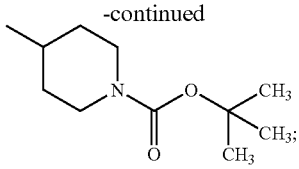

with the proviso $R^{46}$, $R^{20}$, and $R^{21}$ are selected such that the carbon atom to which they are bound does not contain more than one heteroatom (i.e., $R^{46}$, $R^{20}$, and $R^{21}$ are selected such that the carbon atom to which they are bound contains 0 or 1 heteroatom);

$R^{44}$ represents

wherein $R^{25}$ represents heteroaryl (e.g., pyridyl or pyridyl N-oxide), N-methylpiperidinyl or aryl (e.g., phenyl and substituted phenyl); and $R^{48}$ represents H or alkyl (e.g., methyl);

$R^{54}$ represents an N-oxide heterocyclic group of the formula (i), (ii), (iii) or (iv):

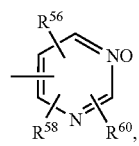

(i)

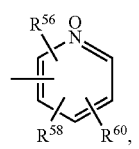

(ii)

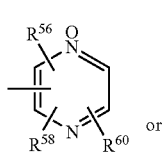

(iii)

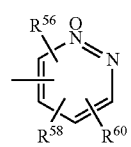

(iv)

wherein $R^{56}$, $R^{58}$, and $R^{60}$ are the same or different and each is independently selected from H, halo, —CF$_3$, —OR$^{10}$, —C(O)R$^{10}$, —SR$^{10}$, —S(O)$_e$R$^{11}$ (wherein e is 1 or 2), —N(R$^{10}$)$_2$, —NO$_2$, —CO$_2$R$^{10}$, —OCO$_2$R$^{11}$, —OCOR$^{10}$, alkyl, aryl, alkenyl or alkynyl, which alkyl may be substituted with —OR$^{10}$, —SR$^{10}$ or —N(R$^{10}$)$_2$ and which alkenyl may be substituted with OR$^{11}$ or SR$^{11}$; or $R^{54}$ represents an N-oxide heterocyclic group of the formula (ia), (iia), (iiia) or (iva):

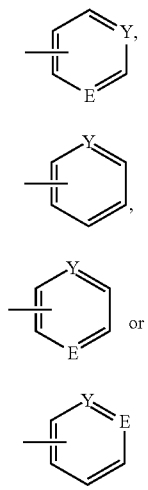

wherein Y represents $N^+$—$O^-$ and E represents N; or $R^{54}$ represents an alkyl group substituted with one of said N-oxide heterocyclic groups (i), (ii), (iii), (iv), (ia), (iia), (iiia) or (iva);

Z represents O or S such that R can be taken in combination with $R^5$, $R^6$, $R^7$ or $R^8$ as defined above, or R represents $R^{40}$, $R^{42}$, $R^{44}$ or $R^{54}$.

Examples of $R^{20}$, $R^{21}$, and $R^{46}$ for the above formulas include:

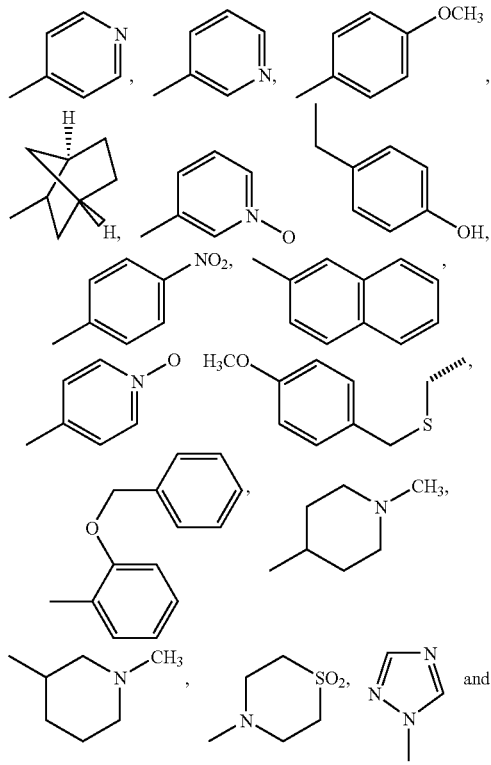

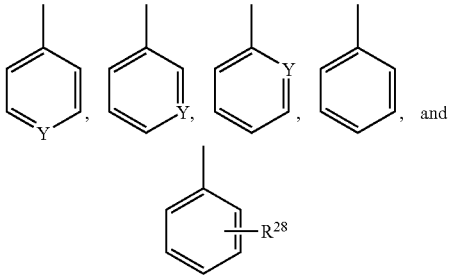

Examples of $R^{25}$ groups include:

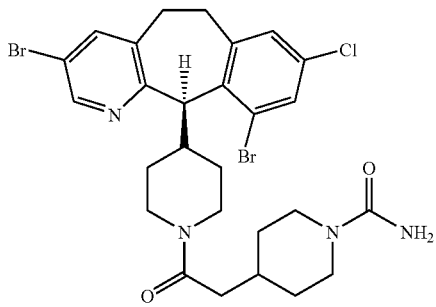

wherein Y represents N or NO, $R^{28}$ is selected from the group consisting of: $C_1$ to $C_4$ alkyl, halo, hydroxy, $NO_2$, amino (—$NH_2$), —$NHR^{30}$, and —$N(R^{30})_2$ wherein $R^{30}$ represents $C_1$ to $C_6$ alkyl.

In one embodiment, the following tricyclic amide is included with an anti-IGFR antibody:

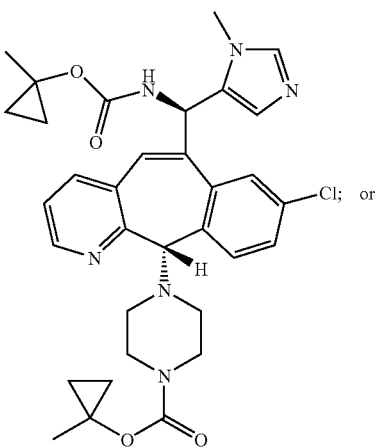

(lonafarnib; Sarasar™; Schering-Plough; Kenilworth, N.J.). In another embodiment, one of the following FPT inhibitors is included with an anti-IGFR antibody:

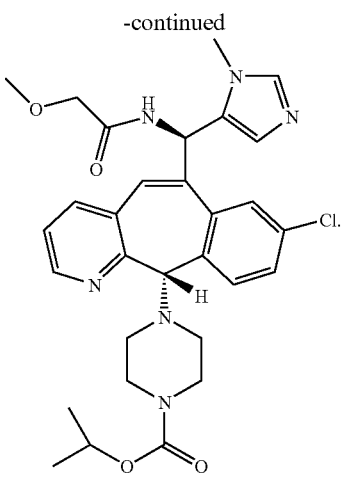

FPT inhibitors, which can be included with an anti-IGFR antibody, include BMS-214662

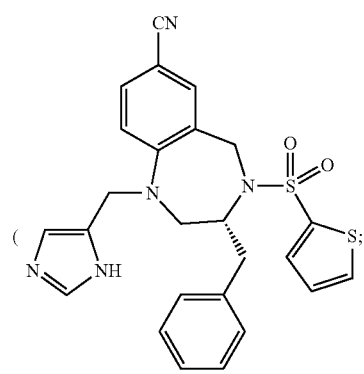

Hunt et al., J. Med. Chem. 43(20):3587-95 (2000); Dancey et al., Curr. Pharm. Des. 8:2259-2267 (2002); (R)-7-cyano-2,3,4,5-tetrahydro-1-(1H-imidazol-4-ylmethyl)-3-(phenylmethyl)-4-(2-thienylsulfonyl)-1H-1,4-benzodiazepine)) and R155777 (tipifarnib; Garner et al., Drug Metab. Dispos. 30(7):823-30 (2002); Dancey et al., Curr. Pharm. Des. 8:2259-2267 (2002); (B)-6-[amino(4-chlorophenyl)(1-methyl-1H-imidazol-5-yl)-methyl]-4-(3-chlorophenyl)-1-methyl-2(1H)-quinolinone];

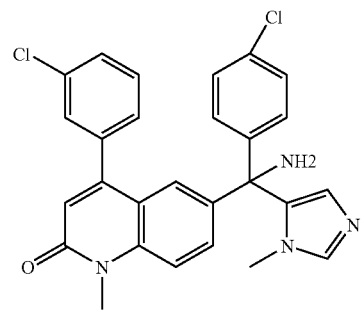

sold as Zarnestra™; Johnson & Johnson; New Brunswick, N.J.).

Inhibitors which antagonize the action of the EGF Receptor or HER2, which can be included with an anti-IGFR antibody, include trastuzumab
  (sold as Herceptin®; Genentech, Inc.; S. San Francisco, Calif.); CP-724714

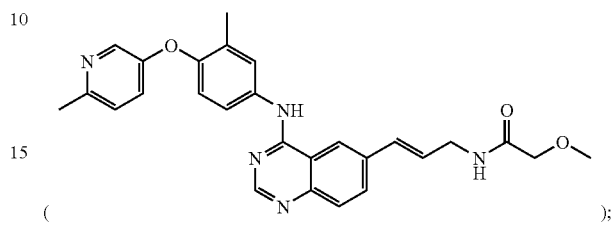

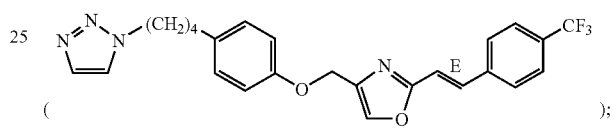

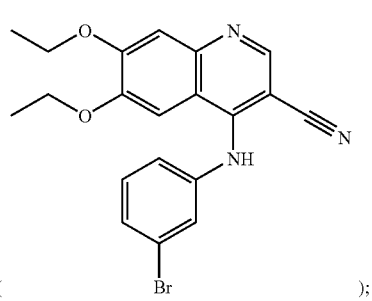

gefitinib (Baselga et al., Drugs 60 Suppl 1:33-40 (2000); ZD-1893; 4-(3-chloro-4-fluoroanilino)-7-methoxy-6-(3-morpholinopropoxy)quinazoline; sold as Iressa™; AstraZeneca; Wilmington, Del.;

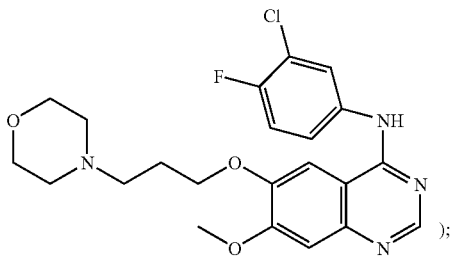

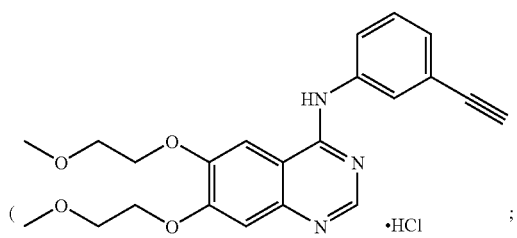

erlotinib, Hidalgo et al., J. Clin. Oncol. 19(13): 3267-3279 (2001)), Lapatanib

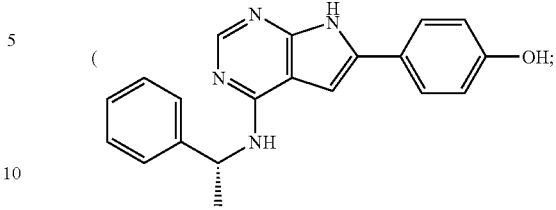

CGP-75166), GW-572016, any anti-EGFR antibody and any anti-HER2 antibody.

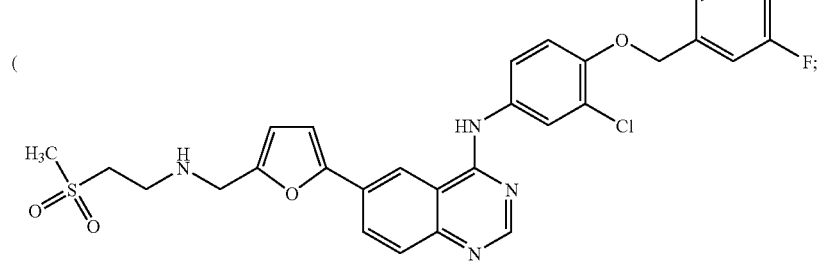

GW2016; Rusnak et al., Molecular Cancer Therapeutics 1:85-94 (2001); N-{3-Chloro-4-[(3-fluorobenzyl)oxy]phenyl}-6-[5-({[2-(methylsulfonyl)ethyl]amino}methyl)-2-furyl]-4-quinazolinamine; PCT Application No. WO99/35146), Canertinib (CI-1033;

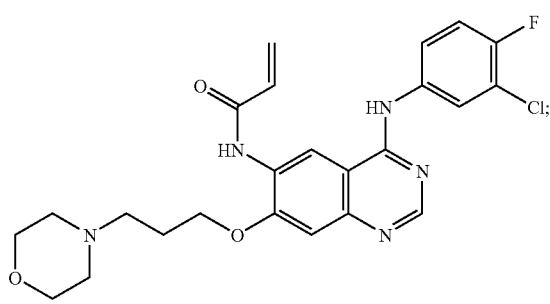

Erlichman et al., Cancer Res. 61(2):739-48 (2001); Smaill et al., J. Med. Chem. 43(7):1380-97 (2000)), ABX-EGF antibody (Abgenix, Inc.; Freemont, Calif.; Yang et al., Cancer Res. 59(6):1236-43 (1999); Yang et al., Crit Rev Oncol Hematol. 38(1):17-23 (2001)), erbitux (U.S. Pat. No. 6,217,866; IMC-C225, cetuximab; Imclone; New York, N.Y.), EKB-569

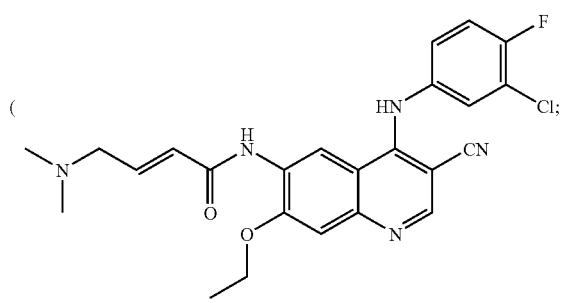

Numerous other small molecules which have been described as being useful to inhibit EGFR can be combined with an anti-IGFR antibody. For example, U.S. Pat. No. 5,656,655, discloses styryl substituted heteroaryl compounds that inhibit EGFR. U.S. Pat. No. 5,646,153 discloses bis mono and/or bicyclic aryl heteroaryl carbocyclic and heterocarbocyclic compounds that inhibit EGFR and/or PDGFR. U.S. Pat. No. 5,679,683 discloses tricyclic pyrimidine compounds that inhibit the EGFR. U.S. Pat. No. 5,616,582 discloses quinazoline derivatives that have receptor tyrosine kinase inhibitory activity. Fry et al., Science 265 1093-1095 (1994) discloses a compound having a structure that inhibits EGFR (see FIG. 1 of Fry et al.). U.S. Pat. No. 5,196,446, discloses heteroarylethenediyl or heteroarylethenediylaryl compounds that inhibit EGFR. Panek, et al., Journal of Pharmacology and Experimental Therapeutics 283, 1433-1444 (1997) disclose a compound identified as PD166285 that inhibits the EGFR, PDGFR, and FGFR families of receptors. PD166285 is identified as 6-(2,6-dichlorophenyl)-2-(4-(2-diethylaminoethoxy)phenylamino)-8-methyl-8H-pyrido(2,3-d)pyrimidin-7-one.

VEGF receptor inhibitors, which can be combined with an anti-IGFR antibody, include PTK787/ZK 222584 (Thomas et al., Semin Oncol. 30(3 Suppl 6):32-8 (2003)) and the humanized anti-VEGF antibody Bevacizumab (sold under the brand name Avastin™; Genentech, Inc.; South San Francisco, Calif.).

MAP kinase inhibitors, which can be combined with an anti-IGFR antibody, include VX-745 (Haddad, Curr Opin. Investig. Drugs 2(8):1070-6 (2001)).

MAP kinase kinase (MEK) inhibitors, which can be combined with an anti-IGFR antibody, include PD 184352 (Sebolt-Leopold, et al. Nature Med. 5: 810-816 (1999)).

mTOR inhibitors, which can be combined with an anti-IGFR antibody, include rapamycin and CCI-779 (Sehgal et al., Med. Res. Rev., 14:1-22 (1994); Elit, Curr. Opin. Investig. Drugs 3(8):1249-53 (2002)).

pI3 kinase inhibitors, which can be combined with an anti-IGFR antibody, include LY294002, LY292223, LY292696, LY293684, LY293646 (Vlahos et al., J. Biol. Chem. 269(7): 5241-5248 (1994)) and wortmannin.

Raf inhibitors, which can be combined with an anti-IGFR antibody, include BAY-43-9006, (Wilhelm et al., Curr. Pharm. Des. 8:2255-2257 (2002)), ZM336372, L-779,450 or any other Raf inhibitor disclosed in Lowinger et al., Curr. Pharm Des. 8:2269-2278 (2002).

Cyclin dependent kinase inhibitors, which can be combined with an anti-IGFR antibody, include flavopiridol (L86-8275/HMR 1275; Senderowicz, Oncogene 19(56): 6600-6606 (2000)) and UCN-01 (7-hydroxy staurosporine; Senderowicz, Oncogene 19(56): 6600-6606 (2000)).

IGF/IGFR inhibitors, which can be combined with an anti-IGFR antibody, include IGF inhibitory peptides (U.S. Published Patent Application No. 20030092631 A1; PCT Application Publication NOs. WO 03/27246 A2; WO 02/72780), 4-amino-5-phenyl-7-cyclobutyl-pyrrolo[2,3-d]pyrimidine derivatives such as those disclosed in PCT Application Publication No. WO 02/92599 (e.g.,

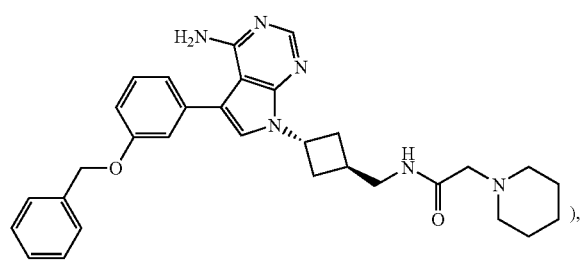

flavonoid glycones such as quercetin (PCT Application Publication No. WO 03/39538) and anti-IGFR1 antibodies other than those of the present invention.

Other Anti-IGFR1 antibodies, which can be combined with an anti-IGFR antibody of the invention, are disclosed, for example, in Burtrum et. al Cancer Research 63:8912-8921 (2003); in French Patent Applications FR2834990, FR2834991 and FR2834900 and in PCT Application Publication Nos. WO 03/59951; WO 04/71529; WO 03/106621; WO 04/83248; WO 04/87756 and WO 02/53596.

Agents which inhibit IGF production, which can be combined with an anti-IGFR antibody, include octreotide (L-Cysteinamide, D-phenylalanyl-L-cysteinyl-L-phenylalanyl-D-tryptophyl-L-lysyl-L-threonyl-N-[2-hydroxy-1-(hydroxymethyl) propyl]-, cyclic (2_7)-disulfide; [R R*,R*)];

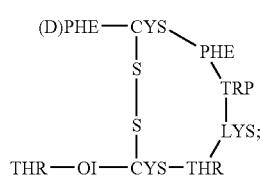

Katz et al., Clin Pharm. 8(4):255-73 (1989); sold as Sandostatin LAR® Depot; Novartis Pharm. Corp; E. Hanover, N.J.).

Proteasome inhibitors, which can be combined with an anti-IGFR antibody, include bortezomib

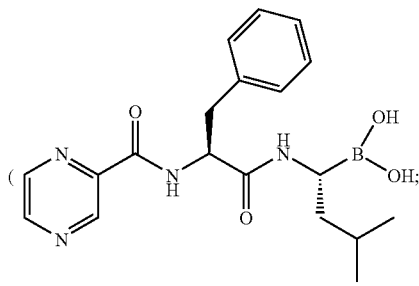

[(1R)-3-methyl-1-[[(2S)-1-oxo-3-phenyl-2-[(pyrazinyl-carbonyl) amino]propyl]amino]butyl]boronic acid; sold as Velcade™; Millennium Pharm., Inc.; Cambridge, Mass.).

Microtubule stabilizers and microtubule depolymerizers/inhibitors, which can be combined with an anti-IGFR antibody, include paclitaxel

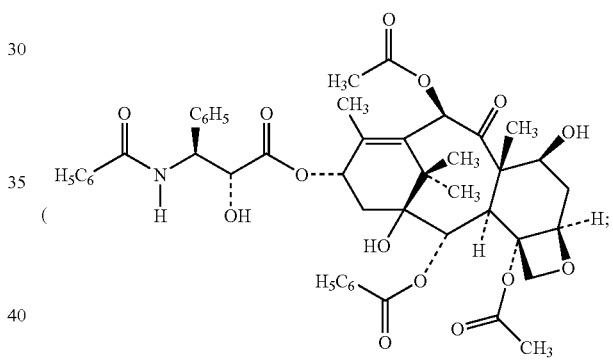

sold as Taxol®; Bristol-Myers Squibb; New York, N.Y.) and docetaxel

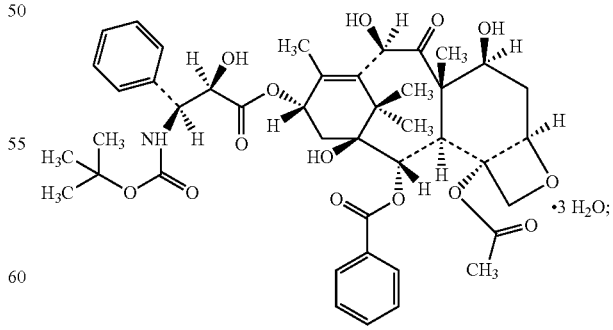

sold as Taxotere®; Aventis Pharm, Inc.; Bridgewater, N.J.); vincristine

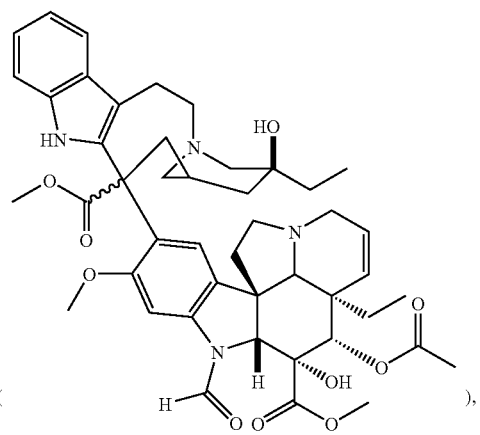

vinblastine

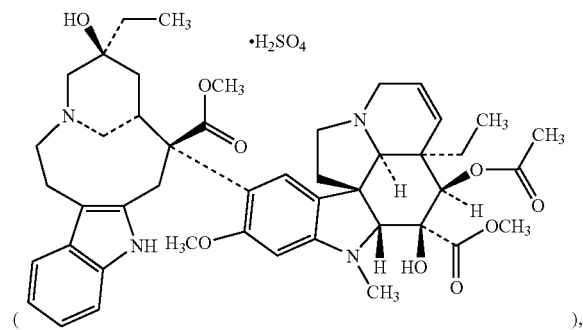

epothilone B and BMS-247550

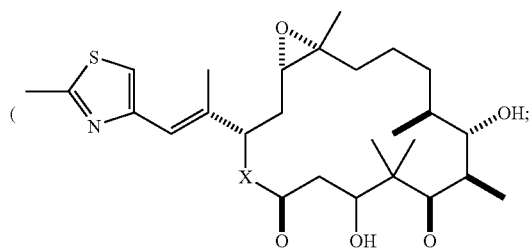

Epothilone B; X = O
BMS-247550; X = NH

Lee et al., Clin. Cancer Res. 7(5):1429-37 (2001)), podophyllotoxins and derivatives thereof including Etoposide (VP-16;

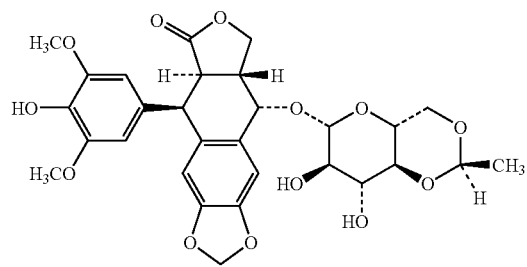

) and

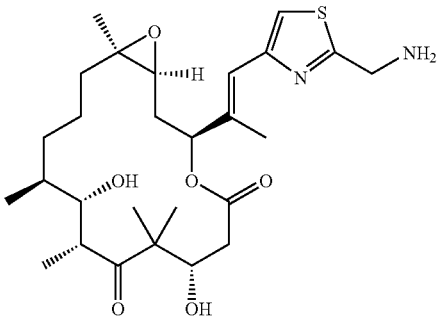

Temozolomide

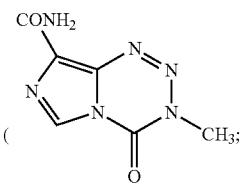

sold by Schering Corp.; Kenilworth, N.J. as Temodar®) may also be combined with an anti-IGFR antibody of the invention.

Anthracyclines which may be combined with an anti-IGFR antibody include doxorubicin

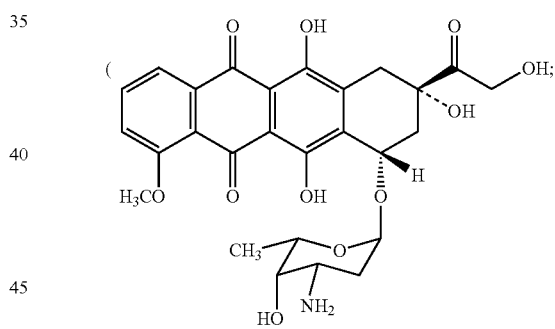

sold as Doxil®; Ortho Biotech Products L.P.; Raritan, N.J.); daunorubicin

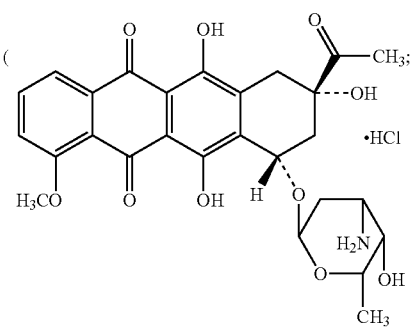

sold as Cerubidine®; Ben Venue Laboratories, Inc.; Bedford, Ohio) and epirubicin

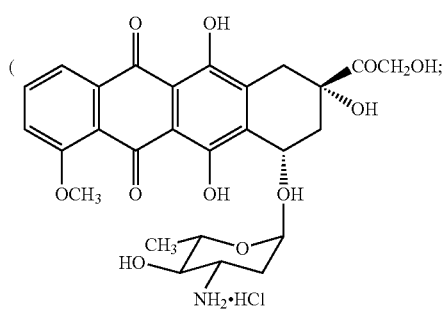

sold as Ellence®; Pharmacia & Upjohn Co; Kalamazoo, Mich.).

Anti-estrogens and selective estrogen receptor modulators (SERMs), which can be combined with the anti-IGFR antibodies of the invention include droloxifene (3-hydroxytamoxifen), 4-hydroxytamoxifen

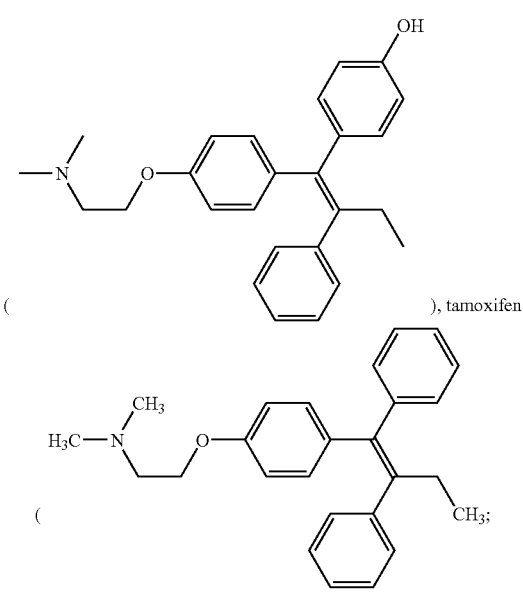

sold as Nolvadex®; Astra Zeneca; Wilmington, Del.); pipendoxifene

ERA-923; Greenberger et al., Clin. Cancer Res. 7(10):3166-77 (2001)); arzoxifene

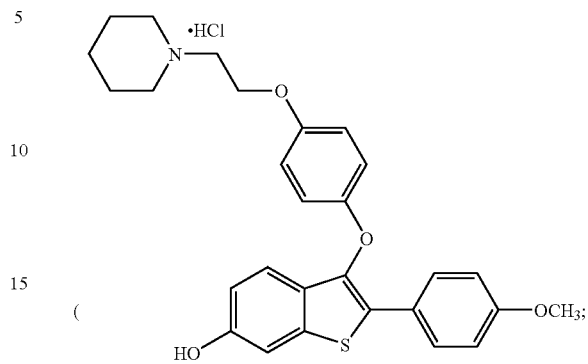

LY353381; Sato et al., J. Pharmacol. Exp. Ther. 287(1):1-7 (1998)); raloxifene

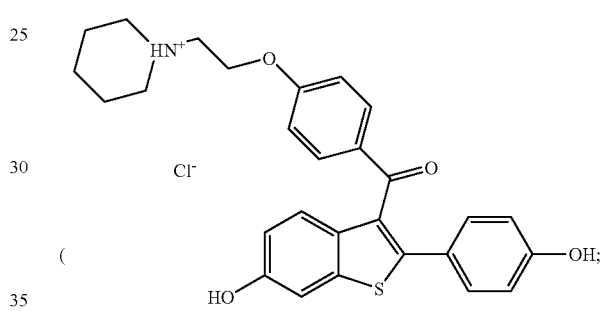

sold as Evista®; Eli Lilly & Co.; Indianapolis, Ind.); fulvestrant

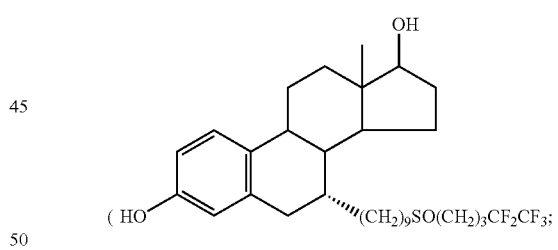

ICI-182780; sold as Faslodex; Astra Zeneca; Wilmington, Del.); acolbifene (EM-652;

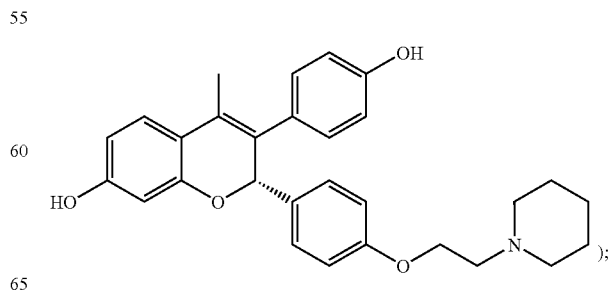

toremifine

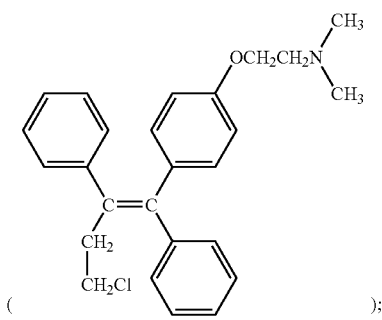

lasofoxifene (CP-336,156;

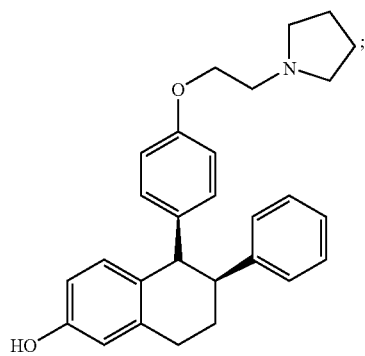

Ke et al., Endocrinology 139(4):2068-76 (1998)); idoxifene (pyrrolidino-4-iodotamoxifen;

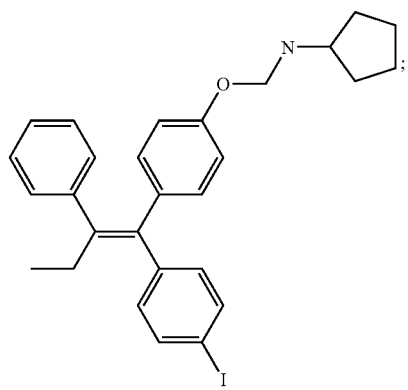

Nuttall et al., Endocrinology 139(12):5224-34 (1998)); TSE-424

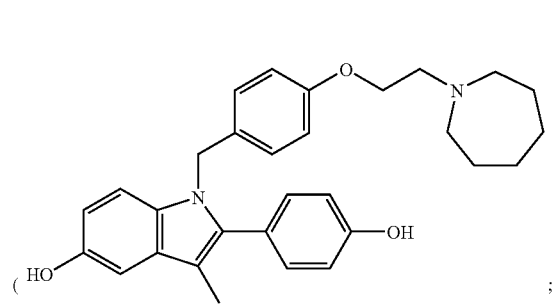

Bazedoxifene; WAY-140424); HMR-3339 and ZK-186619.

Aromatase inhibitors, which can be included with an anti-IGFR antibody, include anastrazole

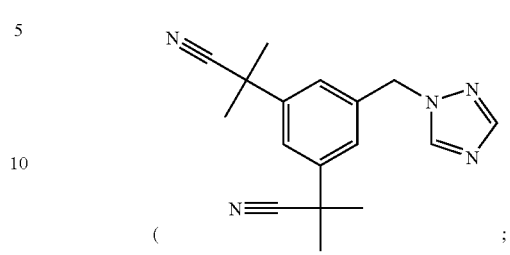

Dukes et al., J. Steroid. Biochem. Mol. Biol. 58(4):439-45 (1996)), letrozole

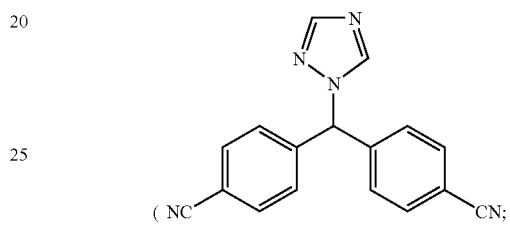

sold as Femara®; Novartis Pharmaceuticals Corp.; E. Hanover, N.J.) and exemestane

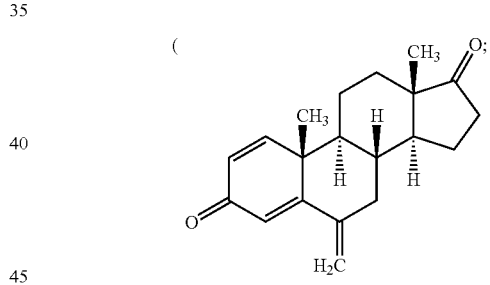

sold as Aromasin®; Pharmacia Corp.; Kalamazoo, Mich.).

Oxaliplatin

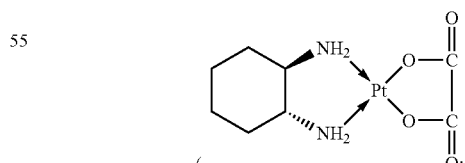

sold as Eloxatin™ by Sanofi-Synthelabo Inc.; New York, N.Y.) can also be combined with an anti-IGFR antibody of the invention.

An anti-IGFR antibody can also be combined with gemcitabine HCl

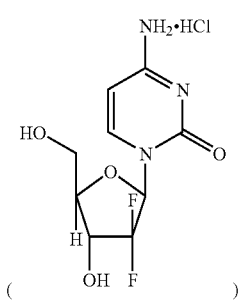

with retinoic acid or with any IGFR inhibitor set forth in any of Mitsiades et al., Cancer Cell 5:221-230 (2004); Garcia-Echeverria et. al., Cancer Cell 5:231-239, 2004; WO 2004/030627 or WO 2004/030625.

Topoisomerase inhibitors which may be combined with an anti-IGFR antibody include camptothecin

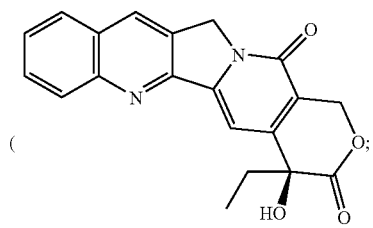

Stork et al., J. Am. Chem. Soc. 93(16): 4074-4075 (1971); Beisler et al., J. Med. Chem. 14(11): 1116-1117 (1962)), topotecan

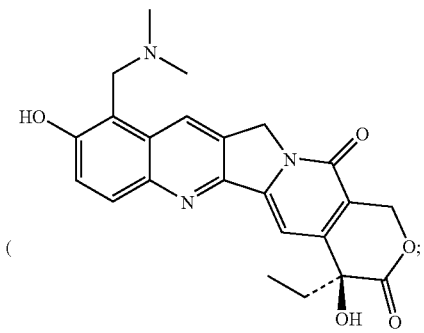

sold as Hycamtin®; GlaxoSmithKline, Research Triangle Park, N.C.; Rowinski et al., J. Clin. Oncol. 10(4): 647-656 (1992)), etoposide

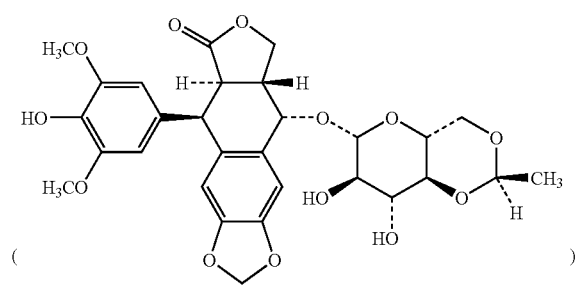

and irinotecan

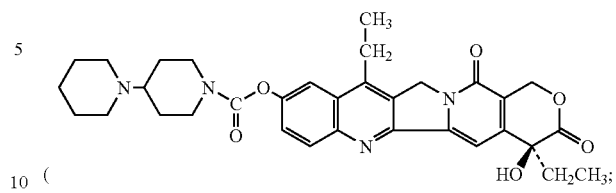

sold as Camptosar®; Pharmacia & Upjohn Co.; Kalamazoo, Mich.).

Antisense oligonucleotides can be produced that are complementary to the mRNA of the IGFR1, IGF-1 or IGF-2 gene and can be used to inhibit transcription or translation of the genes. Production of antisense oligonucleotides effective for therapeutic uses is well known in the art. Antisense oligonucleotides are often produced using derivatized or modified nucleotides in order to increase half-life or bioavailability. The primary sequence of the IGFR1, IGF-1 or IGF-2 gene can also be used to design ribozymes. Most synthetic ribozymes are generally hammerhead, tetrahymena and haripin ribozymes. Methods of designing and using ribozymes to cleave specific RNA species are well known in the art.

The chemical structures and other useful information regarding many of the foregoing agents can be found in the *Physicians' Desk Reference*, 57$^{th}$ ed., 2003; Thompson PDR; Montvale, N.J.

Categorization of a particular agent into a particular class (e.g., FPT inhibitor or microtubule stabilizer) is only done for descriptive purposes and is not meant to limit the invention in any way.

The scope of present invention includes compositions and methods comprising an anti-IGFR antibody along with one or more of the foregoing chemotherapeutic agents or any salt, hydrate, isomer, formulation, solvate or prodrug thereof.

Pharmaceutical Compositions

A combination, or any component thereof, of the invention can be incorporated into a pharmaceutical composition, along with a pharmaceutically acceptable carrier, suitable for administration to a subject in vivo. The scope of the present invention includes pharmaceutical compositions which may be administered to a subject by any route, such as a non-parenteral (e.g., oral, ocular, topical or pulmonary (inhalation)) or a parenteral route (e.g., intratumoral injection, intravenous injection, intraarterial injection, subcutaneous injection or intramuscular injection). In one embodiment, the pharmaceutical compositions of the invention comprise an antibody comprising 15H12/19D12 LCF and 15H12/19D12 HCA in association with one or more chemotherapeutic agents and a pharmaceutically acceptable carrier.

As stated above, the combinations of the invention include the binding composition component and chemotherapeutic agent component "in association" with one another. The term "in association" indicates that the components of the combinations of the invention can be formulated into a single composition for simultaneous delivery or formulated separately into two or more compositions (e.g., a kit). For example, the scope of the present invention includes combinations comprising an anti-IGFR1 antibody formulated for parenteral administration (e.g., intravenous) to a subject and a chemotherapeutic agent formulated for oral delivery (e.g., pill, tablet, capsule). Alternatively, both components of the combination can be formulated, separately or together, for parenteral delivery or non-parenteral delivery (e.g., oral).

For general information concerning formulations, see, e.g., Gilman, et al., (eds.) (1990), *The Pharmacological Bases of Therapeutics,* 8th Ed., Pergamon Press; A. Gennaro (ed.), *Remington's Pharmaceutical Sciences,* 18th Edition, (1990), Mack Publishing Co., Easton, Pa.; Avis, et al., (eds.) (1993) *Pharmaceutical Dosage Forms: Parenteral Medications* Dekker, New York; Lieberman, et al., (eds.) (1990) *Pharmaceutical Dosage Forms: Tablets* Dekker, New York; and Lieberman, et al., (eds.) (1990), *Pharmaceutical Dosage Forms: Disperse Systems* Dekker, New York, Kenneth A. Walters (ed.) (2002) *Dermatological and Transdermal Formulations (Drugs and the Pharmaceutical Sciences)*, Vol 119, Marcel Dekker.

Pharmaceutically acceptable carriers are conventional and very well known in the art. Examples include aqueous and nonaqueous carriers, stabilizers, antioxidants, solvents, dispersion media, coatings, antimicrobial agents, buffers, serum proteins, isotonic and absorption delaying agents, and the like that are physiologically compatible. Preferably, the carrier is suitable for injection into a subject's body.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Stabilizers, such as α,α-trehalose dihydrate may be included for stabilizing the antibody molecules of the invention from degrading effects of dessication or freeze-drying.

Examples of pharmaceutically-acceptable antioxidants include: water soluble antioxidants such as ascorbic acid, cysteine hydrochloride, sodium bisulfate, sodium metabisulfite, sodium sulfite and the like; and oil-soluble antioxidants such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Prevention of the presence of microorganisms may be ensured both by sterilization procedures, and by the inclusion of various antimicrobial agents such as EDTA, EGTA, paraben, chlorobutanol, phenol sorbic acid, and the like.

Suitable buffers which may be included in the pharmaceutical compositions of the invention include L-histidine based buffers, phosphate based buffers (e.g., phosphate buffered saline, pH≅7), sorbate based buffers or glycine-based buffers.

Serum proteins which may be included in the pharmaceutical compositions of the invention may include human serum albumin.

Isotonic agents, such as sugars, ethanol, polyalcohols (e.g., glycerol, propylene glycol, liquid polyethylene glycol, mannitol or sorbitol), sodium citrate or sodium chloride (e.g., buffered saline) may also be included in the pharmaceutical compositions of the invention.

Prolonged absorption of an injectable pharmaceutical form may be brought about by the inclusion of agents which delay absorption such as aluminum monostearate and/or gelatin.

Dispersions can also be prepared in glycerol, liquid polyethylene glycols, and mixtures thereof and in oils.

Pharmaceutically acceptable carriers include sterile aqueous solutions or dispersions and sterile powders for the extemporaneous preparation of sterile injectable solutions or dispersions. The use of such media and agents for pharmaceutically active substances is well known in the art.

Sterile injectable solutions can be prepared by incorporating a combination of the invention or any component thereof (e.g., binding composition and/or chemotherapeutic agent), in the required amount, in an appropriate solvent, optionally with one or a combination of ingredients enumerated above, as required, followed by sterilization microfiltration. Generally, dispersions are prepared by incorporating the active ingredient (e.g., binding composition and/or chemotherapeutic agent) into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional, desired ingredient from a previously sterile-filtered solution thereof.

A combination or the invention or any component thereof (e.g., binding composition and/or chemotherapeutic agent) may also be orally administered. Pharmaceutical compositions for oral administration may include additives and carriers such as starch (e.g., potato, maize or wheat starch or cellulose), starch derivatives (e.g., microcrystalline cellulose or silica), sugars (e.g., lactose), talc, lactose, stearate, magnesium carbonate or calcium phosphate. In order to ensure that oral compositions are well tolerated by the patient's digestive system, mucus formers or resins may be included. It may also be desirable to improve tolerance by formulating in a capsule which is insoluble in the gastric juices. An exemplary pharmaceutical composition of this invention in the form of a capsule is prepared by filling a standard two-piece hard gelatin capsule with the combination of the invention or any component thereof in powdered form, lactose, talc and magnesium stearate. Oral administration of immunoglobulins has been described (Foster, et al., (2001) Cochrane Database System rev. 3:CD001816).

A combination of the invention or any component thereof (e.g., binding composition and/or chemotherapeutic agent) may also be included in a pharmaceutical composition for topical administration. Formulations suitable for topical administration include liquid or semi-liquid preparations suitable for penetration through the skin to the site where treatment is required, such as liniments, lotions, creams, ointments or pastes, and drops suitable for administration to the eye, ear or nose.

Drops according to the present invention may comprise sterile aqueous or oily solutions or suspensions and may be prepared by dissolving the combination of the invention or any component thereof (e.g., binding composition and/or chemotherapeutic agent) in a suitable aqueous solution of a bactericidal and/or fungicidal agent and/or any other suitable preservative, and preferably including a surface active agent. The resulting solution may then be clarified by filtration.

Lotions according to the present invention include those suitable for application to the skin or eye. An eye lotion may comprise a sterile, aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the combination of the invention or any component thereof in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

A combination of the invention or any component thereof (e.g., binding composition and/or chemotherapeutic agent) may also be administered by inhalation. A suitable pharmaceutical composition for inhalation may be an aerosol. An exemplary pharmaceutical composition for inhalation of a combination of the invention or any component thereof may include: an aerosol container with a capacity of 15-20 ml comprising the active ingredient (e.g., binding composition and/or chemotherapeutic agent), a lubricating agent, such as polysorbate 85 or oleic acid, dispersed in a propellant, such as freon, preferably in a combination of 1,2-dichlorotetrafluoroethane and difluorochloromethane. Preferably, the composition is in an appropriate aerosol container adapted for either intranasal or oral inhalation administration.

Dosage

Preferably, a combination of the invention is administered to a subject at a "therapeutically effective dosage" or "therapeutically effective amount" which preferably inhibits a disease or condition (e.g., tumor growth) to any extent-preferably by at least about 20%, more preferably by at least about 40%, even more preferably by at least about 60%, and still more preferably by at least about 80%-100% relative to untreated subjects. The ability of a combination of the invention or any component thereof to inhibit cancer can be evaluated in an animal model system predictive of efficacy in human tumors. Alternatively, this property can be evaluated by examining the ability of a combination of the invention or any component thereof to inhibit tumor cell growth in vitro by assays well-known to the skilled practitioner. One of ordinary skill in the art would be able to determine such amounts based on such factors as the subject's size, the severity of the subject's symptoms, and the particular composition or route of administration selected.

Dosage regimens may be adjusted to provide the optimum desired response (e.g., a therapeutic response). For example, a dose may be administered, several divided doses may be administered over time or the dose may be proportionally reduced or increased as indicated by exigencies of the therapeutic situation. It is especially advantageous to formulate parenteral compositions in dosage unit form for ease of administration and uniformity of dosage.

A physician or veterinarian having ordinary skill in the art can readily determine and prescribe the effective amount of the pharmaceutical composition required. For example, the physician or veterinarian could start doses of the antibody or antigen-binding fragment of the invention employed in the pharmaceutical composition at levels lower than that required in order to achieve the desired therapeutic effect and gradually increase the dosage until the desired effect is achieved. The effectiveness of a given dose or treatment regimen of an antibody or combination of the invention can be determined, for example, by determining whether a tumor being treated in the subject shrinks or ceases to grow. The size of tumor can be easily determined, for example, by X-ray, magnetic resonance imaging (MRI) or visually in a surgical procedure.

In general, a suitable daily dose of a combination of the invention or any component thereof may be that amount which is the lowest dose effective to produce a therapeutic effect. Such an effective dose will generally depend upon the factors described above. It is preferred that administration be by injection, preferably proximal to the site of the target (e.g., tumor). If desired, a therapeutically effective daily dose of an antibody or antibody/chemotherapeutic agent combination of the invention or pharmaceutical composition thereof may be administered as two, three, four, five, six or more sub-doses administered separately at appropriate intervals throughout the day. In an embodiment, a "therapeutically effective" dosage of any anti-IGFR antibody of the present invention is in the range of about 3 mg/kg (body weight) to about 10 mg/kg (e.g., 3, 4, 5, 6, 7, 8, 9 or 10 mg/kg) per day. In an embodiment, a "therapeutically effective dosage" of a chemotherapeutic agent is as set forth in the *Physicians' Desk Reference* 2003 (Thomson Healthcare; 57$^{th}$ edition (Nov. 1, 2002)) which is herein incorporated by reference. For example, in an embodiment, the daily dose of gefitinib is about 250 mg/day or the daily dose of paclitaxel is about 135 mg/m$^2$ to about 175 mg/m$^2$.

Therapeutic Methods and Administration

A combination of the invention or an anti-IGFR antibody or antigen-binding fragment thereof of the invention, alone, can be used to inhibit or reduce the growth or proliferation of any cell, such as a malignant cell, either in vitro (e.g., in cell culture) or in vivo (e.g., within the body of a subject suffering from a disease mediated by elevated expression or activity of IGFR1 or by elevated expression of its ligand (e.g., IGF-I or IGF-II)). Such inhibition or reduction of growth or proliferation of a cell can be achieved by contacting the cell with the combination.

A combination of the invention or an anti-IGFR antibody or antigen-binding fragment thereof, alone, of the invention can be used for treating or preventing any disease or condition in a subject in need of such treatment or prevention which is mediated, for example, by elevated expression or activity of IGFR1 or by elevated expression of its ligand (e.g., IGF-I or IGF-II) and which may be treated or prevented by modulation of IGFR1 ligand binding, activity or expression. Preferably, the disease or condition is mediated by an increased level of IGFR1, IGF-I or IGF-II and is treated or prevented by decreasing IGFR1 ligand binding, activity (e.g., autophosphorylation activity) or expression. Preferably, the disease or condition is malignancy, more preferably a malignancy characterized by a tumor which expresses IGFR1, such as, but not limited to, bladder cancer, Wilm's cancer, bone cancer, prostate cancer, lung cancer, colorectal cancer, breast cancer, cervical cancer, synovial sarcoma, ovarian cancer, pancreatic cancer, benign prostatic hyperplasia (BPH), diarrhea associated with metastatic carcinoid and vasoactive intestinal peptide secreting tumors (e.g., VIPoma or Werner-Morrison syndrome). Acromegaly may also be treated with a combination of the invention. Antagonism of IGF-I has been reported for treatment of acromegaly (Drake, et al., (2001) Trends Endocrin. Metab. 12: 408-413). Other non-malignant medical conditions which may also be treated, in a subject, by administering a combination of the invention, include gigantism, psoriasis, atherosclerosis, smooth muscle restenosis of blood vessels or inappropriate microvascular proliferation, such as that found as a complication of diabetes, especially of the eye rheumatoid arthritis, Grave's disease, multiple sclerosis, systemic lupus erythematosus, Hashimoto's Thyroiditis, Myasthenia Gravis, auto-immune thyroiditis and Bechet's disease.

The term "subject" may refer to any organism, preferably an animal, more preferably a mammal (e.g., rat, mouse, dog, cat, rabbit) and most preferably a human.

In an embodiment of the invention, where possible, a composition of the invention is administered to a subject in accordance with the Physicians' Desk Reference 2003 (Thomson Healthcare; 57th edition (Nov. 1, 2002)).

A combination of the invention or any component thereof can be administered by an invasive route such as by injection (see above). Administration by a non-invasive route (e.g., orally; for example, in a pill, capsule or tablet) is also within the scope of the present invention. In an embodiment of the invention, an anti-IGFR antibody of the invention, or pharmaceutical composition thereof, is administered intravenously, subcutaneously, intramuscularly, intraarterially or intratumorally while a chemotherapeutic agent of the invention (e.g., gefitinib (e.g., Iressa™)) is administered orally in tablet form. In another embodiment, the chemotherapeutic agent is paclitaxel (e.g., Taxol®) which is administered intravenously.

Compositions can be administered with medical devices known in the art. For example, a pharmaceutical composition of the invention can be administered by injection with a hypodermic needle.

The pharmaceutical compositions of the invention may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

Examples of well-known implants and modules form administering pharmaceutical compositions include: U.S. Pat. No. 4,487,603, which discloses an implantable microinfusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Kits

The present invention also provides kits comprising the components of the combinations of the invention in kit form. A kit of the present invention includes one or more components including, but not limited to, a binding composition, as discussed herein, which specifically binds IGFR1 (e.g., 19D12/15H12 LCF/HCA) in association with one or more additional components including, but not limited to, a chemotherapeutic agent, as discussed herein. The binding composition and/or the chemotherapeutic agent can be formulated as a pure composition or in combination with a pharmaceutically acceptable carrier, in a pharmaceutical composition.

In one embodiment, a kit includes a binding composition of the invention (e.g., 19D12/15H12 LCF/HCA) or a pharmaceutical composition thereof in one container (e.g., in a sterile glass or plastic vial) and a chemotherapeutic agent or a pharmaceutical composition thereof in another container (e.g., in a sterile glass or plastic vial).

In another embodiment of the invention, the kit comprises a combination of the invention, including a binding composition component (e.g., 19D12/15H12 LCF/HCA) along with a chemotherapeutic agent component formulated together, optionally, along with a pharmaceutically acceptable carrier, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

EXAMPLES

The following examples are provided to further describe the present invention and should not be construed to limit the scope of the invention in any way.

Example 1

Proliferation Assay Using an Anti-IGFR1 Antibody and a Chemotherapeutic Agent

The ability of cells in culture to proliferate when exposed to varying concentrations of the 19D12/15H12 wild-type or 19D12/15H12 LCF/HCA anti-IGFR1 antibody and either paclitaxel, gefitinib, lonafarnib 4-hydroxy tamoxifen or doxorubicin was evaluated in this example.

Cell Preparation. H322 NSCLC cells or MCF7 cells were cultured for several passages no greater than 80% confluency in T-75 TC treated filtered flasks. The cells were trypsinized, counted and resuspended at a concentration of 25000 cells/ml in 10% HI-FBS (heat-inactivated fetal bovine serum) RPMI medium containing NEAA (non-essential amino acids), L-Glu, MEM Vitamins and PS. 100 ul of cell suspension (2500 cells) was added to each well of a BD Falcon 96 well black, clear bottom TC treated plate. The cells were allowed to attach and spread overnight at 37° C. The 10% RPMI solution was replaced with 100 µl RPMI containing 2% HI-FBS containing NEAA, L-Glu, MEM Vitamins and PS.

Solution Preparation. All assay reagents were prepared in RPMI containing 2% HI-FBS at 20× concentration and serial diluted for a total of 10 test concentrations per treatment. Every test point was prepared in triplicate on separate assay plates. Each plate included experimental wells containing either (i) antibody 19D12/15H12 and paclitaxel, (ii) antibody 19D12/15H12 and gefitinib; (iii) antibody 19D12/15H12 LCF/HCA and lonafarnib; (iv) antibody 19D12/15H12 and 4-hydroxy tamoxifen; or (v) antibody 19D12/15H12 and doxorubicin along with internal controls of containing either (a) no treatment, (b) reagent1 (paclitaxel, gefitinib, lonafarnib, 4-hydroxy tamoxifen or doxorubicin) alone, and (c) antibody 19D12/15H12 or 19D12/15H12 LCF/HCA alone.

Reagent 1 and 19D12/15H12 or 19D12/15H12 LCF/HCA were set up individually as dose responses as well as in combination with each other. Cell proliferation was measured on Day4.

Assay. Cell proliferation was measured using the Promega Cell Titer-Glo Luminescent Cell Viability Assay (Promega Corp.; Madison, Wis.). This assay provided a method for determining the number of viable cells in culture based on quantitation of ATP in the culture, which indicates the presence of metabolically active cells.

The assay reagents and assay plates were equilibrated to room temperature and prepared immediately before addition to the assay plates. One volume of assay reagent was added to each well of the assay plate and shaken on an orbital platform for at least ten minutes to allow for equilibration of the ATP reaction and to ensure total lysis of all cells in the assay plate. The reaction had a half-life of five hours but in no case was reading done later than 30 minutes after addition of reagent. Luminescence was detected on Wallac 420 Plate Reader with stacker.

The results from these experiments are shown below in Tables 2-6. The units in the tables (proliferation index) are arbitrary and are proportional to the number of viable cells observed in the culture under each respective condition. The data from the "no treatment" experiments indicate the proliferation index observed in the absence of any drug (i.e., antibody or chemotherapeutic composition).

In Tables 2-6, "ug" indicates micrograms and "uM" indicates micromolar.

TABLE 2

Proliferation of H322 NSCLC cells in the presence of anti-IGFR1 antibody 19D12/15H12 and paclitaxel ("Taxol").

| | | Taxol (ng/ml) | | | | | | | | |
|---|---|---|---|---|---|---|---|---|---|---|
| | | 1000 | 200 | 40 | 8 | 1.6 | 0.32 | 0.064 | 0.0128 | 0.00256 | 0.000512 |
| Antibody 19D12/ 15H12 LCF/ HCA (nM) | 20 | 14882 | 14938 | 16272 | 23966 | 47176 | 54106 | 52266 | 50238 | 48568 | 52820 |
| | 4 | 15794 | 16310 | 15258 | 21956 | 41402 | 48226 | 51580 | 49332 | 48232 | 48314 |
| | 0.8 | 17792 | 16948 | 14676 | 23486 | 41838 | 52140 | 51214 | 49554 | 53374 | 52252 |
| | 0.16 | 18754 | 16032 | 16674 | 23634 | 46632 | 49704 | 54068 | 53728 | 55428 | 54010 |
| | 0.032 | 17468 | 16782 | 14752 | 29406 | 51924 | 59734 | 53824 | 58734 | 58048 | 60032 |
| | 0.0064 | 19056 | 19060 | 18210 | 27712 | 53038 | 60690 | 70632 | 63172 | 60680 | 66862 |
| | 0.00128 | 19952 | 20250 | 20094 | 34790 | 61030 | 68190 | 71192 | 69036 | 62998 | 71744 |
| | 0.000256 | 20876 | 20890 | 20222 | 35418 | 58662 | 68950 | 64984 | 68884 | 71162 | 72808 |
| | 5.12E−05 | 22304 | 21462 | 23232 | 46896 | 80714 | 77044 | 79658 | 73562 | 80006 | 84546 |
| | 1.02E−05 | 25400 | 23894 | 22898 | 44032 | 74546 | 77406 | 75958 | 78316 | 79680 | 82824 |

| | | Taxol (ng/ml) | | | | | | | | |
|---|---|---|---|---|---|---|---|---|---|---|
| | | 1000 | 200 | 40 | 8 | 1.6 | 0.32 | 0.064 | 0.0128 | 0.00256 | 0.000512 |
| Antibody 19D12/ 15H12 LCF/ HCA (nM) | 20 | 14870 | 15094 | 15452 | 25194 | 40292 | 46498 | 45024 | 50218 | 51442 | 53750 |
| | 4 | 16516 | 15038 | 15492 | 22860 | 39982 | 45616 | 46408 | 44896 | 50612 | 50264 |
| | 0.8 | 14796 | 14110 | 14022 | 21984 | 44652 | 47520 | 47290 | 46848 | 47332 | 50384 |
| | 0.16 | 16538 | 14428 | 14312 | 22256 | 41856 | 52060 | 52938 | 54362 | 51564 | 49882 |
| | 0.032 | 17974 | 17616 | 16878 | 27580 | 51068 | 55700 | 63276 | 55798 | 58766 | 64396 |
| | 0.0064 | 21998 | 18662 | 18658 | 30754 | 56400 | 65974 | 72874 | 70878 | 72164 | 70396 |
| | 0.00126 | 23030 | 20380 | 20806 | 32318 | 61380 | 75388 | 73794 | 72076 | 72602 | 74058 |
| | 0.000256 | 22758 | 19894 | 21232 | 34232 | 61662 | 76538 | 71674 | 72876 | 76362 | 80456 |
| | 5.12E−05 | 21702 | 22424 | 22344 | 39384 | 67066 | 66364 | 74268 | 72708 | 73390 | 77974 |
| | 1.02E−05 | 23622 | 22234 | 21764 | 38960 | 68346 | 70906 | 71034 | 74208 | 73766 | 75186 |

| | | Taxol (ng/ml) | | | | | | | | |
|---|---|---|---|---|---|---|---|---|---|---|
| | | 1000 | 200 | 40 | 8 | 1.6 | 0.32 | 0.064 | 0.0128 | 0.00256 | 0.000512 |
| Antibody 19D12/ 15H12 LCF/ HCA (nM) | 20 | 15934 | 14704 | 13960 | 23694 | 41142 | 44472 | 48242 | 48976 | 46244 | 48044 |
| | 4 | 15416 | 15464 | 15508 | 21644 | 37994 | 45112 | 43838 | 48690 | 49494 | 51944 |
| | 0.8 | 14844 | 14994 | 15916 | 21136 | 37026 | 48134 | 48824 | 47710 | 48656 | 48484 |
| | 0.16 | 16782 | 16786 | 15532 | 23870 | 43976 | 49102 | 49568 | 51606 | 52426 | 51598 |
| | 0.032 | 19140 | 18150 | 17670 | 27456 | 55260 | 61668 | 65654 | 65422 | 60994 | 59536 |
| | 0.0064 | 22596 | 20462 | 20124 | 29964 | 57072 | 76988 | 71298 | 74152 | 69218 | 68814 |
| | 0.00128 | 23930 | 21322 | 23648 | 33882 | 62218 | 73942 | 76080 | 79882 | 76866 | 78952 |
| | 0.000256 | 24970 | 21794 | 22122 | 33882 | 62980 | 83316 | 80868 | 86064 | 77932 | 75714 |
| | 5.12E−05 | 21220 | 19870 | 20890 | 36634 | 66106 | 74250 | 79392 | 72524 | 68150 | 69686 |
| | 1.02E−05 | 21408 | 21356 | 20574 | 37962 | 68052 | 67564 | 73422 | 72328 | 74388 | 72110 |
| Antibody 19D12/ 15H12 LCF/ HCA (nM) | 20 | 55106 | 50680 | 49038 | 56114 | 52446 | 51826 | 52490 | 48302 | 44120 | |
| | 4 | 48884 | 49992 | 50508 | 47256 | 56998 | 54966 | 51438 | 44700 | 42312 | |
| | 0.8 | 47470 | 52010 | 49636 | 55228 | 53706 | 56984 | 49396 | 47080 | 40944 | |
| | 0.16 | 59594 | 52620 | 53196 | 55122 | 53138 | 58778 | 50902 | 49702 | 51550 | |
| | 0.032 | 57110 | 60794 | 60018 | 58422 | 59506 | 65230 | 63764 | 61432 | 59276 | |
| | 0.0064 | 79014 | 72998 | 69060 | 64818 | 74862 | 76374 | 68206 | 70226 | 61654 | |
| | 0.00128 | 77870 | 78502 | 70644 | 72430 | 75326 | 82604 | 84198 | 72520 | 77014 | |
| | 0.000256 | 74154 | 83338 | 74108 | 84234 | 83206 | 80894 | 82674 | 71784 | 73420 | |
| | 5.12E−05 | 87030 | 83636 | 79810 | 79650 | 90294 | 88940 | 86762 | 74996 | 74408 | |
| Taxol (ng/mL) | 1000 | 26882 | 24582 | 23884 | 23712 | 25890 | 24522 | 24842 | 20306 | 20932 | |
| | 200 | 23650 | 23668 | 23164 | 23482 | 24314 | 25752 | 23960 | 21420 | 19372 | |

TABLE 2-continued

Proliferation of H322 NSCLC cells in the presence of anti-IGFR1 antibody 19D12/15H12 and paclitaxel ("Taxol").

| | | | | | | | | | |
|---|---|---|---|---|---|---|---|---|---|
| 40 | 25204 | 22624 | 22020 | 22956 | 24152 | 23908 | 24834 | 22462 | 22160 |
| 8 | 33654 | 34598 | 31556 | 36038 | 35906 | 34498 | 53256 | 41418 | 38354 |
| 1.6 | 61430 | 55962 | 58780 | 65654 | 61946 | 65024 | 72552 | 65054 | 65508 |
| 0.32 | 73668 | 75506 | 79886 | 73002 | 77072 | 76356 | 87640 | 68504 | 72500 |
| 0.064 | 83082 | 74926 | 73584 | 75710 | 75356 | 87602 | 75690 | 76350 | 75374 |
| 0.0128 | 78312 | 80172 | 71110 | 68078 | 73092 | 81374 | 80916 | 76870 | 75698 |
| 0.00256 | 78070 | 89290 | 71662 | 72122 | 77618 | 81720 | 80172 | 76744 | 72498 |

No treatment: 71974; 81788; 75410; 75124; 75558; 79618; 77860; 83468; 78992; 79840; 85414; 87962; 84304; 88926; 77074; 86696; 74354; 77454.

TABLE 3

Proliferation of H322 NSCLC cells in the presence of anti-IGFR1 antibody 19D12/15H12 and gefitinib ("Iressa").

| | | Iressa (nM) | | | | | | | | |
|---|---|---|---|---|---|---|---|---|---|---|
| | | 20000 | 4000 | 800 | 160 | 32 | 6.4 | 1.28 | 0.256 | 0.0512 | 0.01024 |
| Antibody 19D12/ | 20 | 9558 | 15828 | 19268 | 21734 | 31862 | 41596 | 47762 | 52134 | 56984 | 61128 |
| 15H12 LCF/ | 4 | 10376 | 16138 | 20236 | 24352 | 33156 | 41640 | 49994 | 54620 | 54206 | 62870 |
| HCA (nM) | 0.8 | 10116 | 16046 | 19810 | 23668 | 35062 | 46258 | 50218 | 49612 | 53604 | 60098 |
| | 0.16 | 8992 | 15922 | 22342 | 28574 | 35768 | 51788 | 56192 | 58236 | 59784 | 69564 |
| | 0.032 | 10384 | 20756 | 22894 | 26754 | 34428 | 41682 | 47362 | 49520 | 46866 | 60414 |
| | 0.0064 | 9272 | 23412 | 27042 | 29930 | 41028 | 48906 | 52394 | 58162 | 55702 | 65872 |
| | 0.00128 | 11306 | 26638 | 31304 | 33550 | 46588 | 55014 | 56990 | 56936 | 59854 | 74452 |
| | 0.000256 | 11030 | 25926 | 31678 | 33980 | 41866 | 55438 | 55030 | 55860 | 55694 | 76588 |
| | 5.12E−05 | 11312 | 25776 | 32168 | 34046 | 50366 | 59746 | 61846 | 56170 | 61912 | 77856 |
| | 1.02E−05 | 11468 | 25536 | 31772 | 33518 | 43818 | 59198 | 56520 | 60394 | 62178 | 75432 |

| | | Iressa (nM) | | | | | | | | |
|---|---|---|---|---|---|---|---|---|---|---|
| | | 20000 | 4000 | 800 | 160 | 32 | 6.4 | 1.28 | 0.256 | 0.0512 | 0.01024 |
| Antibody 19D12/ | 20 | 10256 | 14646 | 19414 | 20748 | 26104 | 29688 | 36636 | 34068 | 38386 | 44984 |
| 15H12 LCF/ | 4 | 7434 | 13982 | 18762 | 20558 | 23708 | 31514 | 33878 | 38178 | 38814 | 43776 |
| HCA (nM) | 0.8 | 9450 | 15536 | 17874 | 20264 | 26830 | 37782 | 35146 | 37854 | 38790 | 48940 |
| | 0.16 | 8216 | 16648 | 20086 | 21762 | 27672 | 35674 | 37692 | 38746 | 43660 | 50204 |
| | 0.032 | 10600 | 20332 | 24214 | 26092 | 37170 | 43970 | 45010 | 47656 | 50738 | 58834 |
| | 0.0064 | 9472 | 23840 | 27740 | 31758 | 43494 | 49736 | 52676 | 53360 | 56270 | 69508 |
| | 0.00128 | 10994 | 25884 | 30786 | 35254 | 46102 | 51856 | 57484 | 53240 | 58572 | 74556 |
| | 0.000256 | 11074 | 25614 | 30444 | 34546 | 44880 | 53284 | 57562 | 56742 | 59694 | 70748 |
| | 5.12E−05 | 10856 | 26726 | 32516 | 33914 | 45230 | 53468 | 59308 | 58268 | 61842 | 74782 |
| | 1.02E−05 | 12316 | 27228 | 32274 | 36732 | 44376 | 55024 | 57706 | 58968 | 69576 | 77220 |

| | | Iressa (nM) | | | | | | | | |
|---|---|---|---|---|---|---|---|---|---|---|
| | | 20000 | 4000 | 800 | 160 | 32 | 6.4 | 1.28 | 0.256 | 0.0512 | 0.01024 |
| Antibody 19D12/ | 20 | 8794 | 15734 | 18284 | 20542 | 27156 | 36040 | 36982 | 36560 | 40968 | 48488 |
| 15H12 LCF/ | 4 | 7278 | 14032 | 18810 | 20758 | 23414 | 32396 | 33706 | 33882 | 35690 | 46774 |
| HCA (nM) | 0.8 | 10144 | 15324 | 18636 | 21026 | 27062 | 33876 | 37008 | 37674 | 40920 | 45608 |
| | 0.16 | 8448 | 15310 | 19562 | 22450 | 26856 | 34532 | 37372 | 39045 | 40020 | 49212 |
| | 0.032 | 9564 | 19962 | 23658 | 26014 | 31138 | 45406 | 48394 | 50528 | 48256 | 60600 |
| | 0.0064 | 9654 | 22866 | 26700 | 30792 | 39610 | 46272 | 55464 | 53168 | 55588 | 67954 |
| | 0.00128 | 10748 | 26120 | 28034 | 32110 | 42170 | 50768 | 59264 | 56428 | 60524 | 70960 |
| | 0.000256 | 11152 | 26246 | 29536 | 34822 | 42410 | 51262 | 59646 | 56492 | 67308 | 74614 |
| | 5.12E−05 | 13086 | 26320 | 29186 | 35546 | 40932 | 56044 | 61442 | 57668 | 60428 | 69352 |
| | 1.02E−05 | 10894 | 27054 | 32100 | 34678 | 44726 | 52768 | 62750 | 60398 | 65932 | 73544 |
| Antibody 19D12/ | 20 | 58598 | 48444 | 49156 | 51020 | 48730 | 49684 | 45064 | 52120 | 51960 | |
| 15H12 LCF/ | 4 | 63472 | 47736 | 49492 | 49964 | 49606 | 52660 | 49972 | 50764 | 49330 | |
| HCA (nM) | 0.8 | 65622 | 50708 | 49752 | 49306 | 49694 | 52460 | 50044 | 48780 | 49206 | |
| | 0.16 | 67002 | 51304 | 53266 | 49398 | 50474 | 53774 | 52510 | 48004 | 49650 | |
| | 0.032 | 82944 | 58364 | 59636 | 64806 | 60990 | 58984 | 56958 | 60178 | 53730 | |
| | 0.0064 | 100862 | 69248 | 72446 | 68396 | 66834 | 73768 | 73208 | 70772 | 66560 | |
| | 0.00128 | 102034 | 78940 | 72448 | 73608 | 73492 | 75502 | 83358 | 79498 | 77492 | |
| | 0.000256 | 107482 | 77972 | 78152 | 76908 | 80874 | 79674 | 69202 | 80170 | 78292 | |
| | 5.12E−05 | 102770 | 79860 | 81938 | 84040 | 79398 | 83148 | 81960 | 78368 | 81372 | |
| Iressa (nM) | 20000 | 10818 | 11294 | 10994 | 11770 | 11460 | 9734 | 12088 | 11650 | 12396 | |
| | 4000 | 27810 | 24546 | 24376 | 26742 | 28156 | 24528 | 28442 | 27026 | 27738 | |
| | 800 | 40002 | 31290 | 30354 | 31800 | 31390 | 30998 | 32232 | 31356 | 32328 | |
| | 160 | 43832 | 32072 | 32728 | 33532 | 35078 | 34864 | 36144 | 34946 | 35044 | |

TABLE 3-continued

Proliferation of H322 NSCLC cells in the presence of anti-IGFR1 antibody 19D12/15H12 and gefitinib ("Iressa").

| | | | | | | | | | |
|---|---|---|---|---|---|---|---|---|---|
| 32 | 58272 | 41264 | 40992 | 44162 | 42054 | 43124 | 45062 | 41426 | 45712 |
| 6.4 | 71582 | 52692 | 49154 | 50752 | 50888 | 52698 | 52362 | 59384 | 53484 |
| 1.28 | 79748 | 57670 | 51772 | 58016 | 57048 | 62268 | 57264 | 57770 | 60032 |
| 0.256 | 73246 | 58760 | 59474 | 57314 | 58384 | 59448 | 66806 | 64854 | 56752 |
| 0.0512 | 76032 | 61018 | 59690 | 63252 | 63688 | 60730 | 74464 | 65802 | 59448 |

No treatment: 107584; 107042; 73770; 80360; 80730; 83682; 82196; 81768; 76594; 74958; 78190; 83348; 81032; 78026; 81010; 81632; 72058; 74778.

TABLE 4

Proliferation of H322 NSCLC cells in the presence of anti-IGFR1 antibody 19D12 (LCF/HCA) and Ionafarnib.

| | | Ionafarnib (uM) | | | | | | | | |
|---|---|---|---|---|---|---|---|---|---|---|
| | | 10 | 2 | 0.4 | 0.08 | 0.016 | 0.0032 | 0.00064 | 0.000128 | 2.56E−05 | 5.12E−06 |
| Antibody 19D12/ 15H12 LCF/ HCA (nM) | 20 | 22887 | 65425 | 80588 | 83638 | 90851 | 93313 | 88977 | 84231 | 86387 | 94181 |
| | 4 | 16249 | 64289 | 74003 | 87732 | 90544 | 93698 | 86567 | 83618 | 89257 | 94255 |
| | 0.8 | 16422 | 65033 | 81211 | 88566 | 93368 | 94731 | 90121 | 85926 | 89908 | 93068 |
| | 0.16 | 19691 | 74212 | 79370 | 95207 | 94682 | 92386 | 95905 | 89859 | 87593 | 92957 |
| | 0.032 | 32664 | 95526 | 106781 | 109768 | 119933 | 124460 | 124138 | 119869 | 119709 | 112287 |
| | 0.0064 | 36016 | 117821 | 125523 | 136608 | 134282 | 142279 | 138637 | 132253 | 134387 | 131094 |
| | 0.00128 | 18089 | 117945 | 129629 | 143264 | 148075 | 146870 | 144201 | 144368 | 146965 | 141886 |
| | 0.000256 | 47214 | 122431 | 126687 | 142050 | 145968 | 147044 | 145114 | 148567 | 139090 | 140391 |
| | 5.12E−05 | 37457 | 126574 | 125493 | 146377 | 141190 | 143914 | 145795 | 146753 | 141184 | 147030 |
| | 1.02E−05 | 33216 | 127909 | 123776 | 134604 | 140889 | 142610 | 142138 | 147417 | 145893 | 143802 |

| | | Ionafarnib (uM) | | | | | | | | |
|---|---|---|---|---|---|---|---|---|---|---|
| | | 10 | 2 | 0.4 | 0.08 | 0.016 | 0.0032 | 0.00064 | 0.000128 | 2.56E−05 | 5.12E−06 |
| Antibody 19D12/ 15H12 LCF/ HCA (nM) | 20 | 25599 | 81353 | 94441 | 102269 | 105276 | 104847 | 101476 | 101812 | 95178 | 106063 |
| | 4 | 20764 | 77690 | 90928 | 106880 | 107326 | 99982 | 107648 | 101840 | 100814 | 103761 |
| | 0.8 | 20754 | 82864 | 94954 | 99767 | 103085 | 105548 | 104157 | 105083 | 102191 | 105169 |
| | 0.16 | 31796 | 83859 | 99944 | 102713 | 114195 | 115366 | 102845 | 109980 | 105072 | 108221 |
| | 0.032 | 21337 | 96495 | 106094 | 121189 | 125248 | 129724 | 125146 | 116621 | 122758 | 118644 |
| | 0.0064 | 36668 | 111937 | 118924 | 136466 | 140637 | 139477 | 139912 | 144443 | 138247 | 144052 |
| | 0.00128 | 21924 | 123895 | 132128 | 143031 | 141540 | 143420 | 151166 | 150090 | 144396 | 144645 |
| | 0.000256 | 48311 | 125873 | 132897 | 145890 | 151220 | 144128 | 142869 | 149502 | 143318 | 136823 |
| | 5.12E−05 | 48664 | 119468 | 129321 | 133949 | 138336 | 139465 | 141690 | 140419 | 144102 | 144108 |
| | 1.02E−05 | 43562 | 118319 | 121877 | 131702 | 143683 | 141602 | 138419 | 169559 | 135173 | 144663 |

| | | Ionafarnib (uM) | | | | | | | | |
|---|---|---|---|---|---|---|---|---|---|---|
| | | 10 | 2 | 0.4 | 0.08 | 0.016 | 0.0032 | 0.00064 | 0.000128 | 2.56E−05 | 5.12E−06 |
| Antibody 19D12/ 15H12 LCF/ HCA (nM) | 20 | 25332 | 79142 | 87710 | 99399 | 105519 | 104613 | 95139 | 98673 | 102026 | 107719 |
| | 4 | 18060 | 75938 | 90974 | 93891 | 102015 | 108253 | 99835 | 98861 | 98297 | 100571 |
| | 0.8 | 19703 | 82941 | 88791 | 105006 | 101589 | 107751 | 104522 | 98935 | 97246 | 104178 |
| | 0.16 | 23130 | 80072 | 91005 | 103752 | 112789 | 106256 | 105474 | 102482 | 101809 | 99297 |
| | 0.032 | 31869 | 101343 | 104850 | 116040 | 118774 | 124757 | 128139 | 123353 | 119392 | 120241 |
| | 0.0064 | 28099 | 117822 | 116943 | 134107 | 139079 | 142540 | 142884 | 131445 | 140203 | 134047 |
| | 0.00128 | 26945 | 122121 | 127278 | 138720 | 139301 | 143652 | 146461 | 141979 | 146123 | 148973 |
| | 0.000256 | 35661 | 135020 | 125671 | 138311 | 137575 | 151958 | 143929 | 145060 | 144944 | 142950 |
| | 5.12E−05 | 71640 | 116076 | 126056 | 138805 | 150323 | 149387 | 141235 | 142107 | 148337 | 135959 |
| | 1.02E−05 | 23393 | 121266 | 126158 | 139946 | 146882 | 142668 | 155099 | 151232 | 153079 | 145366 |
| Ionafarnib (uM) | 10 | 19478 | 10458 | 23206 | 21356 | 20500 | 30885 | 22728 | 33558 | 37475 | |
| | 2 | 96039 | 114766 | 108395 | 126290 | 125120 | 125480 | 128736 | 125728 | 117942 | |
| | 0.4 | 96566 | 116350 | 110889 | 126539 | 129131 | 132824 | 129715 | 123707 | 122379 | |
| | 0.08 | 111539 | 122519 | 121571 | 140084 | 136507 | 138641 | 141354 | 139918 | 139542 | |
| | 0.016 | 111904 | 129612 | 122694 | 138400 | 138169 | 143620 | 139541 | 145629 | 143004 | |
| | 0.0032 | 111185 | 124204 | 122392 | 141986 | 141129 | 142694 | 141727 | 141690 | 141938 | |
| | 0.00064 | 107175 | 127792 | 118530 | 144611 | 147139 | 146830 | 142720 | 138984 | 149101 | |
| | 0.000128 | 111619 | 118044 | 128736 | 146048 | 143127 | 143930 | 139172 | 142366 | 142624 | |
| | 2.56E−05 | 108451 | 129321 | 121819 | 140423 | 140297 | 145549 | 137649 | 138705 | 139746 | |

TABLE 4-continued

Proliferation of H322 NSCLC cells in the presence of anti-IGFR1 antibody 19D12 (LCF/HCA) and Ionafarnib.

| Antibody 19D12/ | 20 | 87222 | 99589 | 92548 | 112756 | 116485 | 112681 | 111436 | 116765 | 115599 |
|---|---|---|---|---|---|---|---|---|---|---|
| 15H12 LCF/ | 4 | 86973 | 95263 | 99359 | 113069 | 111989 | 115427 | 116657 | 111269 | 111380 |
| HCA (nM) | 0.8 | 87686 | 108909 | 106820 | 117584 | 116744 | 115624 | 122158 | 109225 | 107476 |
| | 0.16 | 88076 | 100801 | 103264 | 113402 | 119792 | 114893 | 111254 | 109486 | 119384 |
| | 0.032 | 101173 | 112575 | 111087 | 121525 | 126829 | 119236 | 120476 | 119619 | 127491 |
| | 0.0064 | 103393 | 122551 | 126487 | 135788 | 130783 | 132775 | 133999 | 136391 | 130520 |
| | 0.00128 | 111788 | 124573 | 128587 | 141883 | 148061 | 133429 | 135943 | 136842 | 134429 |
| | 0.000256 | 109876 | 126163 | 120456 | 139750 | 141149 | 139314 | 143089 | 138327 | 140445 |
| | 5.12E−05 | 110351 | 127505 | 122680 | 139271 | 142088 | 141457 | 143808 | 138240 | 138655 |

No treatment: 114280; 118325; 135058; 129246; 125513; 119709; 134363; 129286; 138048; 132272; 138562; 134026; 135510; 138660; 132918; 131451; 140071; 135689.

TABLE 5

Proliferation of MCF7 cells in the presence of anti-IGFR1 antibody 19D12/15H12 and 4-hydroxy tamoxifen.

| | | 4-hydroxy tamoxifen (ng/mL) | | | | | | | | | |
|---|---|---|---|---|---|---|---|---|---|---|---|
| | | 20000 | 4000 | 800 | 160 | 32 | 6.4 | 1.28 | 0.256 | 0.0512 | 0.01024 |
| Antibody 19D12/ | 20 | 37 | 3971 | 11406 | 10724 | 13431 | 12677 | 15154 | 17939 | 15882 | 17897 |
| 15H12 (nM) | 4 | 40 | 5820 | 12508 | 11400 | 13105 | 12500 | 15784 | 15310 | 19683 | 16670 |
| | 0.8 | 90 | 3445 | 10614 | 11280 | 13370 | 12744 | 12770 | 13406 | 15035 | 14492 |
| | 0.16 | 51 | 6002 | 12536 | 12269 | 13555 | 13668 | 17314 | 19078 | 17106 | 20470 |
| | 0.032 | 104 | 6110 | 15449 | 18373 | 17595 | 19182 | 22139 | 22556 | 24439 | 19180 |
| | 0.0064 | 72 | 7757 | 16479 | 17958 | 19548 | 21212 | 24801 | 23112 | 22358 | 22710 |
| | 0.00128 | 87 | 9202 | 21565 | 23021 | 22216 | 24256 | 26412 | 27233 | 26660 | 23187 |
| | 0.000256 | 47 | 7471 | 22532 | 23278 | 23323 | 20944 | 23987 | 23894 | 25353 | 22543 |
| | 5.12E−05 | 127 | 13158 | 23026 | 24274 | 24764 | 27845 | 28599 | 30546 | 35993 | 27680 |
| | 1.02E−05 | 88 | 13436 | 22449 | 21505 | 26558 | 27224 | 29026 | 27441 | 31739 | 31126 |

| | | 4-hydroxy tamoxifen (ng/mL) | | | | | | | | | |
|---|---|---|---|---|---|---|---|---|---|---|---|
| | | 20000 | 4000 | 800 | 160 | 32 | 6.4 | 1.28 | 0.256 | 0.0512 | 0.01024 |
| Antibody 19D12/ | 20 | 69 | 4768 | 12296 | 11697 | 12617 | 12755 | 14998 | 17332 | 16589 | 18942 |
| 15H12 (nM) | 4 | 49 | 4595 | 11159 | 12899 | 11551 | 12734 | 14254 | 15878 | 16453 | 20904 |
| | 0.8 | 49 | 4017 | 12152 | 12777 | 12363 | 12382 | 15072 | 15739 | 16814 | 16040 |
| | 0.16 | 62 | 3822 | 13820 | 12807 | 14116 | 13295 | 16653 | 17297 | 17190 | 18994 |
| | 0.032 | 49 | 8312 | 13771 | 15161 | 15330 | 15502 | 20027 | 20729 | 24916 | 24574 |
| | 0.0064 | 58 | 4944 | 16301 | 16891 | 19000 | 18186 | 24664 | 21450 | 26585 | 25930 |
| | 0.00128 | 67 | 7995 | 18252 | 20001 | 20433 | 22047 | 24749 | 26553 | 24061 | 28200 |
| | 0.000256 | 44 | 6257 | 18603 | 20299 | 20694 | 19361 | 22858 | 29561 | 23383 | 23704 |
| | 5.12E−05 | 155 | 12478 | 21685 | 24086 | 21627 | 26539 | 28497 | 28032 | 31389 | 28292 |
| | 1.02E−05 | 71 | 10442 | 21337 | 18711 | 24075 | 28872 | 25823 | 27243 | 25855 | 26935 |

| | | 4-hydroxy tamoxifen (ng/mL) | | | | | | | | | |
|---|---|---|---|---|---|---|---|---|---|---|---|
| | | 20000 | 4000 | 800 | 160 | 32 | 6.4 | 1.28 | 0.256 | 0.0512 | 0.01024 |
| Antibody 19D12/ | 20 | 44 | 6281 | 12450 | 12452 | 13478 | 13461 | 15254 | 16050 | 14565 | 16484 |
| 15H12 (nM) | 4 | 32 | 5475 | 10949 | 11943 | 12893 | 11816 | 11994 | 13359 | 13330 | 14821 |
| | 0.8 | 38 | 6446 | 11217 | 13440 | 11887 | 11298 | 13401 | 13307 | 14435 | 15783 |
| | 0.16 | 48 | 7402 | 12566 | 12977 | 14859 | 12918 | 14487 | 13272 | 13248 | 12716 |
| | 0.032 | 44 | 7046 | 13296 | 16558 | 16698 | 14963 | 17395 | 19170 | 21511 | 21430 |
| | 0.0064 | 38 | 9971 | 17183 | 18826 | 18601 | 20504 | 19703 | 21629 | 22131 | 25221 |
| | 0.00128 | 57 | 6826 | 18767 | 18169 | 21005 | 19872 | 20956 | 25526 | 26582 | 24174 |
| | 0.000256 | 47 | 10322 | 19159 | 20185 | 21625 | 22398 | 23918 | 24209 | 24674 | 25993 |
| | 5.12E−05 | 48 | 10014 | 21261 | 22537 | 24130 | 22183 | 28348 | 33891 | 30651 | 36185 |
| | 1.02E−05 | 42 | 8701 | 18262 | 20578 | 22339 | 24187 | 24942 | 26658 | 30301 | 24115 |
| Antibody 19D12/ | 20 | 23174 | 26202 | 29141 | 21364 | 18868 | 16137 | 21415 | 20969 | 20629 | |
| 15H12 (nM) | 4 | 23012 | 25311 | 22812 | 20994 | 20654 | 17723 | 21558 | 20516 | 22986 | |
| | 0.8 | 22225 | 27911 | 24915 | 19444 | 18812 | 19569 | 23960 | 18932 | 24136 | |
| | 0.16 | 28829 | 28863 | 24086 | 20817 | 16735 | 20162 | 20953 | 14080 | 19403 | |
| | 0.032 | 31483 | 33506 | 32253 | 30553 | 21667 | 22447 | 23620 | 20087 | 29483 | |
| | 0.0064 | 32335 | 38153 | 34750 | 28815 | 23405 | 29131 | 26092 | 21985 | 30515 | |
| | 0.00128 | 39949 | 35834 | 38745 | 36522 | 31998 | 25787 | 29872 | 28453 | 38665 | |
| | 0.000256 | 39149 | 38337 | 35944 | 38816 | 30209 | 28243 | 36082 | 34273 | 38595 | |
| | 5.12E−05 | 42680 | 42952 | 41634 | 39082 | 35487 | 31795 | 33137 | 30620 | 28960 | |

TABLE 5-continued

Proliferation of MCF7 cells in the presence of anti-IGFR1 antibody 19D12/15H12 and 4-hydroxy tamoxifen.

| 4-hydroxy tamoxifen (ng/mL) | | | | | | | | | | |
|---|---|---|---|---|---|---|---|---|---|---|
| | 20000 | 72 | 87 | 71 | 61 | 67 | 80 | 70 | 92 | 80 |
| | 4000 | 10306 | 14180 | 10772 | 10390 | 8819 | 8866 | 10856 | 7892 | 17190 |
| | 800 | 21328 | 22054 | 21091 | 21755 | 19455 | 16634 | 23295 | 18307 | 19893 |
| | 160 | 22497 | 24665 | 25001 | 19325 | 17700 | 21339 | 23979 | 17326 | 21462 |
| | 32 | 25519 | 27289 | 25493 | 19637 | 16366 | 23373 | 21391 | 15610 | 21213 |
| | 6.4 | 25230 | 30579 | 27858 | 23336 | 18772 | 23597 | 21593 | 16646 | 22699 |
| | 1.28 | 37809 | 36047 | 29501 | 36072 | 28249 | 30905 | 34689 | 24575 | 30878 |
| | 0.256 | 44922 | 43317 | 40504 | 41227 | 32889 | 40176 | 46899 | 40723 | 45399 |
| | 0.0512 | 45433 | 40809 | 36380 | 37799 | 32441 | 35438 | 40686 | 31466 | 38389 |

No treatment: 38094; 32799; 43225; 30131; 35545; 28400; 35256; 18441; 34641; 24138; 28849; 21562; 36446; 25365; 34561; 21852; 40120; 23587.

TABLE 6

Proliferation of MCF7 cells in the presence of anti-IGFR1 antibody 19D12/15H12 and doxorubicin.

| | | Doxorubicin (ug/mL) | | | | | | | | |
|---|---|---|---|---|---|---|---|---|---|---|
| | | 20 | 4 | 0.8 | 0.16 | 0.032 | 0.0064 | 0.00128 | 0.000256 | 0.0000512 | 0.00001024 |
| Antibody 19D12/ 15H12 (nM) | 20 | 9432 | 11571 | 4327 | 14770 | 28330 | 61105 | 67190 | 68057 | 63435 | 67065 |
| | 4 | 8464 | 11472 | 4480 | 15979 | 29169 | 52900 | 65198 | 60868 | 70110 | 61696 |
| | 0.8 | 7693 | 11778 | 4916 | 14649 | 25910 | 56538 | 55991 | 60055 | 64429 | 70307 |
| | 0.16 | 11139 | 13368 | 3876 | 17603 | 33070 | 57990 | 62871 | 57889 | 61711 | 72432 |
| | 0.032 | 8212 | 11386 | 4339 | 14678 | 24337 | 54110 | 65887 | 60388 | 61919 | 60165 |
| | 0.0064 | 7057 | 10648 | 4702 | 12467 | 25304 | 53583 | 59654 | 61820 | 60524 | 60936 |
| | 0.00128 | 9333 | 11985 | 4511 | 16285 | 30634 | 62212 | 65741 | 69427 | 68773 | 71351 |
| | 0.000256 | 6667 | 13174 | 5698 | 15544 | 30696 | 70725 | 78623 | 74312 | 76193 | 86861 |
| | 0.0000512 | 6793 | 11124 | 5649 | 17621 | 41883 | 93794 | 104241 | 107406 | 106322 | 111388 |
| | 0.00001024 | 7789 | 12606 | 5132 | 19799 | 41284 | 95276 | 94958 | 100293 | 102670 | 101144 |

| | | Doxorubicin (ug/mL) | | | | | | | | |
|---|---|---|---|---|---|---|---|---|---|---|
| | | 20 | 4 | 0.8 | 0.16 | 0.032 | 0.0064 | 0.00128 | 0.000256 | 0.0000512 | 0.00001024 |
| Antibody 19D12/ 15H12 (nM) | 20 | 7489 | 10465 | 5202 | 12812 | 27202 | 54983 | 61586 | 62242 | 60307 | 59288 |
| | 4 | 8097 | 12760 | 4259 | 13518 | 26907 | 53567 | 65049 | 58980 | 57611 | 61992 |
| | 0.8 | 7962 | 11444 | 4620 | 14232 | 25870 | 52978 | 55162 | 60064 | 55903 | 60959 |
| | 0.16 | 7156 | 11664 | 4656 | 14434 | 23880 | 51792 | 56145 | 62662 | 54446 | 63224 |
| | 0.032 | 7273 | 11715 | 3808 | 11653 | 25820 | 58726 | 58052 | 64869 | 67509 | 67042 |
| | 0.0064 | 9514 | 11880 | 4717 | 13751 | 26901 | 55417 | 69739 | 59483 | 61862 | 70864 |
| | 0.00128 | 7624 | 11335 | 5168 | 13974 | 30690 | 65877 | 76141 | 76721 | 72500 | 74819 |
| | 0.000256 | 6795 | 13841 | 5192 | 15665 | 34596 | 72686 | 87772 | 83443 | 87727 | 96162 |
| | 0.0000512 | 4987 | 10651 | 6383 | 16114 | 41787 | 87535 | 109774 | 95142 | 102950 | 101410 |
| | 0.00001024 | 7453 | 10964 | 5341 | 17070 | 36535 | 95801 | 102505 | 104135 | 98770 | 97354 |

| | | Doxorubicin (ug/mL) | | | | | | | | |
|---|---|---|---|---|---|---|---|---|---|---|
| | | 20 | 4 | 0.8 | 0.16 | 0.032 | 0.0064 | 0.00128 | 0.000256 | 0.0000512 | 0.00001024 |
| Antibody 19D12/ 15H12 (nM) | 20 | 6894 | 12254 | 4561 | 14187 | 26448 | 53574 | 60910 | 58429 | 57910 | 65793 |
| | 4 | 7759 | 12733 | 4690 | 13346 | 27239 | 48782 | 54506 | 56615 | 58519 | 58411 |
| | 0.8 | 8279 | 11409 | 5204 | 13692 | 27136 | 53208 | 57034 | 63312 | 56274 | 59071 |
| | 0.16 | 9293 | 11582 | 4477 | 13437 | 28068 | 52677 | 57275 | 56349 | 64286 | 63113 |
| | 0.032 | 7732 | 12239 | 4457 | 13470 | 26358 | 56485 | 67349 | 64682 | 63108 | 60620 |
| | 0.0064 | 7083 | 12668 | 4685 | 15548 | 25719 | 55245 | 67424 | 65321 | 61740 | 70000 |
| | 0.00128 | 7242 | 12016 | 5038 | 15836 | 32028 | 73071 | 75306 | 74244 | 81846 | 82028 |
| | 0.000256 | 7667 | 11912 | 4588 | 17698 | 33634 | 81304 | 90050 | 86458 | 82101 | 96123 |
| | 0.0000512 | 5540 | 13000 | 4993 | 16930 | 35578 | 81956 | 97435 | 90081 | 89891 | 90199 |
| | 0.00001024 | 8651 | 11441 | 5456 | 18082 | 41428 | 84266 | 104631 | 94107 | 88781 | 103628 |
| Antibody 19D12/ 15H12 (nM) | 20 | 68587 | 64953 | 54120 | 63607 | 61240 | 60441 | 72524 | 63214 | 56014 | |
| | 4 | 61918 | 62606 | 57447 | 59014 | 60339 | 64229 | 63861 | 58382 | 56115 | |
| | 0.8 | 65828 | 68830 | 59382 | 63472 | 59922 | 63881 | 58302 | 59377 | 60874 | |
| | 0.16 | 61026 | 60105 | 56597 | 61731 | 58445 | 62557 | 61735 | 60171 | 59635 | |
| | 0.032 | 65968 | 65014 | 53068 | 64005 | 60882 | 61339 | 67666 | 59746 | 55775 | |
| | 0.0064 | 70386 | 72436 | 59947 | 61008 | 59983 | 73428 | 86004 | 63957 | 66125 | |
| | 0.00128 | 87998 | 85396 | 72430 | 77794 | 70644 | 74742 | 85341 | 70972 | 75666 | |
| | 0.000256 | 98787 | 96373 | 87642 | 92406 | 91506 | 94941 | 96941 | 92043 | 98687 | |
| | 0.0000512 | 108894 | 108108 | 95976 | 101359 | 97684 | 96453 | 106595 | 104255 | 100190 | |

TABLE 6-continued

Proliferation of MCF7 cells in the presence of anti-IGFR1 antibody 19D12/15H12 and doxorubicin.

| Doxorubicin (ug/mL) | 20 | 9006 | 7776 | 9201 | 8561 | 9331 | 5986 | 11238 | 7007 | 8551 |
|---|---|---|---|---|---|---|---|---|---|---|
| | 4 | 13508 | 13215 | 14467 | 14796 | 15140 | 13720 | 14371 | 12706 | 13581 |
| | 0.8 | 7826 | 6924 | 6188 | 7517 | 6873 | 7476 | 7217 | 7509 | 7035 |
| | 0.16 | 18882 | 17682 | 19304 | 21187 | 20726 | 17219 | 24438 | 17565 | 17961 |
| | 0.032 | 42219 | 41877 | 43752 | 46250 | 44311 | 42710 | 47630 | 41075 | 42613 |
| | 0.0064 | 94502 | 95453 | 92157 | 94356 | 108010 | 99650 | 104886 | 96671 | 97741 |
| | 0.00128 | 118478 | 99555 | 109394 | 106089 | 117727 | 103222 | 107569 | 101631 | 101676 |
| | 0.000256 | 110655 | 99580 | 106279 | 113634 | 104912 | 108830 | 115394 | 102385 | 111217 |
| | 0.0000512 | 114729 | 100997 | 103267 | 109090 | 109582 | 120733 | 112898 | 108905 | 101765 |

No treatment: 126997; 128567; 116244; 117342; 112806; 114636; 122023; 117403; 121666; 112160; 123333; 118499; 117737; 120728; 115823; 128693; 124935; 126222.

Example 2

In Vivo Tumor Inhibition Assay of Anti-IGFR and Paclitaxel Using a NSCLC Xenograft Model H322

In this example, the effectiveness of an anti-IGFR/paclitaxel combination of the invention for tumor growth inhibition was demonstrated in vivo.

Five million H322 human NSCLC cells in Matrigel were inoculated subcutaneously into nude mice. Anti-IGFR antibody 19D12 and/or paclitaxel treatment was initiated when the tumor size reached ~105-115 mm$^3$ at day 0. Both 19D12 and paclitaxel were dosed twice per week. Anti-IGFR antibody 19D12 was dosed at 0.5 mg per mouse. Paclitaxel was at 15 mpk. Ten animals per group. Tumor volumes were measured by Labcat.

TABLE 7

Tumor growth inhibition in mice.

| | | Day 0 | 31 |
|---|---|---|---|
| Vehicle control | volume (mm3) | 112.68 | 383.70 |
| | SEM | 3.09 | 72.75 |
| | SD | 9.28 | 218.25 |
| | Growth | | 271.02 |

TABLE 7-continued

Tumor growth inhibition in mice.

| | | Day 0 | 31 |
|---|---|---|---|
| 0.5 mg 19D12 | volume (mm3) | 106.57 | 173.02 |
| | SEM | 1.96 | 38.63 |
| | SD | 5.87 | 115.89 |
| | Growth | | 66.45 |
| | % inhibition | | 75.50% |
| 15 mpk Taxol | volume (mm3) | 109.54 | 214.25 |
| | SEM | 2.9 | 27.94 |
| | SD | 8.7 | 83.81 |
| | Growth | | 104.71 |
| | % inhibition | | 52% |
| 0.5 mg 19D12 + 15 mpk Taxol | volume (mm3) | 109.79 | 121.92 |
| | SEM | 4.21 | 22.17 |
| | SD | 12.63 | 66.52 |
| | Growth | | 12.13 |
| | % inhibition | | 95.50% |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, Genbank Accession Numbers and publications are cited throughout this application, the disclosures of which, particularly, including all disclosed chemical structures and antibody amino acid sequences therein, are incorporated herein by reference.

We claim:
1. A composition comprising:
(a) one or more isolated antibodies or antigen-binding fragments thereof, that specifically bind human insulin-like growth factor receptor 1, comprising a light chain immunoglobulin amino acid sequence which comprises CDR-L1 comprising the amino acid sequence set forth in SEQ ID NO: 5, CDR-L2 comprising the amino acid sequence set forth in SEQ ID NO: 6 and CDR-L3 comprising the amino acid sequence set forth in SEQ ID NO: 7; and a heavy chain immunoglobulin amino acid sequence which comprises CDR-H1 comprising the amino acid sequence set forth in SEQ ID NO: 8 or 12, CDR-H2 comprising the amino acid sequence set forth in SEQ ID NO: 9 and CDR-H3 comprising the amino acid sequence set forth in SEQ ID NO: 10; in association with
(b) one or more chemotherapeutic agents selected from the group consisting of:
lonafarnib;

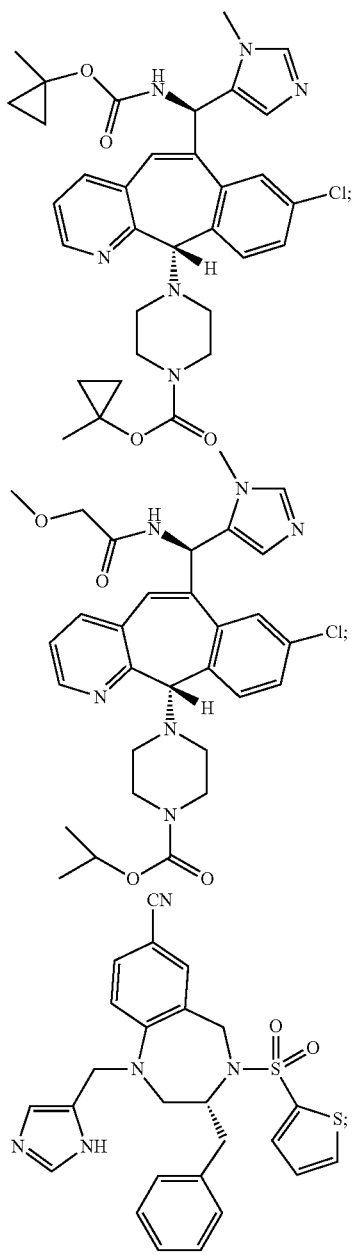

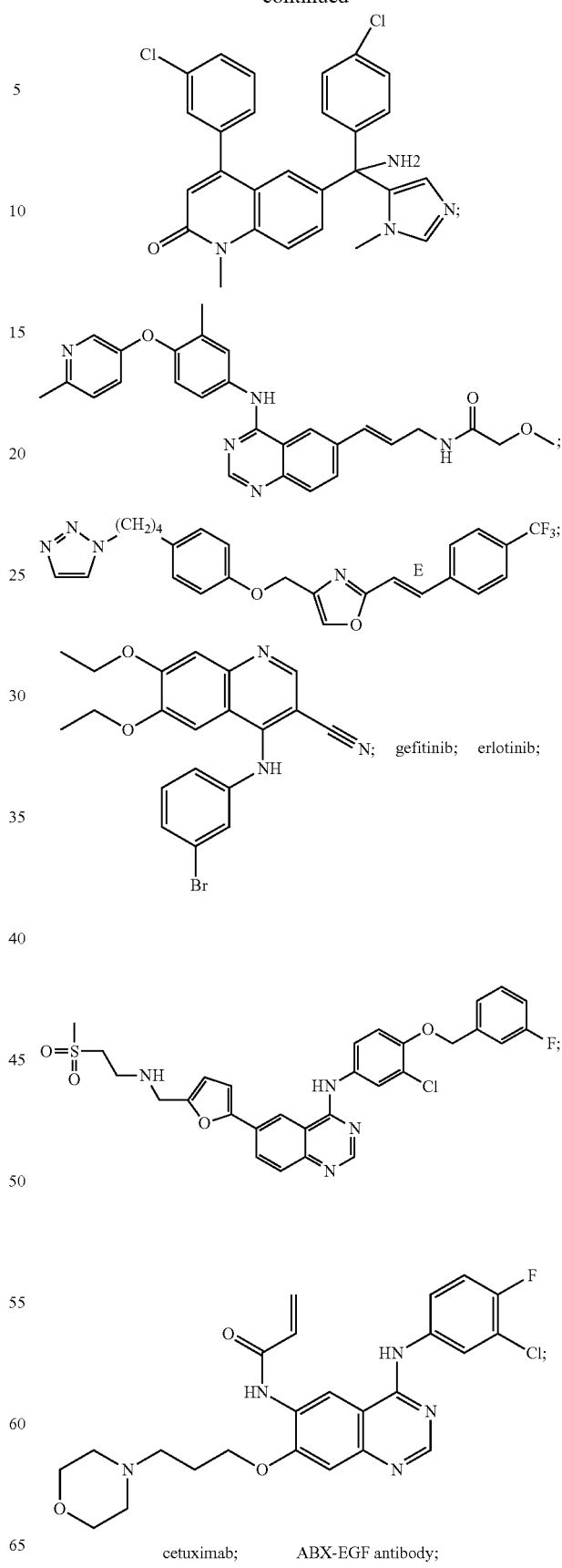

gefitinib; erlotinib;

cetuximab; ABX-EGF antibody;

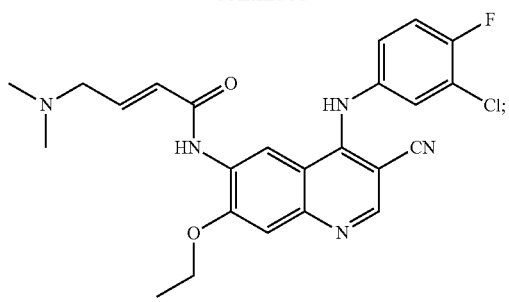
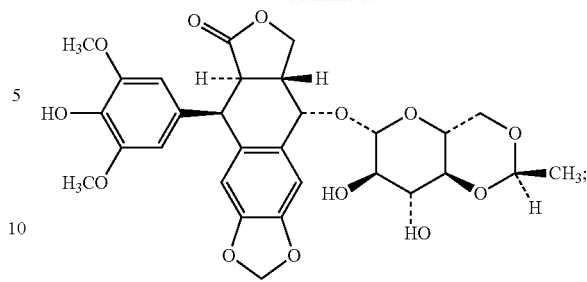
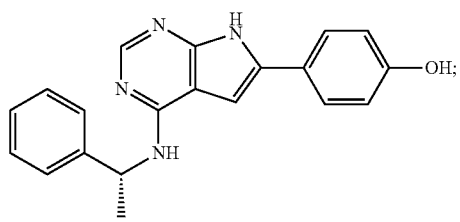
lapatinib; bevacizumab; VX-745; PD184352; temsirolimus; LY294002; LY292223; LY292696;
LY293684; LY293646; wortmannin; sorafenib; ZM336372; L-779,450;
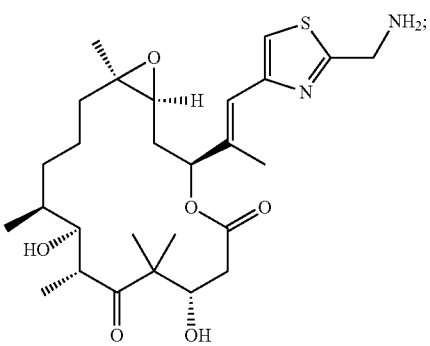
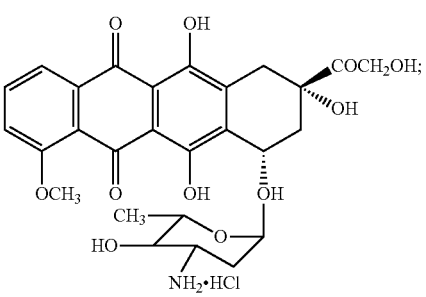
4-hydroxytamoxifen;
quercetin; octreotide; bortezomib;
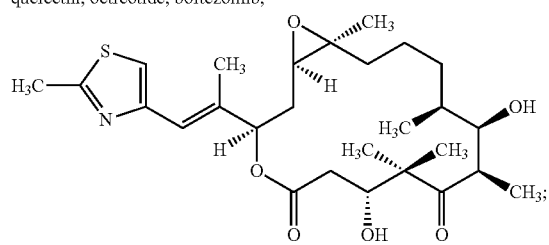
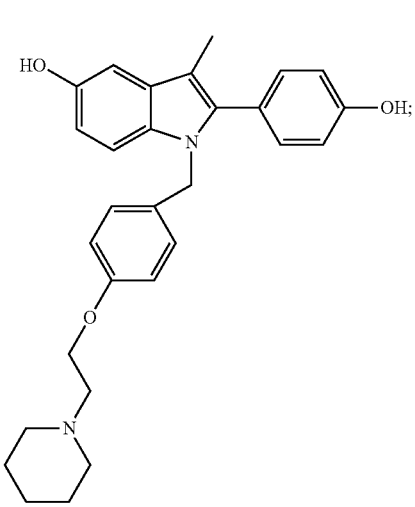
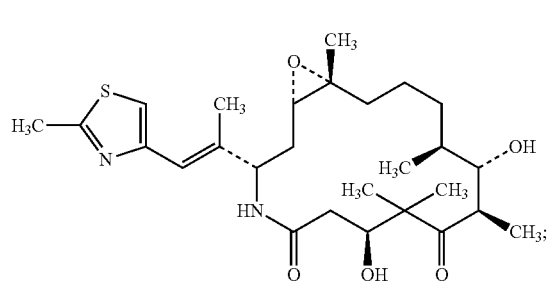

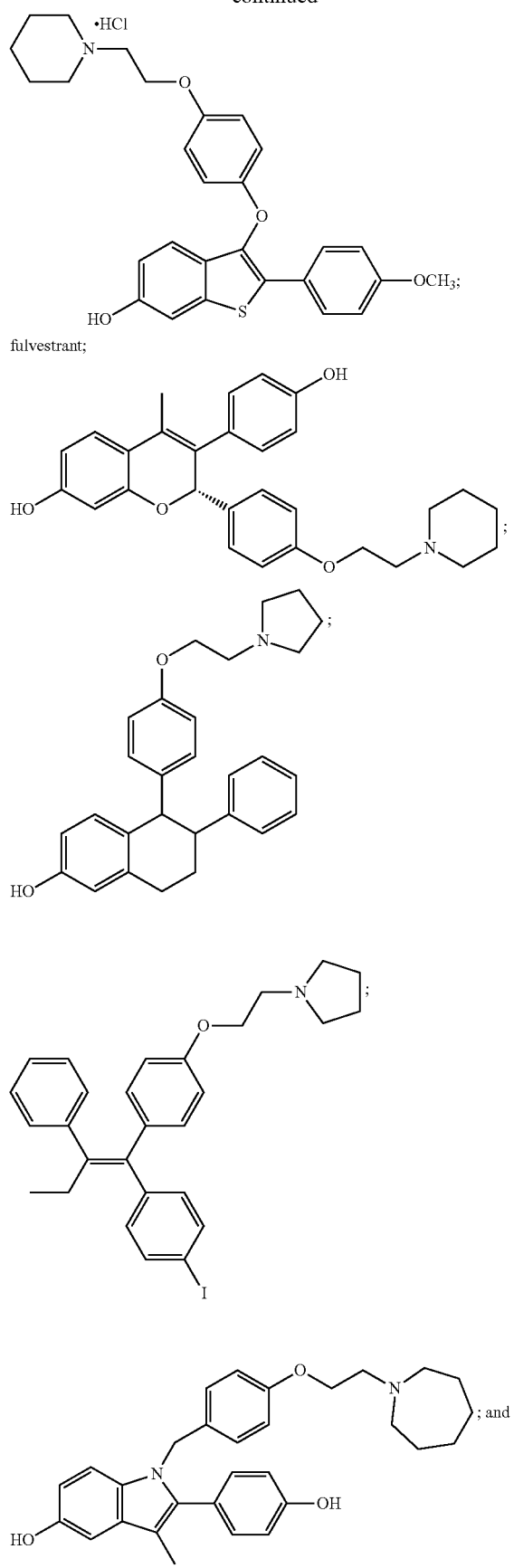

fulvestrant;

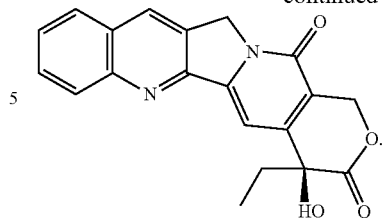

2. The composition of claim 1 wherein (a) comprises one or more isolated antibodies or antigen-binding fragments thereof comprising a light chain immunoglobulin amino acid sequence which comprises CDR-L1 comprising the amino acid sequence set forth in SEQ ID NO: 5, CDR-L2 comprising the amino acid sequence set forth in SEQ ID NO: 6 and CDR-L3 comprising the amino acid sequence set forth in SEQ ID NO: 7; and a heavy chain immunoglobulin amino acid sequence which comprises CDR-H1 comprising the amino acid sequence set forth in SEQ ID NO: 12, CDR-H2 comprising the amino acid sequence set forth in SEQ ID NO: 9 and CDR-H3 comprising the amino acid sequence set forth in SEQ ID NO: 10.

3. The composition of claim 2 wherein (a) comprises an isolated antibody comprising a light chain immunoglobulin comprising amino acids 20-128 of SEQ ID NO: 2 and a heavy chain immunoglobulin comprising amino acids of 20-137 of SEQ ID NO: 4.

4. The composition of claim 1 wherein a chemotherapeutic agent is one or more members selected from the group consisting of: lonafarnib, cetuximab, sorafenib, gefitinib, erlotinib, octreotide, and 4-hydroxytamoxifen.

5. A composition comprising:
(a) a monoclonal antibody, that specifically binds human insulin-like growth factor receptor 1, comprising a light chain immunoglobulin amino acid sequence which comprises CDR-L1 comprising the amino acid sequence set forth in SEQ ID NO: 5, CDR-L2 comprising the amino acid sequence set forth in SEQ ID NO: 6 and CDR-L3 comprising the amino acid sequence set forth in SEQ ID NO: 7; and a heavy chain immunoglobulin amino acid sequence which comprises CDR-H1 comprising the amino acid sequence set forth in SEQ ID NO: 8 or 12, CDR-H2 comprising the amino acid sequence set forth in SEQ ID NO: 9 and CDR-H3 comprising the amino acid sequence set forth in SEQ ID NO: 10; in association with
(b) one or more chemotherapeutic agents selected from the group consisting of: lonafarnib;

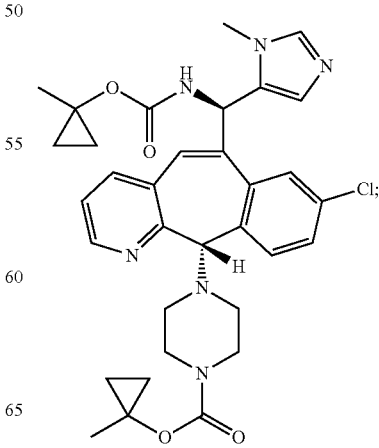

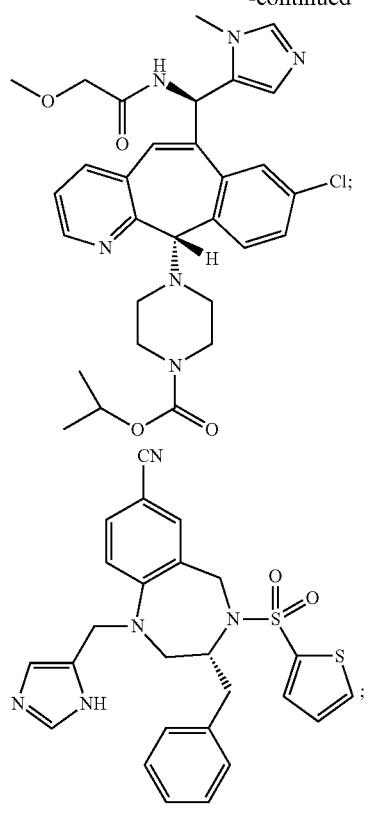
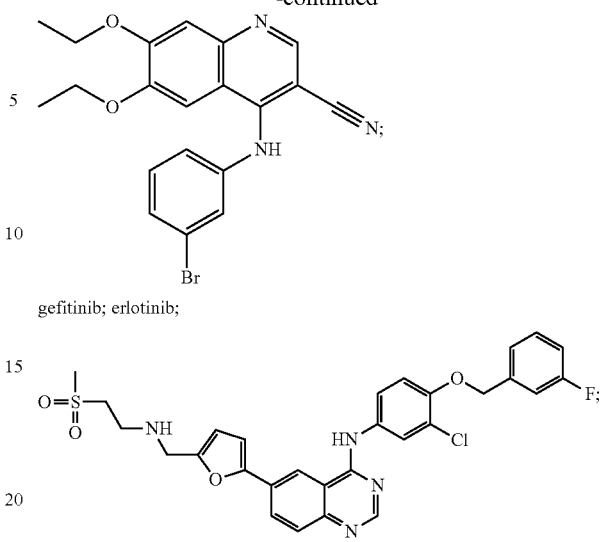
gefitinib; erlotinib;
ABX-EGF antibody; cetuximab;
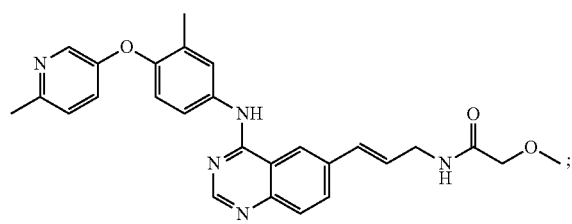
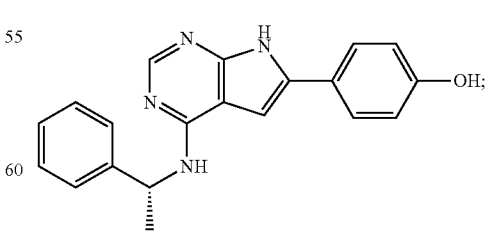
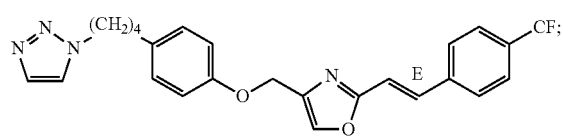
lapatinib; bevacizumab; VX-745; PD184352; temsirolimus; LY294002; LY292223; LY292696; LY293684; LY293646; wortmannin; sorafenib; ZM336372; L-779,450;

87
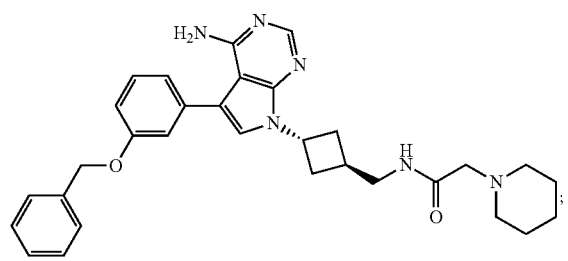
quercetin; octreotide; bortezomib;
88
-continued
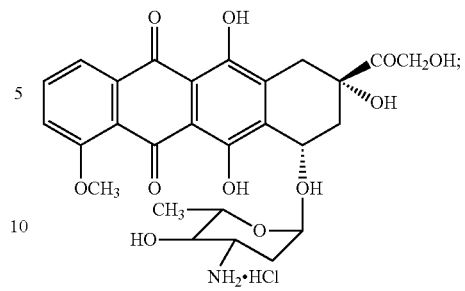
4-hydroxytamoxifen;
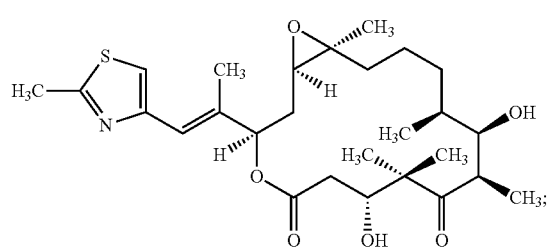
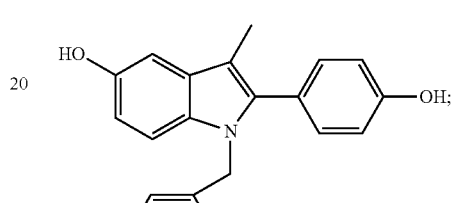
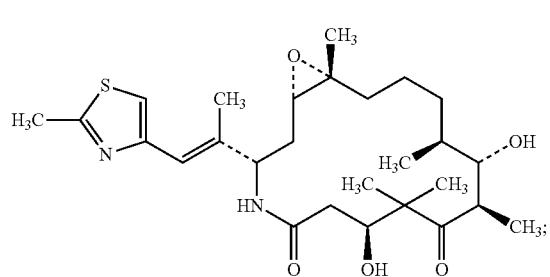
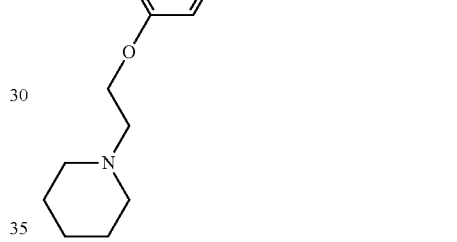
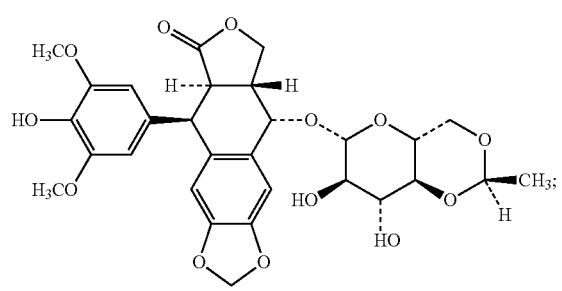
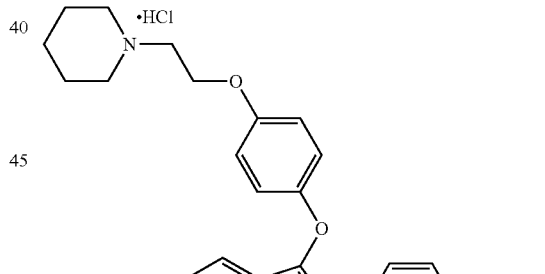
fulvestrant;
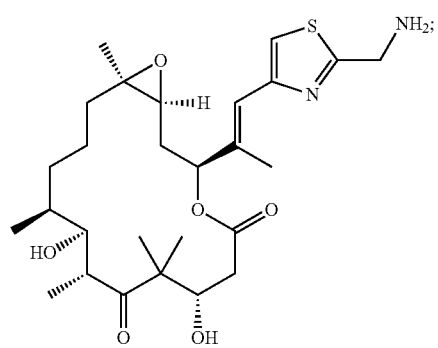
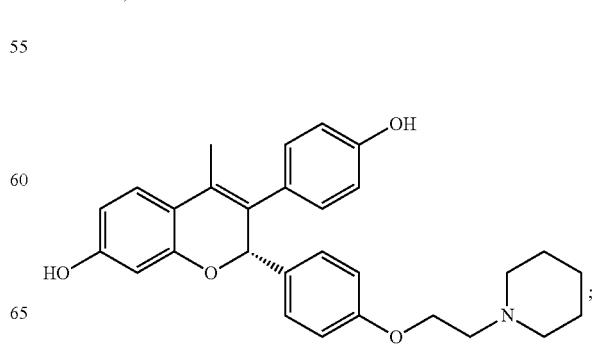

-continued

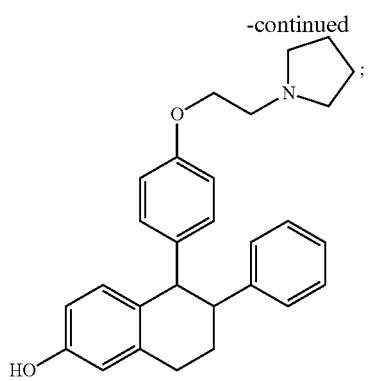

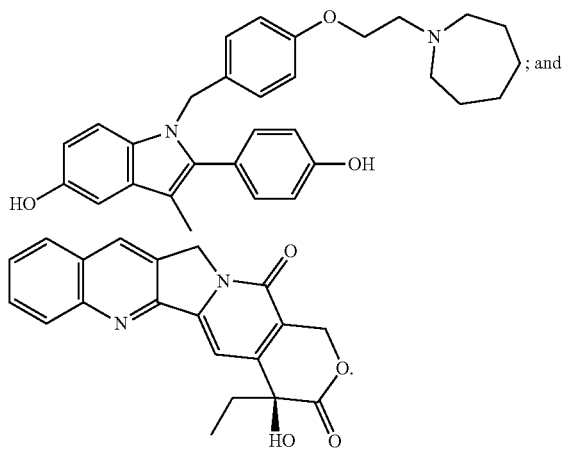

set forth in SEQ ID NO: 6 and CDR-L3 comprising the amino acid sequence set forth in SEQ ID NO: 7; and a heavy chain immunoglobulin amino acid sequence which comprises CDR-H1 comprising the amino acid sequence set forth in SEQ ID NO: 8 or 12, CDR-H2 comprising the amino acid sequence set forth in SEQ ID NO: 9 and CDR-H3 comprising the amino acid sequence set forth in SEQ ID NO: 10; in association with (b) one or more chemotherapeutic agents selected from the group consisting of:

lonafarnib;

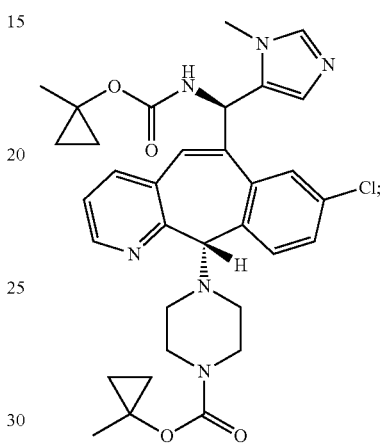

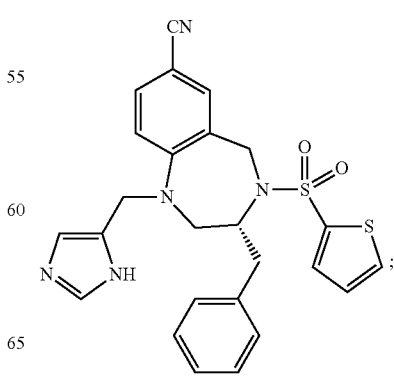

6. A method for treating a cancer or a tumor expressing human Insulin-like Growth Factor Receptor-I, wherein said cancer or tumor is selected form the group consisting of: bladder cancer, Wilm's cancer, ovarian cancer, pancreatic cancer, breast cancer, prostate cancer, bone cancer, lung cancer, colorectal cancer, cervical cancer, synovial sarcoma, or a vasoactive intestinal peptide secreting tumor in a mammalian subject in need of such treatment comprising administering a therapeutically effective amount of a composition comprising:

(a) one or more isolated antibodies or antigen-binding fragments thereof, that specifically bind human insulin-like growth factor receptor 1, comprising a light chain immunoglobulin amino acid sequence which comprises CDR-L1 comprising the amino acid sequence set forth in SEQ ID NO: 5, CDR-L2 comprising the amino acid sequence

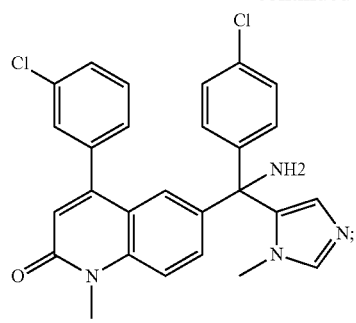
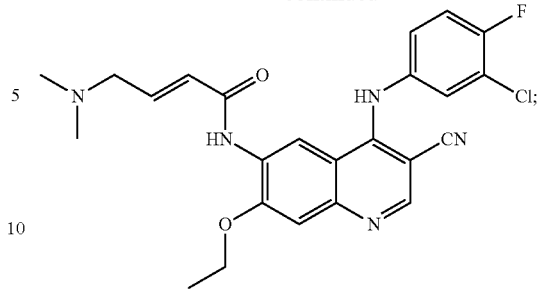
lapatinib; bevacizumab; VX-745; PD184352; temsirolimus; LY294002; LY292223; LY292696; LY293684; LY293646; wortmannin; sorafenib; ZM336372; L-779,450;
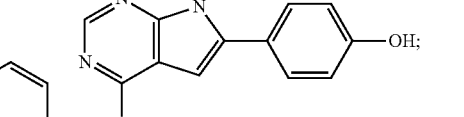
quercetin; octreotide; bortezomib;
gefitinib; erlotinib;
ABX-EGF antibody; cetuximab;

-continued
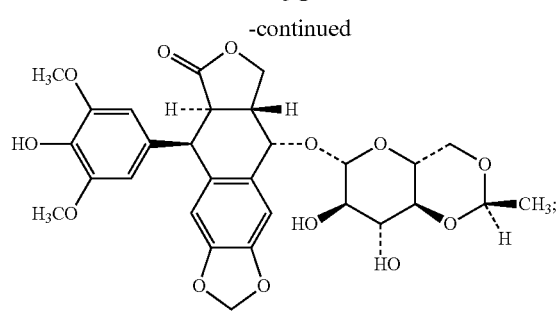
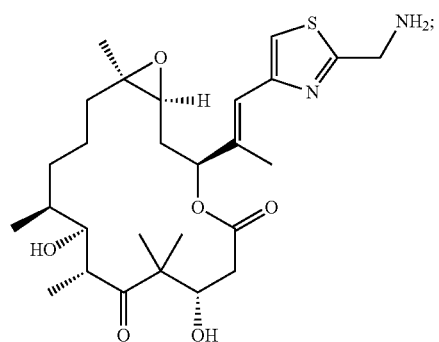
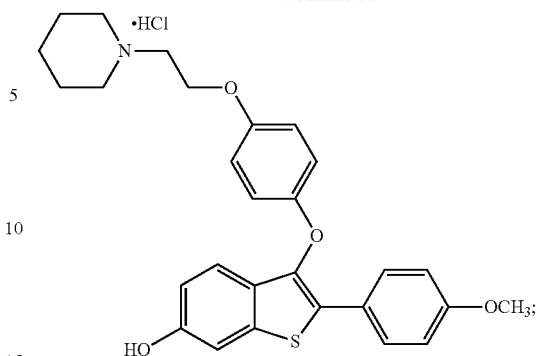
fulvestrant;
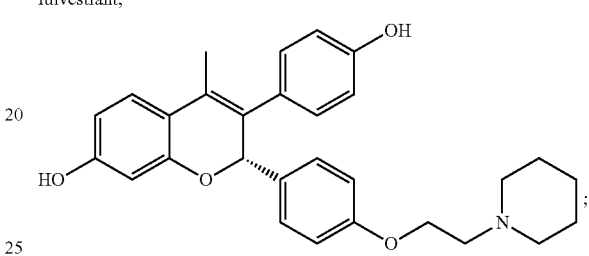
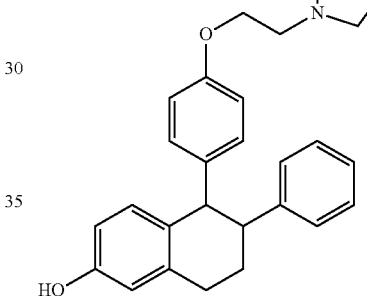
4-hydroxytamoxifen;
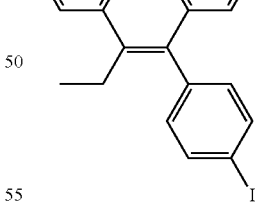
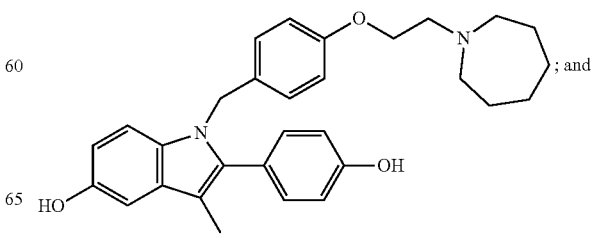
; and

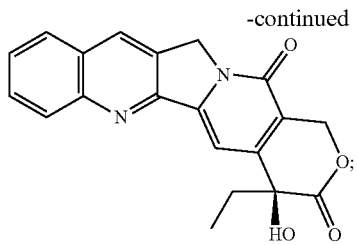

to the subject.

7. The method of claim 6 wherein (a) comprises an isolated antibody comprising a light chain immunoglobulin comprising amino acids 20-128 of SEQ ID NO: 2 and a heavy chain immunoglobulin comprising amino acids of 20-137 of SEQ ID NO: 4.

8. The method of claim 6 wherein a chemotherapeutic agent is one or more members selected from the group consisting of:
   lonafarnib;
   cetuximab;
   erlotinib;
   temsirolimus;
   sorafenib;
   gefitinib;
   fulvestrant;
   octreotide;
   bevacizumab;
   and
   4-hydroxytamoxifen.

9. The method of claim 6 wherein the medical condition is selected from the group consisting of Wilm's cancer, pancreatic cancer, breast cancer, prostate cancer, lung cancer, and colorectal cancer.

10. The method of claim 6 wherein the antibody or fragment is administered to the subject by a parenteral route.

11. A method for treating a cancer or a tumor expressing human Insulin-like Growth Factor Receptor-I, wherein said cancer or tumor is selected form the group consisting of: bladder cancer, Wilm's cancer, ovarian cancer, pancreatic cancer, breast cancer, prostate cancer, bone cancer, lung cancer, colorectal cancer, cervical cancer, synovial sarcoma, or a vasoactive intestinal peptide secreting tumor, in a mammalian subject in need of such treatment, comprising administering a therapeutically effective amount of a composition comprising:
   (a) a monoclonal antibody, that specifically binds human insulin-like growth factor receptor 1, comprising a light chain immunoglobulin comprising amino acids 20-128 of SEQ ID NO: 2 and a heavy chain immunoglobulin comprising amino acids 20-137 of SEQ ID NO: 4; in association with
   (b) one or more chemotherapeutic agents selected from the group consisting of:
   lonafarnib;
   cetuximab;
   erlotinib;
   rapamycin;
   temsirolimus;
   sorafenib;
   gefitinib;
   fulvestrant;
   octreotide;
   bevacizumab;
   and
   4-hydroxytamoxifen
   to the subject.

12. The method of claim 11 wherein the medical condition is selected from the group consisting of Wilm's cancer, pancreatic cancer, breast cancer, prostate cancer, lung cancer, and colorectal cancer.

13. The composition of claim 5 wherein a chemotherapeutic agent is lonafarnib; and wherein the monoclonal antibody comprises a light chain immunoglobulin comprising amino acids 20-128 of SEQ ID NO: 2; and a heavy chain immunoglobulin comprising amino acids of 20-137 of SEQ ID NO: 4.

14. The composition of claim 5 wherein a chemotherapeutic agent is cetuximab; and wherein the monoclonal antibody comprises a light chain immunoglobulin comprising amino acids 20-128 of SEQ ID NO: 2; and a heavy chain immunoglobulin comprising amino acids of 20-137 of SEQ ID NO: 4.

15. The composition of claim 5 wherein a chemotherapeutic agent is temsirolimus; and wherein the monoclonal antibody comprises a light chain immunoglobulin comprising amino acids 20-128 of SEQ ID NO: 2; and a heavy chain immunoglobulin comprising amino acids of 20-137 of SEQ ID NO: 4.

16. The composition of claim 5 wherein a chemotherapeutic agent is sorafenib; and wherein the monoclonal antibody comprises a light chain immunoglobulin comprising amino acids 20-128 of SEQ ID NO: 2; and a heavy chain immunoglobulin comprising amino acids of 20-137 of SEQ ID NO: 4.

17. The composition of claim 5 wherein a chemotherapeutic agent is gefitinib; and wherein the monoclonal antibody comprises a light chain immunoglobulin comprising amino acids 20-128 of SEQ ID NO: 2; and a heavy chain immunoglobulin comprising amino acids of 20-137 of SEQ ID NO: 4.

18. The composition of claim 5 wherein a chemotherapeutic agent is bevacizumab; and wherein the monoclonal antibody comprises a light chain immunoglobulin comprising amino acids 20-128 of SEQ ID NO: 2; and a heavy chain immunoglobulin comprising amino acids of 20-137 of SEQ ID NO: 4.

19. The composition of claim 5 wherein a chemotherapeutic agent is octreotide; and wherein the monoclonal antibody comprises a light chain immunoglobulin comprising amino acids 20-128 of SEQ ID NO: 2; and a heavy chain immunoglobulin comprising amino acids of 20-137 of SEQ ID NO: 4.

20. The composition of claim 5 wherein a chemotherapeutic agent is 4-hydroxytamoxifen; and wherein the monoclonal antibody comprises a light chain immunoglobulin comprising amino acids 20-128 of SEQ ID NO: 2; and a heavy chain immunoglobulin comprising amino acids of 20-137 of SEQ ID NO: 4.

21. The method of claim 6 wherein (a) comprises one or more isolated antibodies or antigen-binding fragments thereof comprising a light chain immunoglobulin amino acid sequence which comprises CDR-L1 comprising the amino acid sequence set forth in SEQ ID NO: 5, CDR-L2 comprising the amino acid sequence set forth in SEQ ID NO: 6 and CDR-L3 comprising the amino acid sequence set forth in SEQ ID NO: 7; and a heavy chain immunoglobulin amino acid sequence which comprises CDR-H1 comprising the amino acid sequence set forth in SEQ ID NO: 12, CDR-H2 comprising the amino acid sequence set forth in SEQ ID NO: 9 and CDR-H3 comprising the amino acid sequence set forth in SEQ ID NO: 10.

22. A composition comprising (a) one or more antibodies or antigen-binding fragments thereof, that specifically bind human insulin-like growth factor receptor 1, comprising a light chain immunoglobulin which comprises the amino acids 20-128 of the amino acid sequence set forth in SEQ ID NO: 2; or a heavy chain immunoglobulin which comprises amino acids 20-137 of the amino acid sequence set forth in SEQ ID NO: 4; or both; in association with
(b) one or more chemotherapeutic agents selected from the group consisting of lonafarnib;
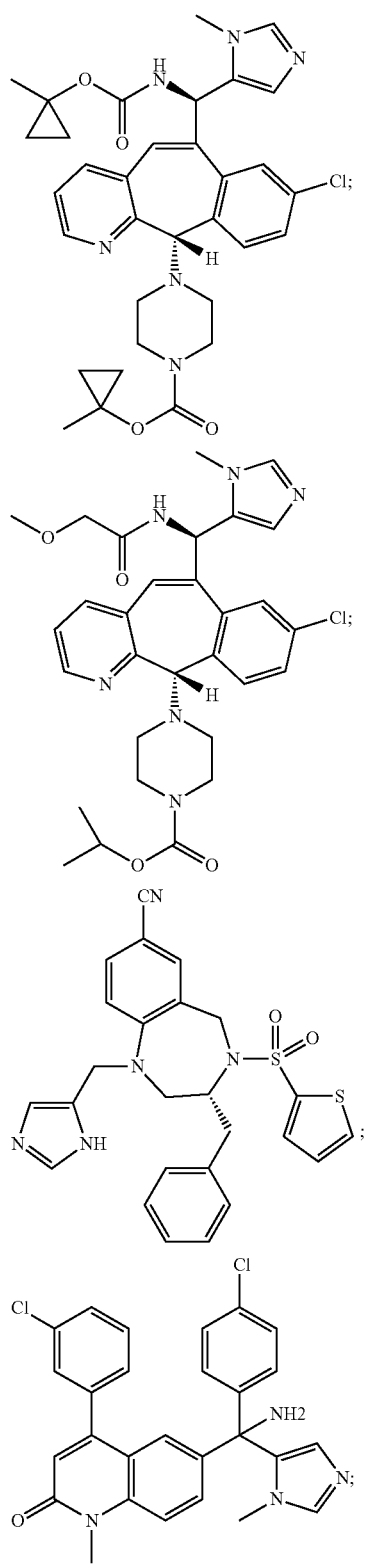
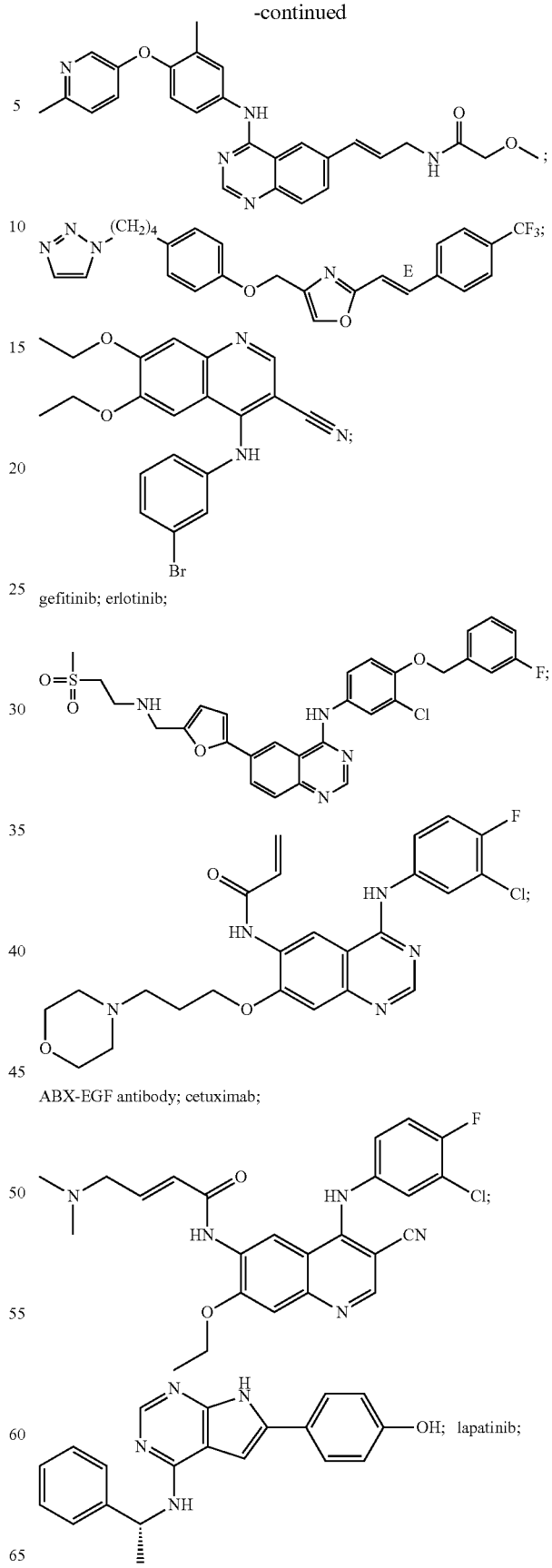
gefitinib; erlotinib;
ABX-EGF antibody; cetuximab;
lapatinib;

bevacizumab; VX-745; PD184352; temsirolimus; LY294002; LY292223; LY292696; LY293684; LY293646; wortmannin; sorafenib; ZM336372; L-779,450;
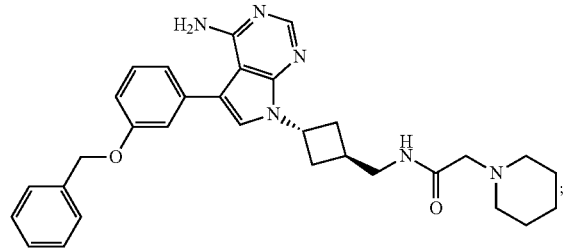
quercetin; octreotide; bortezomib;
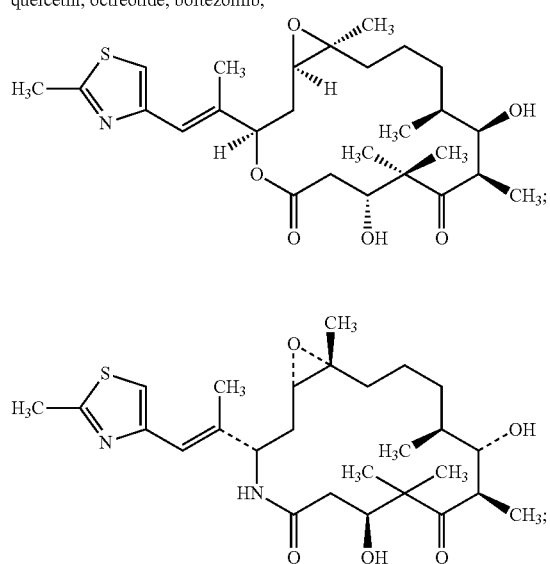
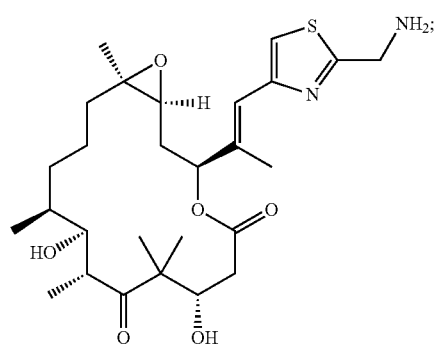
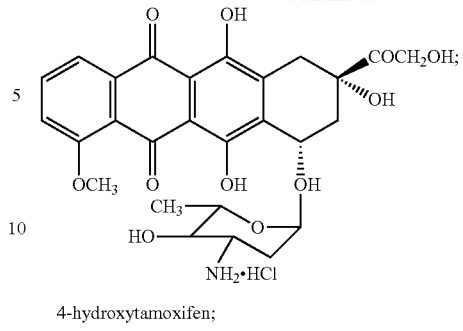
4-hydroxytamoxifen;
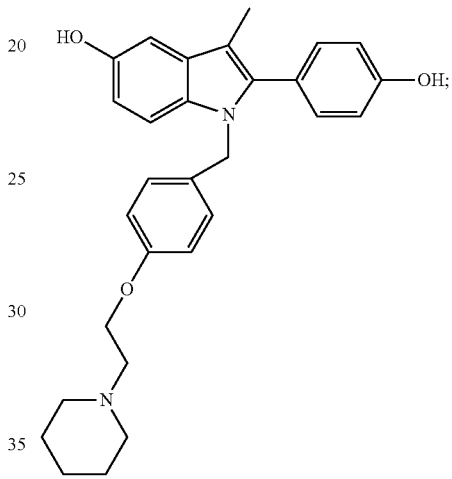
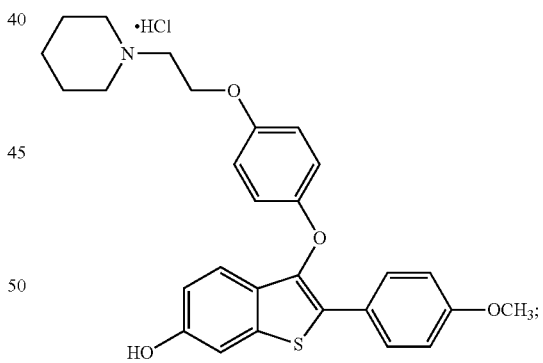
fulvestrant;
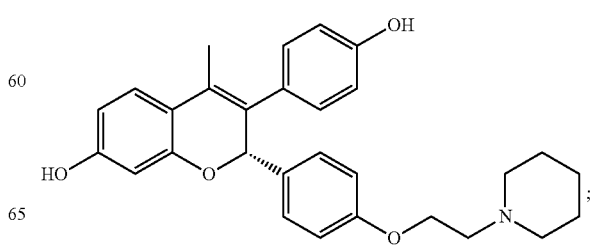

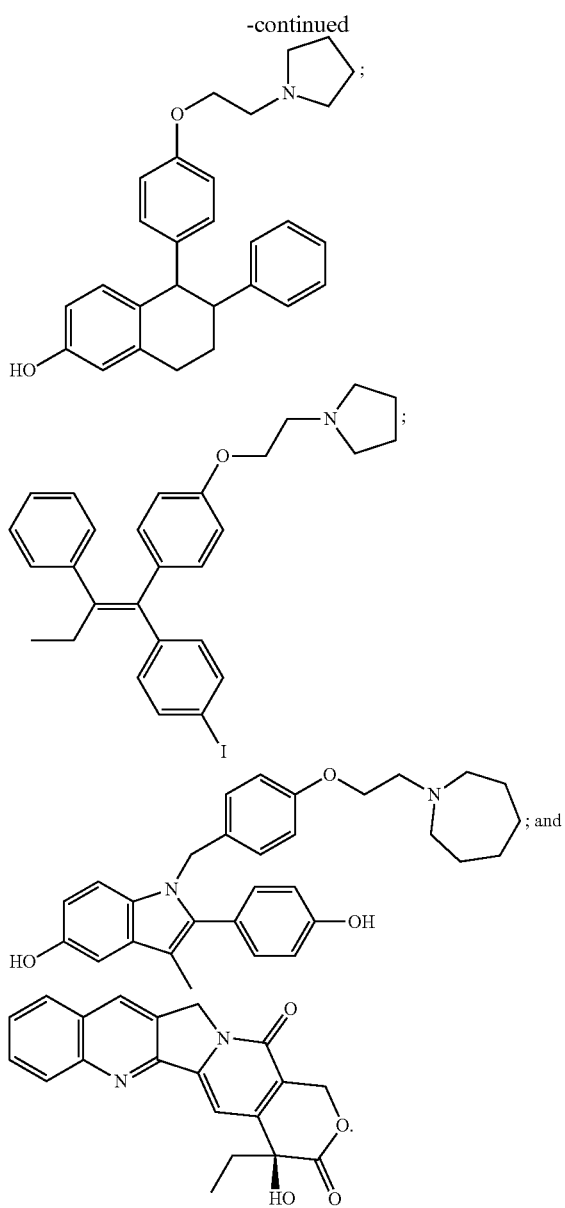

23. The composition of claim 5 wherein a chemotherapeutic agent is erlotinib; and wherein the monoclonal antibody comprises a light chain immunoglobulin comprising amino acids 20-128 of SEQ ID NO: 2; and a heavy chain immunoglobulin comprising amino acids of 20-137 of SEQ ID NO: 4.

24. The method of claim 12 wherein the medical condition is selected from the group consisting of Wilm's cancer, pancreatic cancer, breast cancer, prostate cancer, lung cancer, and colorectal cancer.

25. The method of claim 24 wherein the antibody is administered to the subject by a parenteral route.

26. The composition of claim 5 wherein the heavy chain immunoglobulin is linked to a γ1 immunoglobulin constant region and the light chain immunoglobulin is linked to a κ immunoglobulin constant region.

27. The composition of claim 1 wherein (a) comprises an isolated antibody comprising a light chain immunoglobulin comprising amino acids 20-128 of SEQ ID NO: 2, linked to a κ immunoglobulin constant region; and a heavy chain immunoglobulin comprising amino acids of 20-137 of SEQ ID NO: 4 linked to a γ1 immunoglobulin constant region.

28. The composition of claim 27 wherein the chemotherapeutic agent is bevacizumab.

29. The method of claim 12 wherein the medical condition is colorectal cancer, lung cancer or breast cancer and the chemotherapeutic agent is bevacizumab.

30. The method of claim 24 wherein the chemotherapeutic agent is lonafarnib.

31. The method of claim 24 wherein the chemotherapeutic agent is bevacizumab.

32. The method of claim 24 wherein the chemotherapeutic agent is temsirolimus.

33. The method of claim 24 wherein the chemotherapeutic agent is sorafenib.

34. The method of claim 24 wherein the chemotherapeutic agent is cetuximab.

35. The method of claim 24 wherein the chemotherapeutic agent is erlotinib.

36. The method of claim 24 wherein the chemotherapeutic agent is rapamycin.

37. The method of claim 24 wherein the chemotherapeutic agent is gefitinib.

38. The method of claim 24 wherein the chemotherapeutic agent is fulvestrant.

39. The method of claim 24 wherein the chemotherapeutic agent is octreotide.

40. The method of claim 24 wherein the chemotherapeutic agent is 4-hydroxytamoxifen.

41. The method of claim 11 wherein the medical condition is colorectal cancer, lung cancer or breast cancer.

* * * * *

SEQUENCE LISTING

```
<160> NUMBER OF SEQ ID NOS: 14

<210> SEQ ID NO 1
<211> LENGTH: 384
<212> TYPE: DNA
<213> ORGANISM: Homo sapiens
<220> FEATURE:
<221> NAME/KEY: CDS
<222> LOCATION: (1)..(384)
<223> OTHER INFORMATION:

<400> SEQUENCE: 1 atg tcg cca tca caa ctc att ggg ttt ctg ctg ctc tgg gtt cca gcc      48
Met Ser Pro Ser Gln Leu Ile Gly Phe Leu Leu Leu Trp Val Pro Ala
1               5                   10                  15 tcc agg ggt gaa att gtg ctg act cag agc cca ggt acc ctg tct gtg      96
Ser Arg Gly Glu Ile Val Leu Thr Gln Ser Pro Gly Thr Leu Ser Val
            20                  25                  30
```

```
tct cca ggc gag aga gcc acc ctc tcc tgc cgg gcc agt cag agc att      144
Ser Pro Gly Glu Arg Ala Thr Leu Ser Cys Arg Ala Ser Gln Ser Ile
        35                  40                  45 ggt agt agc tta cac tgg tac cag cag aaa cca ggt cag gct cca agg      192
Gly Ser Ser Leu His Trp Tyr Gln Gln Lys Pro Gly Gln Ala Pro Arg
50                  55                  60 ctt ctc atc aag tat gca tcc cag tcc ctc tca ggg atc ccc gat agg      240
Leu Leu Ile Lys Tyr Ala Ser Gln Ser Leu Ser Gly Ile Pro Asp Arg
65                  70                  75                  80 ttc agt ggc agt gga tct ggg aca gat ttc acc ctc acc atc agt aga      288
Phe Ser Gly Ser Gly Ser Gly Thr Asp Phe Thr Leu Thr Ile Ser Arg
                85                  90                  95 ctg gag cct gaa gat ttc gca gtg tat tac tgt cat cag agt agt cgt      336
Leu Glu Pro Glu Asp Phe Ala Val Tyr Tyr Cys His Gln Ser Ser Arg
            100                 105                 110 tta cct cac act ttc ggc caa ggg acc aag gtg gag atc aaa cgt aca      384
Leu Pro His Thr Phe Gly Gln Gly Thr Lys Val Glu Ile Lys Arg Thr
        115                 120                 125

<210> SEQ ID NO 2
<211> LENGTH: 128
<212> TYPE: PRT
<213> ORGANISM: Homo sapiens

<400> SEQUENCE: 2

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 3
<211> LENGTH: 411
<212> TYPE: DNA
<213> ORGANISM: Homo sapiens
<220> FEATURE:
<221> NAME/KEY: CDS
<222> LOCATION: (1)..(411)
<223> OTHER INFORMATION:

<400> SEQUENCE: 3 atg gag ttt ggg ctg agc tgg gtt ttc ctt gtt gct ata tta aaa ggt      48
Met Glu Phe Gly Leu Ser Trp Val Phe Leu Val Ala Ile Leu Lys Gly
1               5                   10                  15 gtc cag tgt gag gtt cag ctg gtg cag tct ggg gga ggc ttg gta aag      96
Val Gln Cys Glu Val Gln Leu Val Gln Ser Gly Gly Gly Leu Val Lys
            20                  25                  30 cct ggg ggg tcc ctg aga ctc tcc tgt gca gcc tct gga ttc acc ttc      144
Pro Gly Gly Ser Leu Arg Leu Ser Cys Ala Ala Ser Gly Phe Thr Phe
        35                  40                  45
```

```
agt agc ttt gct atg cac tgg gtt cgc cag gct cca gga aaa ggt ctg      192
Ser Ser Phe Ala Met His Trp Val Arg Gln Ala Pro Gly Lys Gly Leu
    50                  55                  60 gag tgg ata tca gtt att gat act cgt ggt gcc aca tac tat gca gac      240
Glu Trp Ile Ser Val Ile Asp Thr Arg Gly Ala Thr Tyr Tyr Ala Asp
65                  70                  75                  80 tcc gtg aag ggc cga ttc acc atc tcc aga gac aat gcc aag aac tcc      288
Ser Val Lys Gly Arg Phe Thr Ile Ser Arg Asp Asn Ala Lys Asn Ser
                85                  90                  95 ttg tat ctt caa atg aac agc ctg aga gcc gag gac act gct gtg tat      336
Leu Tyr Leu Gln Met Asn Ser Leu Arg Ala Glu Asp Thr Ala Val Tyr
            100                 105                 110 tac tgt gca aga ctg ggg aac ttc tac tac ggt atg gac gtc tgg ggc      384
Tyr Cys Ala Arg Leu Gly Asn Phe Tyr Tyr Gly Met Asp Val Trp Gly
        115                 120                 125 caa ggg acc acg gtc acc gtc tcc tca                                  411
Gln Gly Thr Thr Val Thr Val Ser Ser
130                 135
```

<210> SEQ ID NO 4
<211> LENGTH: 137
<212> TYPE: PRT
<213> ORGANISM: Homo sapiens

<400> SEQUENCE: 4

```
Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135
```

<210> SEQ ID NO 5
<211> LENGTH: 11
<212> TYPE: PRT
<213> ORGANISM: Homo sapiens

<400> SEQUENCE: 5

```
Arg Ala Ser Gln Ser Ile Gly Ser Ser Leu His
1               5                   10
```

<210> SEQ ID NO 6
<211> LENGTH: 7
<212> TYPE: PRT
<213> ORGANISM: Homo sapiens

<400> SEQUENCE: 6

```
Tyr Ala Ser Gln Ser Leu Ser
1               5
```

<210> SEQ ID NO 7
<211> LENGTH: 9
<212> TYPE: PRT
<213> ORGANISM: Homo sapiens

<400> SEQUENCE: 7

His Gln Ser Ser Arg Leu Pro His Thr
1               5

<210> SEQ ID NO 8
<211> LENGTH: 5
<212> TYPE: PRT
<213> ORGANISM: Homo sapiens

<400> SEQUENCE: 8

Ser Phe Ala Met His
1               5

<210> SEQ ID NO 9
<211> LENGTH: 16
<212> TYPE: PRT
<213> ORGANISM: Homo sapiens

<400> SEQUENCE: 9

Val Ile Asp Thr Arg Gly Ala Thr Tyr Tyr Ala Asp Ser Val Lys Gly
1               5                   10                  15

<210> SEQ ID NO 10
<211> LENGTH: 10
<212> TYPE: PRT
<213> ORGANISM: Homo sapiens

<400> SEQUENCE: 10

Leu Gly Asn Phe Tyr Tyr Gly Met Asp Val
1               5                   10

<210> SEQ ID NO 11
<211> LENGTH: 1367
<212> TYPE: PRT
<213> ORGANISM: Homo sapiens

<400> SEQUENCE: 11

Met Lys Ser Gly Ser Gly Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
        50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

```
Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
            165                 170                 175

Glu Cys Gly Asp Leu Cys Pro Gly Thr Met Glu Lys Pro Met Cys
            180                 185                 190

Glu Lys Thr Thr Ile Asn Asn Glu Tyr Asn Tyr Arg Cys Trp Thr Thr
            195                 200                 205

Asn Arg Cys Gln Lys Met Cys Pro Ser Thr Cys Gly Lys Arg Ala Cys
210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
            245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
            325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
            405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
            450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
            485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
            515                 520                 525

Glu Ala Pro Phe Lys Asn Val Thr Glu Tyr Asp Gly Gln Asp Ala Cys
            530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
            565                 570                 575
```

-continued

Tyr Ala Val Tyr Val Lys Ala Val Thr Leu Thr Met Val Glu Asn Asp
            580                 585                 590
His Ile Arg Gly Ala Lys Ser Glu Ile Leu Tyr Ile Arg Thr Asn Ala
            595                 600                 605
Ser Val Pro Ser Ile Pro Leu Asp Val Leu Ser Ala Ser Asn Ser Ser
610                 615                 620
Ser Gln Leu Ile Val Lys Trp Asn Pro Pro Ser Leu Pro Asn Gly Asn
625                 630                 635                 640
Leu Ser Tyr Tyr Ile Val Arg Trp Gln Arg Gln Pro Gln Asp Gly Tyr
                645                 650                 655
Leu Tyr Arg His Asn Tyr Cys Ser Lys Asp Lys Ile Pro Ile Arg Lys
            660                 665                 670
Tyr Ala Asp Gly Thr Ile Asp Ile Glu Val Thr Gly Asn Pro Lys
            675                 680                 685
Thr Glu Val Cys Gly Gly Glu Lys Gly Pro Cys Cys Ala Cys Pro Lys
        690                 695                 700
Thr Glu Ala Glu Lys Gln Ala Glu Lys Glu Glu Ala Glu Tyr Arg Lys
705                 710                 715                 720
Val Phe Glu Asn Phe Leu His Asn Ser Ile Phe Val Pro Arg Pro Glu
                725                 730                 735
Arg Lys Arg Arg Asp Val Met Gln Val Ala Asn Thr Thr Met Ser Ser
            740                 745                 750
Arg Ser Arg Asn Thr Thr Ala Ala Asp Thr Tyr Asn Ile Thr Asp Pro
        755                 760                 765
Glu Glu Leu Glu Thr Glu Tyr Pro Phe Phe Glu Ser Arg Val Asp Asn
        770                 775                 780
Lys Glu Arg Thr Val Ile Ser Asn Leu Arg Pro Phe Thr Leu Tyr Arg
785                 790                 795                 800
Ile Asp Ile His Ser Cys Asn His Glu Ala Glu Lys Leu Gly Cys Ser
                805                 810                 815
Ala Ser Asn Phe Val Phe Ala Arg Thr Met Pro Ala Glu Gly Ala Asp
            820                 825                 830
Asp Ile Pro Gly Pro Val Thr Trp Glu Pro Arg Pro Glu Asn Ser Ile
            835                 840                 845
Phe Leu Lys Trp Pro Glu Pro Glu Asn Pro Asn Gly Leu Ile Leu Met
850                 855                 860
Tyr Glu Ile Lys Tyr Gly Ser Gln Val Glu Asp Gln Arg Glu Cys Val
865                 870                 875                 880
Ser Arg Gln Glu Tyr Arg Lys Tyr Gly Gly Ala Lys Leu Asn Arg Leu
                885                 890                 895
Asn Pro Gly Asn Tyr Thr Ala Arg Ile Gln Ala Thr Ser Leu Ser Gly
            900                 905                 910
Asn Gly Ser Trp Thr Asp Pro Val Phe Phe Tyr Val Gln Ala Lys Thr
            915                 920                 925
Gly Tyr Glu Asn Phe Ile His Leu Ile Ile Ala Leu Pro Val Ala Val
        930                 935                 940
Leu Leu Ile Val Gly Gly Leu Val Ile Met Leu Tyr Val Phe His Arg
945                 950                 955                 960
Lys Arg Asn Asn Ser Arg Leu Gly Asn Gly Val Leu Tyr Ala Ser Val
                965                 970                 975
Asn Pro Glu Tyr Phe Ser Ala Ala Asp Val Tyr Val Pro Asp Glu Trp
            980                 985                 990
Glu Val Ala Arg Glu Lys Ile Thr  Met Ser Arg Glu Leu  Gly Gln Gly

```
                        995                 1000                1005
Ser Phe Gly Met Val Tyr Glu Gly Val Ala Lys Gly Val Val Lys
    1010                1015                1020

Asp Glu Pro Glu Thr Arg Val Ala Ile Lys Thr Val Asn Glu Ala
    1025                1030                1035

Ala Ser Met Arg Glu Arg Ile Glu Phe Leu Asn Glu Ala Ser Val
    1040                1045                1050

Met Lys Glu Phe Asn Cys His His Val Val Arg Leu Leu Gly Val
    1055                1060                1065

Val Ser Gln Gly Gln Pro Thr Leu Val Ile Met Glu Leu Met Thr
    1070                1075                1080

Arg Gly Asp Leu Lys Ser Tyr Leu Arg Ser Leu Arg Pro Glu Met
    1085                1090                1095

Glu Asn Asn Pro Val Leu Ala Pro Pro Ser Leu Ser Lys Met Ile
    1100                1105                1110

Gln Met Ala Gly Glu Ile Ala Asp Gly Met Ala Tyr Leu Asn Ala
    1115                1120                1125

Asn Lys Phe Val His Arg Asp Leu Ala Ala Arg Asn Cys Met Val
    1130                1135                1140

Ala Glu Asp Phe Thr Val Lys Ile Gly Asp Phe Gly Met Thr Arg
    1145                1150                1155

Asp Ile Tyr Glu Thr Asp Tyr Tyr Arg Lys Gly Gly Lys Gly Leu
    1160                1165                1170

Leu Pro Val Arg Trp Met Ser Pro Glu Ser Leu Lys Asp Gly Val
    1175                1180                1185

Phe Thr Thr Tyr Ser Asp Val Trp Ser Phe Gly Val Val Leu Trp
    1190                1195                1200

Glu Ile Ala Thr Leu Ala Glu Gln Pro Tyr Gln Gly Leu Ser Asn
    1205                1210                1215

Glu Gln Val Leu Arg Phe Val Met Glu Gly Gly Leu Leu Asp Lys
    1220                1225                1230

Pro Asp Asn Cys Pro Asp Met Leu Phe Glu Leu Met Arg Met Cys
    1235                1240                1245

Trp Gln Tyr Asn Pro Lys Met Arg Pro Ser Phe Leu Glu Ile Ile
    1250                1255                1260

Ser Ser Ile Lys Glu Glu Met Glu Pro Gly Phe Arg Glu Val Ser
    1265                1270                1275

Phe Tyr Tyr Ser Glu Glu Asn Lys Leu Pro Glu Pro Glu Glu Leu
    1280                1285                1290

Asp Leu Glu Pro Glu Asn Met Glu Ser Val Pro Leu Asp Pro Ser
    1295                1300                1305

Ala Ser Ser Ser Ser Leu Pro Leu Pro Asp Arg His Ser Gly His
    1310                1315                1320

Lys Ala Glu Asn Gly Pro Gly Pro Gly Val Leu Val Leu Arg Ala
    1325                1330                1335

Ser Phe Asp Glu Arg Gln Pro Tyr Ala His Met Asn Gly Gly Arg
    1340                1345                1350

Lys Asn Glu Arg Ala Leu Pro Leu Pro Gln Ser Ser Thr Cys
    1355                1360                1365

<210> SEQ ID NO 12
<211> LENGTH: 10
<212> TYPE: PRT
<213> ORGANISM: Homo sapiens
```

-continued

<400> SEQUENCE: 12

Gly Phe Thr Phe Ser Ser Phe Ala Met His
1               5                   10

<210> SEQ ID NO 13
<211> LENGTH: 128
<212> TYPE: PRT
<213> ORGANISM: Homo sapiens

<400> SEQUENCE: 13

Met Ser Pro Ser Gln Leu Ile Gly Phe Leu Leu Leu Trp Val Pro Ala
1               5                   10                  15

Ser Arg Gly Glu Ile Val Leu Thr Gln Val Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Arg
            100                 105                 110

Leu Pro His Thr Phe Gly Gly Gly Thr Lys Val Glu Ile Lys Arg Thr
        115                 120                 125

<210> SEQ ID NO 14
<211> LENGTH: 137
<212> TYPE: PRT
<213> ORGANISM: Homo sapiens

<400> SEQUENCE: 14

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val His
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Met Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
        130                 135